(12) United States Patent
Sasisekharan et al.

(10) Patent No.: US 8,173,384 B2
(45) Date of Patent: *May 8, 2012

(54) METHODS FOR ANALYZING OR PROCESSING A HEPARIN SAMPLE

(75) Inventors: Ram Sasisekharan, Bedford, MA (US); Ganesh Venkataraman, Bedford, MA (US); Zachary Shriver, Cambridge, MA (US); Dongfang Liu, Yorktown Heights, NY (US); Mallikarjun Sundaram, Randolph, NJ (US); Yiwei Qi, Andover, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/509,774

(22) Filed: Jul. 27, 2009

(65) Prior Publication Data

US 2010/0062468 A1 Mar. 11, 2010

Related U.S. Application Data

(60) Continuation of application No. 11/606,623, filed on Nov. 30, 2006, now Pat. No. 7,585,642, which is a continuation of application No. 11/183,323, filed on Jul. 15, 2005, now Pat. No. 7,399,604, which is a division of application No. 09/951,138, filed on Sep. 12, 2001, now Pat. No. 7,083,937.

(60) Provisional application No. 60/231,994, filed on Sep. 12, 2000.

(51) Int. Cl.
*C12Q 1/56* (2006.01)

(52) U.S. Cl. ............. 435/13; 514/56; 536/1.11

(58) Field of Classification Search ............ 435/13; 514/56; 536/1.11
See application file for complete search history.

(56) References Cited

U.S. PATENT DOCUMENTS

| | | |
|---|---|---|
| 4,281,108 A | 7/1981 | Fussi |
| 4,341,869 A | 7/1982 | Langer, Jr. et al. |
| 4,373,023 A | 2/1983 | Langer et al. |
| 4,396,762 A | 8/1983 | Langer et al. |
| 4,443,545 A | 4/1984 | Langer, Jr. et al. |
| 4,551,296 A | 11/1985 | Kavesh et al. |
| 4,745,105 A | 5/1988 | Griffin et al. |
| 4,757,056 A | 7/1988 | Van Gorp et al. |
| 4,830,013 A | 5/1989 | Maxwell |
| 4,847,338 A | 7/1989 | Linhardt et al. |
| 4,928,694 A | 5/1990 | Maxwell |
| 4,942,156 A | 7/1990 | Foley et al. |
| 4,981,955 A | 1/1991 | Lopez |
| 4,990,502 A | 2/1991 | Lormeau et al. |
| 5,010,063 A | 4/1991 | Piani et al. |
| 5,039,529 A | 8/1991 | Bergendal et al. |
| 5,104,860 A | 4/1992 | Piani et al. |
| 5,106,734 A | 4/1992 | Nielsen |
| 5,152,784 A | 10/1992 | Tsilibary |
| 5,164,378 A | 11/1992 | Conti et al. |
| 5,169,772 A | 12/1992 | Zimmerman et al. |
| 5,204,323 A | 4/1993 | Findlay et al. |
| 5,252,339 A | 10/1993 | Cristofori et al. |
| 5,262,325 A | 11/1993 | Zimmermann et al. |
| 5,284,558 A | 2/1994 | Linhardt et al. |
| 5,290,695 A | 3/1994 | Morikawa et al. |
| 5,338,677 A | 8/1994 | Zimmermann et al. |
| 5,389,539 A | 2/1995 | Sasisekharan et al. |
| 5,453,171 A | 9/1995 | Ma et al. |
| 5,474,987 A | 12/1995 | Cohen et al. |
| 5,567,417 A | 10/1996 | Sasisekharan et al. |
| 5,569,366 A | 10/1996 | Chen et al. |
| 5,569,600 A | 10/1996 | Sasisekharan et al. |
| 5,576,304 A | 11/1996 | Kakkar et al. |
| 5,599,801 A | 2/1997 | Branellec et al. |
| 5,607,859 A | 3/1997 | Biemann et al. |
| 5,618,917 A | 4/1997 | Toback et al. |
| 5,619,421 A | 4/1997 | Venkataraman et al. |
| 5,681,733 A | 10/1997 | Su et al. |
| 5,687,090 A | 11/1997 | Chen et al. |
| 5,714,376 A | 2/1998 | Sasisekharan et al. |
| 5,744,515 A | 4/1998 | Clapper |
| 5,752,019 A | 5/1998 | Rigoutsos et al. |
| 5,753,445 A | 5/1998 | Fillit et al. |
| 5,759,767 A | 6/1998 | Lakowicz et al. |
| 5,763,427 A | 6/1998 | Weitz et al. |
| 5,795,875 A | 8/1998 | Holme et al. |
| 5,808,021 A | 9/1998 | Holme et al. |

(Continued)

FOREIGN PATENT DOCUMENTS

EP 0244236 A2 11/1987

(Continued)

OTHER PUBLICATIONS

[No Author Listed] MIT News Office. "MIT Tool Impacts Multi-Billion Dollar Drug." Online at <http://www.sciencedaily.com>. Printed Sep. 21, 2000.

Alderman et al., Continuous subcutaneous heparin infusion for treatment of Trousseau's syndrome. Ann Pharmacother. Jul.-Aug. 1995;29(7-8):710-3.

Ameer et al., A new approach to regional heparinization: design and development of a novel immobilized heparinase device. Blood Purification Meeting Information: The International Conference on Continuous Renal Replacement Therapies. 1998;16(2):107-18. Abstrace only.

(Continued)

*Primary Examiner* — Ralph Gitomer
(74) *Attorney, Agent, or Firm* — Wolf, Greenfield & Sacks, P.C.

(57) ABSTRACT

The invention relates to methods and products for analyzing or processing a heparin sample. In one embodiment, the methods comprise contacting the sample with heparinase I, heparinase II and heparinase III, determining the amount of a signature component in the sample using a separation method, and making a determination about the sample based upon a comparison of the amount of the signature component in the sample to a reference database for a heparin.

30 Claims, 14 Drawing Sheets

U.S. PATENT DOCUMENTS

| | | | |
|---|---|---|---|
| 5,824,299 | A | 10/1998 | Luster et al. |
| 5,830,726 | A | 11/1998 | Sasisekharan et al. |
| 5,856,928 | A | 1/1999 | Yan |
| 5,879,713 | A | 3/1999 | Roth et al. |
| 5,919,693 | A | 7/1999 | Su et al. |
| 5,922,358 | A | 7/1999 | Doutremepuich et al. |
| 5,952,653 | A | 9/1999 | Covey et al. |
| 5,968,822 | A | 10/1999 | Pecker et al. |
| 5,997,863 | A | 12/1999 | Zimmermann et al. |
| 6,013,628 | A | 1/2000 | Skubitz et al. |
| 6,190,875 | B1 | 2/2001 | Ben-Artzi et al. |
| 6,217,863 | B1 | 4/2001 | Godavarti et al. |
| 6,268,146 | B1 | 7/2001 | Shultz et al. |
| 6,291,439 | B1 | 9/2001 | Klock |
| 6,309,853 | B1 | 10/2001 | Friedman et al. |
| 6,333,051 | B1 | 12/2001 | Kabanov et al. |
| 6,597,996 | B1 | 7/2003 | Venkataraman et al. |
| 6,869,789 | B2 | 3/2005 | Liu et al. |
| 6,962,699 | B2 | 11/2005 | Pojasek et al. |
| 7,056,504 | B1 | 6/2006 | Sasisekharan et al. |
| 7,083,937 | B2 * | 8/2006 | Sasisekharan et al. ......... 435/13 |
| 7,105,334 | B2 | 9/2006 | Pojasek et al. |
| 7,110,889 | B2 | 9/2006 | Venkataraman et al. |
| 7,117,100 | B2 | 10/2006 | Venkataraman et al. |
| 7,129,335 | B2 | 10/2006 | Pojasek et al. |
| 7,139,666 | B2 | 11/2006 | Venkataraman et al. |
| 7,247,445 | B2 | 7/2007 | Sasisekharan et al. |
| 7,270,815 | B2 | 9/2007 | Sasisekharan et al. |
| 7,390,633 | B2 | 6/2008 | Liu et al. |
| 7,396,824 | B2 | 7/2008 | Sasisekharan et al. |
| 7,399,604 | B2 * | 7/2008 | Sasisekharan et al. ......... 435/13 |
| 7,412,332 | B1 | 8/2008 | Venkataraman et al. |
| 7,429,474 | B2 | 9/2008 | Sasisekharan et al. |
| 7,455,986 | B2 | 11/2008 | Liu et al. |
| 7,504,247 | B2 | 3/2009 | Sasisekharan et al. |
| 7,507,570 | B2 | 3/2009 | Prabhakar et al. |
| 7,508,206 | B2 | 3/2009 | Sasisekharan et al. |
| 7,553,950 | B2 | 6/2009 | Prabhakar et al. |
| 7,560,106 | B2 | 7/2009 | Sasisekharan et al. |
| 7,585,642 | B2 * | 9/2009 | Sasisekharan et al. ......... 435/13 |
| 7,592,152 | B2 | 9/2009 | Prabhakar et al. |
| 2002/0122793 | A1 | 9/2002 | Liu et al. |
| 2002/0128225 | A1 | 9/2002 | Liu et al. |
| 2002/0169143 | A1 | 11/2002 | Sasisekharan et al. |
| 2003/0008820 | A1 | 1/2003 | Kwan et al. |
| 2003/0099628 | A1 | 5/2003 | Liu et al. |
| 2003/0191587 | A1 | 10/2003 | Venkataraman et al. |
| 2004/0091471 | A1 | 5/2004 | Myette et al. |
| 2004/0091472 | A1 | 5/2004 | Pojasek et al. |
| 2004/0092037 | A1 | 5/2004 | Sasisekharan et al. |
| 2004/0197933 | A1 | 10/2004 | Venkataraman et al. |
| 2004/0204869 | A1 | 10/2004 | Venkataraman et al. |
| 2005/0037376 | A1 | 2/2005 | Sasisekharan et al. |
| 2005/0214276 | A9 | 9/2005 | Myette et al. |
| 2005/0215519 | A1 | 9/2005 | Viskov et al. |
| 2005/0227320 | A1 | 10/2005 | Pojasek et al. |
| 2005/0233401 | A1 | 10/2005 | Brocia |
| 2005/0233402 | A1 | 10/2005 | Liu et al. |
| 2005/0233419 | A1 | 10/2005 | Pojasek et al. |
| 2006/0024664 | A1 | 2/2006 | Sasisekharan et al. |
| 2006/0057638 | A1 | 3/2006 | Bosques et al. |
| 2006/0067927 | A1 | 3/2006 | Chandrasekaran et al. |
| 2006/0067928 | A1 | 3/2006 | Liu et al. |
| 2006/0078959 | A1 | 4/2006 | Prabhakar et al. |
| 2006/0083711 | A1 | 4/2006 | Berry et al. |
| 2006/0105430 | A1 | 5/2006 | Sasisekharan et al. |
| 2006/0127950 | A1 | 6/2006 | Bosques et al. |
| 2006/0154894 | A1 | 7/2006 | Berry et al. |
| 2006/0177885 | A1 | 8/2006 | Myette et al. |
| 2006/0177910 | A1 | 8/2006 | Myette et al. |
| 2006/0177911 | A1 | 8/2006 | Myette et al. |
| 2006/0182734 | A1 | 8/2006 | Liu et al. |
| 2006/0183713 | A1 | 8/2006 | Liu et al. |
| 2006/0183891 | A1 | 8/2006 | Myette et al. |
| 2006/0292130 | A1 | 12/2006 | Sasisekharan et al. |
| 2006/0292655 | A1 | 12/2006 | Sasisekharan et al. |
| 2006/0292673 | A1 | 12/2006 | Sasisekharan et al. |
| 2007/0004012 | A1 | 1/2007 | Sasisekharan et al. |
| 2007/0020243 | A1 | 1/2007 | Sengupta et al. |
| 2007/0065424 | A1 | 3/2007 | Pojasek et al. |
| 2007/0065921 | A1 | 3/2007 | Sasisekharan et al. |
| 2007/0066769 | A1 | 3/2007 | Venkataraman et al. |
| 2007/0148157 | A1 | 6/2007 | Prabhakar et al. |
| 2007/0148158 | A1 | 6/2007 | Sasisekharan et al. |
| 2007/0148740 | A1 | 6/2007 | Prabhakar et al. |
| 2007/0161073 | A1 | 7/2007 | Sasisekharan et al. |
| 2007/0202563 | A1 | 8/2007 | Prabhakar et al. |
| 2007/0224670 | A1 | 9/2007 | Prabhakar et al. |
| 2008/0071148 | A1 | 3/2008 | Bosques et al. |
| 2008/0278164 | A1 | 11/2008 | Sasisekharan et al. |
| 2008/0301178 | A1 | 12/2008 | Venkataraman et al. |
| 2009/0045811 | A1 | 2/2009 | Sasisekharan et al. |
| 2009/0105463 | A1 | 4/2009 | Berry et al. |
| 2009/0119027 | A1 | 5/2009 | Venkataraman et al. |
| 2009/0156477 | A1 | 6/2009 | Berry et al. |
| 2009/0269326 | A1 | 10/2009 | Myette et al. |

FOREIGN PATENT DOCUMENTS

| | | |
|---|---|---|
| EP | 0342215 A1 | 11/1989 |
| EP | 0394971 A1 | 10/1990 |
| EP | 0433225 A1 | 6/1991 |
| EP | 0557887 A2 | 9/1993 |
| FR | 2554348 A1 | 5/1985 |
| WO | WO-92/01003 A1 | 1/1992 |
| WO | WO-93/05167 A1 | 3/1993 |
| WO | WO-93/08289 A1 | 4/1993 |
| WO | WO-93/10450 A1 | 5/1993 |
| WO | WO-93/15406 A1 | 8/1993 |
| WO | WO-93/19096 A1 | 9/1993 |
| WO | WO-94/12618 A1 | 6/1994 |
| WO | WO-94/21689 A1 | 9/1994 |
| WO | WO-95/13830 A1 | 5/1995 |
| WO | WO-95/34635 A1 | 12/1995 |
| WO | WO-96/01648 A1 | 1/1996 |
| WO | WO-96/13606 A1 | 5/1996 |
| WO | WO-97/11684 A1 | 4/1997 |
| WO | WO-97/16556 A1 | 5/1997 |
| WO | WO-98/04902 A1 | 2/1998 |
| WO | WO-98/31346 A1 | 7/1998 |
| WO | WO-00/12726 A2 | 3/2000 |
| WO | WO-00/65521 A2 | 11/2000 |
| WO | WO-01/66772 A2 | 9/2001 |
| WO | WO-02/23190 A2 | 3/2002 |
| WO | WO-02/32406 A2 | 4/2002 |
| WO | WO-02/077199 A2 | 10/2002 |
| WO | WO-03/102160 A2 | 12/2003 |
| WO | WO-2004/055491 A2 | 7/2004 |
| WO | WO-2004/062592 A2 | 7/2004 |
| WO | WO-2004/069152 A2 | 8/2004 |
| WO | WO-2005/087920 A2 | 9/2005 |
| WO | WO-2005/110438 A2 | 11/2005 |
| WO | WO-2005/111627 A2 | 11/2005 |
| WO | WO-2006/076627 A2 | 7/2006 |
| WO | WO-2006/083328 A2 | 8/2006 |
| WO | WO-2006/088491 A2 | 8/2006 |
| WO | WO-2006/089206 A2 | 8/2006 |
| WO | WO-2006/105313 A2 | 10/2006 |
| WO | WO-2006/105315 A2 | 10/2006 |
| WO | WO-2007/044471 A2 | 4/2007 |
| WO | WO-2007/120478 A2 | 10/2007 |

OTHER PUBLICATIONS

Baumann et al., Three-dimensional structure of the alkaline protease of *Pseudomonas aeruginosa*: a two-domain protein with a calcium binding parallel beta roll motif. EMBO J. Sep. 1993;12(9):3357-64.

Bernstein et al., Immobilized heparin lyase system for blood deheparinization. Methods Enzymol. 1988;137:515-29.

Biemann, Four decades of structure determination by mass spectrometry: from alkaloids to heparin. J Am Soc Mass Spectrom. Nov. 2002;13(11):1254-72.

Cardin et al., Molecular modeling of protein-glycosaminoglycan interactions. Arteriosclerosis. Jan.-Feb. 1989;9(1):21-32.

Carlson et al., Behavior of antithrombin III isoforms on immobilized heparins. Evidence that the isoforms bind to different numbers of low-affinity heparin sites. J Biol Chem. Feb. 15, 1988;263(5):2187-94.

Claverie et al., Information Enhancement Methods for Large Scale Sequence Analysis. Computers Chem. 1993;17(2):191-201.

Cohen et al., The parallel beta helix of pectate lyase C: something to sneeze at. Science. Jun. 4, 1993;260(5113):1444-5.

Comfort et al., Immobilized enzyme cellulose hollow fibers: III physical properties and in vitro biocompatibility. Biotechnology and Bioengineering. 1989;34:1383-1390.

Desai et al., Mechanism of heparin activation of antithrombin.J Biol. Chem. 1998; 273(13):7478-87.

Desai et al., Specificity studies on the heparin lyases from *Flavobacterium heparinum*. Biochemistry. Aug. 17, 1993;32(32):8140-5.

Dull et al., Lung endothelial heparan sulfates mediate cationic peptide-induced barrier dysfunction: a new role for the glycocalyx. Am J Physiol Lung Cell Mol Physiol. Nov. 2003;285(5):L986-95.

Enriquez-Harris et al., Growth factors and the extracellular matrix. Trends Cell Biol. Aug. 1994;4(8):302-3.

Ernst et al., Direct evidence for a predominantly exolytic processive mechanism for depolymerization of heparin-like glycosaminoglycans by heparinase I. Proc Natl Acad Sci U S A. Apr. 14, 1998;95(8):4182-7.

Ernst et al., Enzymatic degradation of glycosaminoglycans. Crit Rev Biochem Mol Biol. 1995;30(5):387-444.

Ernst et al., Expression in *Escherichia coli*, purification and characterization of heparinase I from *Flavobacterium heparinum*. Biochem J. Apr. 15, 1996;315 ( Pt 2):589-97.

Feingold et al., Conformational aspects of the reaction mechanisms of polysaccharide lyases and epimerases. FEBS Lett. Nov. 2, 1987;223(2):207-1 1. Review.

Franklin et al., *Pseudomonas aeruginosa* AlgG is a polymer level alginate C5-mannuronan epimerase. J Bacteriol. Apr. 1994;176(7):1821-30.

Gacesa, Alginate-modifying enzymes: a proposed unified mechanism of action for the lyases and epimerases. FEBS Letters. 1987;212(2):199-202.

Gioldassi et al., Determination of phosphorylated and sulfated linkage-region oligosaccharides in chondroitin / dematan and heparan sulfate proteoglycans by high performance liquid chromatography. J Liq Chrom Rel Technol. 1999; 22(13):1997-2007.

Godavarti et al., A comparative analysis of the primary sequences and characteristics of heparinases I, II, and III from *Flavobacterium heparinum*. Biochem Biophys Res Commun. Dec. 24, 1996;229(3):770-7.

Godavarti et al., Heparinase I from *Flavobacterium heparinum*. Identification of a critical histidine residue essential for catalysis as probed by chemical modification and site-directed mutagenesis. Biochemistry. May 28, 1996;35(21):6846-52.

Godavarti et al., Heparinase I from *Flavobacterium heparinum*. Role of positive charge in enzymatic activity. J Biol Chem. Jan. 2, 1998;273(1):248-55.

Godavarti et al., Heparinase III from *Flavobacterium heparinum*: cloning and recombinant expression in *Escherichia coli*. Biochem Biophys Res Commun. Aug. 23, 1996;225(3):751-8.

Guerrini et al., A novel computational approach to integrate NMR spectroscopy and capillary electrophoresis for structure assignment of heparin and heparan sulfate oligosaccharides. Glycobiology. Nov. 2002;12(11):713-9.

Hart et al., Glycosylation. Curr Opin Cell Biol. Dec. 1992;4(6):1017-23.

Hayes, Prototeins. American Scientist, the Magazine of Sigma Xi, the Scientific Research Society. 1998;86(3):216-21.

Higuchi et al., Recombinant PCR. PCR Protocols. 1990; Academic Press Incorporated, 177.

Horner et al., Heterogeneity of rat skin heparin chains with high affinity for antithrombin. Biochem J. Jun. 15, 1987;244(3):693-8.

Huang et al., Low-molecular-weight heparins. Hematol Oncol Clin North Am. Dec. 1998;12(6):1251-81.

Jackson et al., Glycosaminoglycans: molecular properties, protein interactions, and role in physiological processes. Physiol Rev. Apr. 1991;71(2):481-539.

Jandik et al., Action pattern of polysaccharide lyases on glycosaminoglycans. Glycobiology. Jun. 1994;4(3):289-96.

Johnson et al., Endothelial cells preparing to die by apoptosis initiate a program of transcriptome and glycome regulation. FASEB J. Jan. 2004;18(1):188-90.

Juhasz et al., Mass spectrometric molecular-weight determination of highly acidic compounds of biological significance via their complexes with basic polypeptides. Proc. Natl. Acad. Sci. USA. 1994;91:4333-7.

Juhasz et al., Utility of non-covalent complexes in the matrix-assisted laser desorption ionization mass spectrometry of heparin-derived oligosaccharides. Carbohydr Res. 1995;270:131-47.

Kakkar et al., Venous thromboembolism and cancer. Baillier's Clinical Haematology. Sep. 1998;11(3):675-87.

Keiser et al., Direct isolation and sequencing of specific protein-binding glycosaminoglycans. Nat Med. Jan. 2001;7(1):123-8.

Kishibe et al., Structural requirements of heparan sulfate for the binding to the tumor-derived adhesion factor/angiomodulin that induces cord-like structures to ECV-304 human carcinoma cells. J Biol Chem. May 19, 2000;275(20)1 5321-9.

Komatsu et al., Determination of the molecular-weight distribution of low-molecular-weight heparins using high-performance gel permeation chromatography. Biol Pharm Bull. Dec. 1993;16(12):1189-93.

Kreitz et al., Controlled delivery of therapeutics from microporous membranes. II. In vitro degradation and release of heparin-loaded poly(D,L-lactide-co-glycolide). Biomaterials. Dec. 1997;18(24):1645-51.

Kretsinger et al., Structure and evolution of calcium-modulated proteins. CRC Crit Rev Biochem. 1980;8(2):1 19-74. Review.

Kreuger et al., Characterization of fibroblast growth factor 1 binding heparan sulfate domain. Glycobio. 1999;9(7):723-9.

Leckband et al., An approach for the stable immobilization of proteins. Biotechnology and Bioengineering. 1991;37:227-237.

Leckband et al., Characterization of the active site of heparinase. Abstracts of Papers Part 1: Fourth Chemical Congress of North America. 1991;202(1):a56.

Lewin, Genes V: Cells obey the laws of Physics and Chemistry. Oxford University Press, 1994. pp. 13.

Linhardt, R.J. et al., "Examination of the Substrate Specificity of Heparin and Heparan Sulfate Lyases", *Biochemistry*, 1990, pp. 2611-2617, vol. 29, No. 10, American Chemical Society.

Linhardt, R.J. et al., "Polysaccharide Lyases", *Applied Biochemistry and Biotechnology*, 1986, pp. 135-176, vol. 12.

Linhardt, R.J. et al., "Production and Chemical Processing of Low Molecular Weight Heparins", *Seminars in Thrombosis and Hemostatis*, 1999, pp. 5-16, vol. 25, Suppl. No. 3, Thiemo Medical Publishers, Inc.

Liu et al., Characterization of a heparan sulfate octasaccharide that binds to herpes simplex virus type 1 glycoprotein D. J Biol Chem. Sep. 6, 2002;277(36):33456-67. Epub Jun. 21, 2002.

Liu et al., Dynamic regulation of tumor growth and metastasis by heparan sulfate glycosaminoglycans. Semin Thromb Hemost. Feb. 2002;28(1):67-78.

Liu et al., Heparan sulfate D-glucosaminyl 3-O-sulfotransferase-3A sulfates N-unsubstituted glucosamine residues. J Biol Chem. Dec. 31, 1999 ;274(53):38155-62.

Liu et al., Strategy for the sequence analysis of heparin. Glycobiology. Dec. 1995;5(8):765-74.

Liu et al., The calcium-binding sites of heparinase I from *Flavobacterium heparinum* are essential for enzymatic activity. J Biol Chem. Feb. 12, 1999;274(7):4089-95.

Liu et al., Tumor cell surface heparan sulfate as cryptic promoters or inhibitors of tumor growth and metastasis. Proc Natl Acad Sci U S A. Jan. 22, 2002;99(2):568-73.

Lohse et al., Purification and characterization of heparin lyases from *Flavobacterium heparinum*. J Biol Chem. Dec. 5, 1992;267(34):24347-55.

Lustig et al., Alternative splicing determines the binding of platelet-derived growth factor (PDGF-AA) to glycosaminoglycans. Biochemistry. Sep. 17, 1996;35(37):12077-85.

Marciniak, Differential role of fractionated heparin in antithrombin-III proteolysis. Blood. Mar. 1982;59(3):576-81.

McLean et al., Action of heparinase II on pig mucosal heparin. Proc. of the 8th International Symposium on Glycoconjugates. 1985. Abstract 73-74.

McLean et al., Enzymic removal of 2-O-sulphato-?4,5-glycuronic acid residues from heparin oligosaccharides. Proceedings of the 7th International Symposium of Glycoconjugates. Lund, Sweden. 1983;68-9.

Myette et al., Expression in *Escherichia coli*, purification and kinetic characterization of human heparan sulfate 3-O-sulfotransferase-1. Biochem Biophys Res Commun. Feb. 1, 2002 ;290(4):1206-13.

Myette et al., Molecular cloning of the heparin/heparan sulfate delta 4,5 unsaturated glycuronidase from *Flavobacterium heparinum*, its recombinant expression in *Escherichia coli*, and biochemical determination of its unique substrate specificity. Biochemistry. Jun. 11, 2002;41(23):7424-34.

Myette et al., The heparin/heparan sulfate 2-O-sulfatase from *Flavobacterium heparinum*. Molecular cloning, recombinant expression, and biochemical characterization. J Biol Chem. Apr. 4, 2003;278(14)1 2157-66. Epub Jan. 7, 2003.

Nader et al., Heparin sequences in the heparan sulfate chains of an endothelial cell proteoglycan. Proc Natl Acad Sci U S A. Jun. 1987;84(11):3565-9.

Nesheim et al., Dependence of antithrombin III and thrombin binding stoichiometries and catalytic activity on the molecular weight of affinity-purified heparin. J Biol Chem. Mar. 5, 1986;261(7):3214-21.

Nugent, Heparin sequencing brings structure to the function of complex oligosaccharides. Proc Natl Acad Sci U S A. Sep. 12, 2000;97(19)1 0301-3.

Parthasarathy et al., Oligosaccharide sequence of human breast cancer cell heparan sulfate with high affinity for laminin. J Biol Chem. 1998;273(33):21111-4.

Petitou et al., Synthesis of thrombin-inhibiting heparin mimetics without side effects. Nature. Apr. 1, 1999 ;398(6726):417-22.

Petitou et al., Synthetic oligosaccharides having various functional domains: potent and potentially safe heparin mimetics. Bioorg Med Chem Lett. Apr. 19, 1999;9(8):1161-6.

Pixley et al., Preparation of highly stable antithrombin-sepharose and utilization for the fractionation of heparin. Thromb Res. Apr. 15, 1982;26(2):129-33.

Pojasek et al., Biochemical characterization of the chondroitinase B active site. J Biol Chem. Aug. 23, 2002;277(34):31179-86. Epub Jun. 12, 2002.

Pojasek et al., Histidine 295 and histidine 510 are crucial for the enzymatic degradation of heparan sulfate by heparinase III. Biochemistry. Apr. 11, 2000;39(14):4012-9.

Pojasek et al., Recombinant expression, purification, and kinetic characterization of chondroitinase AC and chondroitinase B from *Flavobacterium heparinum*. Biochem Biophys Res Commun. Aug. 17, 2001;286(2):343-51.

Raman et al., Identification of structural motifs and amino acids within the structure of human heparan sulfate 3-O-sulfotransferase that mediate enzymatic function. Biochem Biophys Res Commun. Feb. 1, 2002;290(4):1214-9.

Raman et al., The heparin/heparan sulfate 2-O-sulfatase from *Flavobacterium heparinum*. A structural and biochemical study of the enzyme active site and saccharide substrate specificity. J Biol Chem. Apr. 4, 2003;278(14)1 2167-74. Epub Jan. 7, 2003.

Razi et al., Structural and functional properties of heparin analogues obtained by chemical sulphation of *Escherichia coli* K5 capsular polysaccharide. Biochem J. Jul. 15, 1995;309 ( Pt 2)465-72.

Rhomberg et al., Mass spectrometric and capillary electrophoretic investigation of the enzymatic degradation of heparin-like glycosaminoglycans. Proc Natl Acad Sci U S A. Apr. 14, 1998;95(8):4176-81.

Rhomberg et al., Mass spectrometric evidence for the enzymatic mechanism of the depolymerization of heparin-like glycosaminoglycans by heparinase II. Proc Natl Acad Sci U S A. Oct. 13, 1998;95(21):12232-7.

Rhomberg et al., Mass spectrometric sequencing of heparin and heparan sulfate using partial digestion with heparinases. 45th Annual Conference of Mass Spectrometry Allied Topics. 1997;1026-7. Abstract only.

Rhomberg, Mass spectrometric and capillary electrophoretic investigation of heparin, heparinases, and related compounds. MIT (Department of Chemistry) Thesis. 1998.

Rosenberg et al., Structure-function relationships of heparin species. Proc Natl Acad Sci U S A. Jul. 1978;75(7):3065-9.

Rudd et al., Oligosaccharide sequencing technology. Nature. Jul. 10, 1997;388(6638):205-7.

Sasaki et al., Structural basis and potential role of heparin/heparan sulfate binding to the angiogenesis inhibitor endostatin. Embo J. 1999;18(22):6240-8.

Sasisekharan et al., Cloning and expression of heparinase I gene from *Flavobacterium heparinum*. Proc Natl Acad Sci U S A. Apr. 15, 1993;90(8):3660-4.

Sasisekharan et al., Heparin and heparan sulfate: biosynthesis, structure and function. Curr Opin Chem Biol. Dec. 2000;4(6):626-31.

Sasisekharan et al., Heparinase I from *Flavobacterium heparinum*. Mapping and characterization of the heparin binding domain. J Biol Chem. Feb. 9, 1996;271(6):3124-31.

Sasisekharan et al., Heparinase I from *Flavobacterium heparinum*: the role of the cysteine residue in catalysis as probed by chemical modification and site-directed mutagenesis. Biochemistry. Nov. 7, 1995;34(44):14441-8.

Sasisekharan et al., Heparinase inhibits neovascularization. Proc Natl Acad Sci U S A. Feb. 15, 1994;91(4):1524-8.

Sasisekharan et al., Roles of heparan-sulphate glycosaminoglycans in cancer. Nat Rev Cancer. Jul. 2002;2(7):521-8.

Sasisekharan, Heparinase I from *Flavobacterium heparinum*. Identification of a Critical Histidine Residue Essential for Catalysis as Probed by Chemical Modification and Site-Directed Mutagenesis. Biochemistry. 2002;35:6846-52.

Shriver et al., Biochemical investigations and mapping of the calcium-binding sites of heparinase I from *Flavobacterium heparinum*. J Biol Chem. Feb. 12, 1999;274(7):4082-8.

Shriver et al., Cleavage of the antithrombin III binding site in heparin by heparinases and its implication in the generation of low molecular weight heparin. Proc Natl Acad Sci U S A. Sep. 12, 2000;97(19):10365-70.

Shriver et al., Emerging views of heparan sulfate glycosaminoglycan structure/activity relationships modulating dynamic biological functions. Trends Cardiovasc Med. Feb. 2002;12(2):71-7.

Shriver et al., Heparinase II from *Flavobacterium heparinum*. Role of cysteine in enzymatic activity as probed by chemical modification and site- directed mutagenesis. J Biol Chem. Sep. 4, 1998;273(36):22904-12.

Shriver et al., Heparinase II from *Flavobacterium heparinum*. Role of histidine residues in enzymatic activity as probed by chemical modification and site-directed mutagenesis. J Biol Chem. Apr. 24, 1998;273(17):10160-7.

Shriver et al., Sequencing of 3-O sulfate containing heparin decasaccharides with a partial antithrombin III binding site. Proc Natl Acad Sci U S A. Sep. 12, 2000;97(19)10359-64.

Sundaram et al., Rational design of low-molecular weight heparins with improved in vivo activity. Proc Natl Acad Sci U S A. Jan. 21, 2003;100(2):651-6. Epub Jan. 13, 2003.

Sundaram, M. et al., "Rational design of low-molecular weight heparins with improved in vivo activity", *PNAS*, 100(2), 651-656, 2003.

Takahashi et al., High and Low Anticoagulant Activity Heparins: Preparation in large scale and degree of complexation with antithrombin III. Arzneim.-Forsch./Drug Res. 1985;35(11):1620-3.

Thalmann et al., Uronic acid-containing glycosaminoglycans and keratan sulfate are present in the tectorial membrane of the inner ear: functional implications. Arch Biochem Biophys. Dec. 1993;307(2):391-6.

Toida et al., Enzymatic preparation of heparin oligosaccharides containing antithrombin III binding sites. J Biol Chem. Dec. 13, 1996;271(50):32040-7.

Turnbull et al., A strategy for rapid sequencing of heparan sulfate and heparin saccharides. Proc Natl Acad Sci U S A. Mar. 16, 1999;96(6):2698-703.

Valentine et al., Low-molecular-weight heparin therapy and mortality. Semin Thromb Hemost. 1997;23(2):173-8.

Venkataraman et al., Sequencing complex polysaccharides. Science. Oct. 15, 1999;286(5439):537-42.

Volpi et al., Disaccharide analysis and molecular mass determination to microgram level of single sulfated glycosaminoglycan species in mixtures following agarose-gel electrophoresis. Anal Biochem. Sep. 10, 1999;273(2):229-39.

Volpi et al., Fast moving and "slow moving" heparins, dermatan sulfate, and chondroitin sulfate: qualitative and quantitative analysis by agarose-gel electrophoresis. Carb. Res. 1993;247:263-278.

Volpi, Inhibition of human leukocyte elastase activity by heparins: influence of charge density. Biochimica et Biophysica Acta. 1996;1290:299-307.

Wishart et al., A single mutation converts a novel phosphotyrosine binding domain into a dual-specificity phosphatase. J Biol Chem. Nov. 10, 1995;270(45):26782-5.

Witkowski et al., Conversion of a beta-ketoacyl synthase to a malonyl decarboxylase by replacement of the active-site cysteine with glutamine. Biochemistry. Sep. 7, 1999;38(36):11643-50.

Yamada et al., Structural studies on the bacterial lyase-resistant tetrasaccharides derived from the antithrombin III-binding site of porcine intestinal heparin. J Biol Chem. Mar. 5, 1993;268(7):4780-7.

Yan et al., Prime numbers and the amino acid code: analogy in coding properties. J Theor Biol. Aug. 7, 1991;151(3):333-41.

Yang et al., Purification and characterization of heparinase from *Flavobacterium heparinum*. J Biol Chem. Feb. 10, 1985;260(3)1 849-57.

Yates et al., 1H and 13C NMR spectral assignments of the major sequences of twelve systematically modified heparin derivatives. Carbohydr Res. Nov. 20, 1996;294:15-27.

Yoder et al., New domain motif: the structure of pectate lyase C, a secreted plant virulence factor. Science. 1993;260:1503-1506.

Yoder et al., Unusual structural features in the parallel beta-helix in pectate lyases. Structure. Dec. 15, 1993;1(4):241-51.

Zacharski et al., Blood coagulation activation in cancer: challenges for cancer treatment. Hamostaseologic. 1995;15:14-20.

Zhang et al., 6-O-sulfotransferase-1 represents a critical enzyme in the anticoagulant heparan sulfate biosynthetic pathway. J Biol Chem. Nov. 9, 2001;276(45):42311-21. Epub Sep. 10, 2001.

Zhao et al., Rapid, sensitive structure analysis of oligosaccharides. Proc. Natl. Acad. Sci. USA. 1997;94:1629-1633.

\* cited by examiner

METHODS FOR ANALYZING OR PROCESSING A HEPARIN SAMPLE

RELATED APPLICATIONS

This application is a continuation of U.S. patent application Ser. No. 11/606,623, filed Nov. 30, 2006 and now issued as U.S. Pat. No. 7,585,642, which is a continuation of U.S. patent application Ser. No. 11/183,323, filed Jul. 15, 2005 and now issued as U.S. Pat. No. 7,399,604, which is a divisional of U.S. patent application Ser. No. 09/951,138, filed Sep. 12, 2001 and now issued as U.S. Pat. No. 7,083,937, which claims priority under 35 U.S.C. §119 from U.S. provisional application Ser. No. 60/231,994, filed Sep. 12, 2000, the entire contents of each of which are incorporated by reference herein in their entirety.

GOVERNMENT SUPPORT

The present invention was supported in part by a grant from the United States National Institutes of Health under contract/grant number GM 57073. The U.S. Government may retain certain rights in the invention.

FIELD OF THE INVENTION

The present invention relates to methods and products associated with characterizing and using polysaccharides. In particular low molecular weight heparin products and methods of using these products are described. Methods for characterizing purity and activity of polysaccharide preparations including glycosaminoglycans such as heparin are also described.

BACKGROUND OF THE INVENTION

Coagulation is a physiological pathway involved in maintaining normal blood hemostasis in mammals. Under conditions in which a vascular injury occurs, the coagulation pathway is stimulated to form a blood clot to prevent the loss of blood. Immediately after the vascular injury occurs, blood platelets begin to aggregate at the site of injury forming a physical plug to stop the leakage. In addition, the injured vessel undergoes vasoconstriction to reduce the blood flow to the area and fibrin begins to aggregate forming an insoluble network or clot, which covers the ruptured area. When an imbalance in the coagulation pathway shifts towards excessive coagulation, the result is the development of thrombotic tendencies, which are often manifested as heart attacks, strokes, deep vein thrombosis, and myocardial infarcts. Current therapies for treating disorders associated with imbalances in the coagulation pathway involve many risks and must be carefully controlled.

Heparin, a highly sulphated heparin-like glycosaminoglycan (HLGAG) produced by mast cells, is a widely used clinical anticoagulant, and is one of the first biopolymeric drugs and one of the few carbohydrate drugs. Heparin primarily elicits its effect through two mechanisms, both of which involve binding of antithrombin III (AT-III) to a specific pentasaccharide sequence, $H_{NAc/S,6S}GH_{NS,3S,6S}I_{2S}H_{NS,6S}$ contained within the polymer. First, AT-III binding to the pentasaccharide induces a conformational change in the protein that mediates its inhibition of factor Xa. Second, thrombin (factor IIa) also binds to heparin at a site proximate to the pentasaccharide AT-III binding site. Formation of a ternary complex between AT-III, thrombin and heparin results in inactivation of thrombin. Unlike its anti-Xa activity that requires only the AT-III pentasaccharide-binding site, heparin's anti-IIa activity is size-dependant, requiring at least 18 saccharide units for the efficient formation of an AT-III, thrombin, and heparin ternary complex.

In addition to heparin's anticoagulant properties, its complexity and wide distribution in mammals have lead to the suggestion that it may also be involved in a wide range of additional biological activities. Heparin-like glycosaminoglycans (HLGAGs), present both at the cell surface and in the extracellular matrix, are a group of complex polysaccharides that are variable in length, consisting of a disaccharide repeat unit composed of glucosamine and an uronic acid (either iduronic or glucuronic acid). The high degree of complexity for HLGAGs arises not only from their polydispersity and the possibility of two different uronic acid components, but also from differential modification at four positions of the disaccharide unit. Three positions, viz., C2 of the uronic acid and the C3, C6 positions of the glucosamine can be O-sulfated. In addition, C2 of the glucosamine can be N-acetylated or N-sulfated. Together, these modifications could theoretically lead to 32 possible disaccharide units, making HLGAGs potentially more information dense than either DNA (4 bases) or proteins (20 amino acids). This enormity of possible structural variants allows HLGAGs to be involved in a large number of diverse biological processes, including angiogenesis (Sasisekharan, R., Moses, M. A., Nugent, M. A., Cooney, C. L. & Langer, R. (1994) *Proc Natl Acad Sci USA* 91, 1524-8), embryogenesis (Binari, R. C., Staveley, B. E., Johnson, W. A., Godavarti, R., Sasisekharan, R. & Manoukian, A. S. (1997) *Development* 124, 2623-32; Tsuda, M., Kamimura, K., Nakato, H., Archer, M., Staatz, W., Fox, B., Humphrey, M., Olson, S., Futch, T., Kaluza, V., Siegfried, E., Stam, L. & Selleck, S. B. (1999) *Nature* 400, 276-80; and Lin, X., Buff, E. M., Perrimon, N. & Michelson, A. M. (1999) *Development* 126, 3715-23) and the formation of β-fibrils in Alzheimer's disease (McLaurin, J., Franklin, T., Zhang, X., Deng, J. & Fraser, P. E. (1999) *Eur J Biochem* 266, 1101-10. And Lindahl, B., Westling, C., Gimenez-Gallego, G., Lindahl, U. & Salmivirta, M. (1999) *J Biol Chem* 274, 30631-5).

Although heparin is highly efficacious in a variety of clinical situations and has the potential to be used in many others, the side effects associated with heparin therapy are many and varied. Side effects such as heparin-induced thrombocytopenia (HIT) are primarily associated with the long chain of un-fractionated heparin (UFH), which provides binding domains for various proteins. This has lead to the explosion in the generation and utilisation of low molecular weight heparin (LMWH) as an efficacious alternative to UFH. Although attention has been focused on LMWH as heparin substitutes due to their more predictable pharmacological action, reduced side effects, sustained antithrombotic activity, and better bioavailability, there is at present limited ability to Standardize the LMWH manufacturing process. Because the LMWH are derived from heparins and hence are polydisperse and microheterogenous, with undefined structure, they possess inherent variability, which currently prevents an efficient process for their manufacture. It would be of value both medically and scientifically to have a consistent, quality controlled, time efficient, concentration independent, and highly reproducible method for producing heparin and other glycosaminoglycans.

In an attempt to characterize the molecular, structural, and activity variations of heparin, several techniques have been investigated for the analysis of heparin preparations. Gradient polyacrylamide gel electrophoresis (PAGE) and strong ion exchange HPLC (SAX) have been used for the qualitative and quantitative analysis of heparin preparations. Although the gradient PAGE method can be useful in determining molecular weight, it suffers from the lack of resolution, particularly the lack of resolution of different oligosaccharides having identical size. SAX-HPLC, which relies on detection by ultraviolet absorbance, is often insufficiently sensitive for detecting small amounts of structurally important heparin-derived oligosaccharides. The current technologies for purifying and analyzing heparins and other glycosaminoglycans are insufficient. There is a great clinical and scientific need for improved isolation and analysis methods.

SUMMARY OF THE INVENTION

The invention relates in some aspects to methods for characterizing polysaccharide preparations. As a result of the complex saccharide structures, it has been difficult if not impossible to characterize the purity and/or activity of polysaccharide preparations. Unlike nucleic acid and protein samples, polysaccharide preparations are generally characterized based on their ability to produce a certain level of activity in a biological sample. These assays do not achieve the level of accuracy that can be achieved by direct structural characterization. According to some aspects of the invention a method of analyzing and characterizing a polysaccharide sample is provided. The method involves applying an experimental constraint to a polysaccharide in a sample to produce a modified polysaccharide having a signature component, detecting the presence of the signature component in the sample as an indication that the polysaccharide is present in the sample, and determining the presence or absence of the signature component to analyze the sample. In some embodiments the signature component has a known biological activity and in other embodiments the signature component is biologically inactive.

The experimental constraint applied to the sample is any type of manipulation that results in the identification of the presence or absence of the signature component. The experimental constraint may, for example, be any one alone or combination of the following types of experimental constraints: capillary electrophoresis, high pressure liquid chromatography, gel permeation chromatography, nuclear magnetic resonance, modification with an enzyme such as digestion with an exoenzyme or an endoenzyme, chemical digestion, or chemical modification.

The signature component can be used to provide information about the sample. Some of the uses depend on whether the signature component is an active or inactive biological component. For instance, in some cases when the signature component is an active biological component and the sample is a batch of polysaccharide, the signature component may be used to monitor the purity of the batch by determining the amount of signature component in the batch. In other embodiments the method of analysis is a method for monitoring the presence of active components in the sample, wherein the presence of the signature component in the sample is indicative of an active component in the sample. In other embodiments the method of analysis is a method for determining the amount of active components in the sample by determining the amount of signature component in the sample. The method may also be performed on at least two samples such that the relative amounts of signature component in each of the at least two samples is determined, and the highest relative level of signature component is indicative of the most active sample.

In some instances when the signature component is an inactive biological component, the method of analysis may be a method for monitoring the presence of active components in the sample, wherein the presence of the signature component in the sample is indicative of a sample lacking an active component.

The methods are also useful in some embodiments for identifying biologically active molecules. For instance, the signature component may be used to screen a library.

Thus in some embodiments the signature component is a biologically active portion of a polysaccharide. Biologically active portions of polysaccharides include but are not limited to a tetrasaccharide of the AT-III biding domain of heparin, a tetrasaccharide of the FGF biding domain of heparin, $\Delta UH_{NAC,6S}GH_{NS,3S,6S}$; $\Delta UH_{NS,6S}GH_{NS,3S,6S}$; $\Delta UH_{NAC,6S}GH_{NS,3S}$; and $\Delta UH_{NS,6S}GH_{NS,3S}$.

The polysaccharide in some embodiments is a glycosaminoglycan, such as a low molecular weight heparin (LMWH), heparin, a biotechnologically prepared heparin, a chemically modified heparin, a synthetic heparin, and a heparan sulfate.

In another embodiment the polysaccharide in the sample is compared to a reference database of polysaccharides of identical size as the polysaccharide, wherein the polysaccharides of the reference database have also been subjected to the same experimental constraints as the polysaccharide in the sample, wherein the comparison provides a compositional analysis of the sample polysaccharide.

In some preferred embodiments the sample is a pharmaceutical product. In other embodiments the sample is biological sample, such as a blood sample.

A method for evaluating the quality of a polysaccharide sample is provided according to other aspects of the invention. The method involves identifying a component within the polysaccharide sample, determining a quantitative value of the amount of component, wherein the quantitative value of the component is indicative of the quality of the polysaccharide sample. In one embodiment the method involves identifying at least two components within the polysaccharide sample and determining a quantitative value of the amount of each of the at least two components to evaluate the quality of the polysaccharide sample.

The quantitative value may be calculated by a variety of different methods, depending on how the sample is processed to identify the component. For instance, the quantitative value may be calculated as the area under the curve when the sample is processed by capillary electrophoresis, as the response factor, or as the percent relative amount of each fraction present in the sample.

In one embodiment the step of calculating the percent relative amount of each fraction present in the sample is determined according to the below equation:

$$PRA = RF \times AUC_{\%R}.$$

wherein
PRA=percent relative amount of each fraction
RF=response factor
$AUC_{\%R}$=percent relative AUC $[(100 \times AUC_C/AUC_T)]$
$AUC_C$=Area under the curve for one component
$AUC_T$=the sum of the Area under the curve for all components.

In another embodiment computer-implemented method for generating a data structure, tangibly embodied in a computer-readable medium, representing a quantitative value of a component of a polysaccharide, the method comprising an act of performing the above calculation.

In one embodiment the component is signature component $\Delta UH_{NAC,6S}GH_{NS,3S,6S}$, $\Delta UH_{NS,6S}GH_{NS,3S,6S}$; $\Delta UH_{NAC,6S}GH_{NS,3S}$; or $\Delta UH_{NS,6S}GH_{NS,3S}$.

In another aspect the invention relates to a method of producing a composition of glycosaminoglycans. The method involves performing a salt precipitation of a glycosaminoglycan containing sample in a solvent to produce a first higher molecular weight fraction, and a second fraction of isolated LMWH, and processing the second fraction of isolated LMWH to produce a concentrated LMWH preparation. In a preferred embodiment the salt used in the precipitation step is a salt of divalent cations and weak anions. The prior art generally taught that when a method for isolating heparin using a salt precipitation is used, the first fraction should be processed to generate LMWH and the second fraction should be discarded. It has been discovered that the second fraction actually contains a preferred source of biologically active LMWH.

In some embodiments the salt of the divalent cations and weak anions is selected from among the group comprising; barium, calcium, magnesium, strontium, copper, nickel, cadmium, zinc., mercury, beryllium, nickel, palladium, platinum, iron, and tin. In other embodiments the salt of divalent cations and weak anions are acetates of cations of elements of the periodic table having divalent valence.

The components of the LMWH fraction can be further altered by manipulating the temperature and type of solvent used in the precipitation. For instance, in one embodiment the precipitation may be performed at a temperature in a range of 0° C. to 70° C. In other embodiments the temperature of the mixture is 70° C., 60° C., 50° C., 40° C., 30° C. 25° C., 20° C., 15° C., 10° C., 5° C., 3° C., 2° C., 1° C., or 0° C. In yet other embodiments the precipitation is performed at a temperature of 4° C. Preferably the solvent is a polar solvent. Polar solvents include but are not limited to $H_2O$, $H_2O$ mixed with ethanol, $H_2O$ mixed with acetone, or a combination of $H_2O$, ethanol, and acetone. In some embodiments the polar solvent used in the precipitation has a volume to volume $H_2O$:ethanol ratio in the range of 99:1, 95:5, 90:10, 85:15, 80:20, 75:25, 65:35, 55:45, 50:50, 45:55, 35:65, 25:75, 20:80, 15:85, 10:90, 5:95, or 1:99. In other embodiments the polar solvent used in the precipitation has a volume to volume $H_2O$:acetone ratio in the range of 99:1, 95:5, 90:10, 85:15, 80:20, 75:25, 65:35, 55:45, 50:50, 45:55, 35:65, 25:75, 20:80, 15:85, 10:90, 5:95, or 1:99. In one embodiment the polar solvent is a mixture of $H_2O$, ethanol, and acetone.

The step of processing of the second fraction to yield the concentrated LMWH preparation, in one embodiment, is an enzymatic digestion, such as digestion with Heparinase III. In other embodiments, the processing of the second fraction to yield the concentrated LMWH preparation is chemical degradation. In some embodiments the method of chemical degradation is selected from the group including oxidative depolymerization with $H_2O_2$ or $CU^+$ and $H_2O_2$, deaminative cleavage with isoamyl nitrite, or nitrous acid, β-eliminative cleavage with benzyl ester of heparin by alkaline treatment or by heparinase. The processing of the second fraction to yield the concentrated LMWH preparation in other embodiments is a purification step to produce a purified LMWH preparation. The method may involve the further step of formulating the purified LMWH preparation in a pharmaceutical carrier.

In other embodiments the glycosaminoglycan is selected from the group consisting of heparin, heparin analogs, LMWH, biotechnological heparin, chemically modified heparin, or synthetic heparin.

Compositions comprising a LMWH preparation having an anti-Xa activity of at least 150 IU/mg and/or LMWH preparation having an anti-factor Xa:anti-factor IIa activity ratio of greater than 5 are provided according to other aspects of the invention. In some embodiments the LMWH preparation is isolated and in other embodiments it is synthetic. In some embodiments the LMWH preparation having an anti-Xa activity of at least 150 IU/mg has an anti-factor Xa:anti-factor IIa activity ratio of at least 1, 2, 3, 4, 5, 6, 7, 8, 9, or 10.

In other aspects the composition is a LMWH preparation having at least 15% disulfated disaccharides, less than 75% trisulfated disaccharides, 3-5% monosulfated disaccharides, and at least 2% 4-7 tetrasaccharide.

The composition may be formulated for therapeutic delivery to a subject by methods such as subcutaneous delivery, intravenous delivery, aerosol delivery, or oral delivery.

In some embodiments the LMWH preparation includes at least 3.5%, 4.0%, or 5.0% $\Delta UH_{NAC,6S}GH_{NS,3S,6S}$, $\Delta UH_{NS,6S}GH_{NS,3S,6S}$; $\Delta UH_{NAC,6S}GH_{NS,3S}$; or $\Delta UH_{NS,6S}GH_{NS,3S}$.

A method for treating a subject having a condition is provided according to other aspects of the invention. The method involves selecting a composition of LMWH having an identified level of AT-binding sequence, the level of AT-binding sequence selected depending on the condition to be treated in the subject, and administering to a subject an effective amount of the composition of LMWH having an identified level of AT-binding sequence.

The subject, in some embodiments, has or is at risk of developing venous or arterial thromboembolic disease. The LMWH preparation administered to these subjects may include at least 3.5%, 4.0%, or 5.0% $\Delta UH_{NAC,6S}GH_{NS,3S,6S}$, $\Delta UH_{NS,6S}GH_{NS,3S,6S}$; $\Delta UH_{NAC,6S}GH_{NS,3S}$; or $\Delta UH_{NS,6S}GH_{NS,3S}$. In other embodiments the composition of LMWH is a LMWH preparation having an anti-Xa activity of at least 150 IU/mg. In yet other embodiments the composition of LMWH is a LMWH preparation having an anti-factor Xa:anti-factor IIa activity ratio of greater than 5.

The invention in other aspects includes a composition, comprising, a LMWH preparation prepared by a process comprising: obtaining a heparin preparation, and performing an exhaustive digestion of the heparin preparation using heparinase I, heparinase II, and heparinase III.

In other aspects the invention relates to a kit for analyzing a polysaccharide sample including a control composition for identifying a signature component of a polysaccharide, and instructions for applying an experimental constraint to a polysaccharide sample to produce a modified polysaccharide having a signature component characteristic of the polysaccharide and for comparing the modified polysaccharide to the control composition to identify the presence or absence of the signature component. In some embodiments the kit also includes a composition for applying an experimental constraint to the polysaccharide sample, such as, for example, an exoenzyme or an endoenzyme. In yet other embodiments the instructions include the steps for quantifying the signature component of the polysaccharide in the sample.

Each of the limitations of the invention can encompass various embodiments of the invention. It is, therefore, anticipated that each of the limitations of the invention involving any one element or combinations of elements can be included in each aspect of the invention.

DETAILED DESCRIPTION

Figure 1:
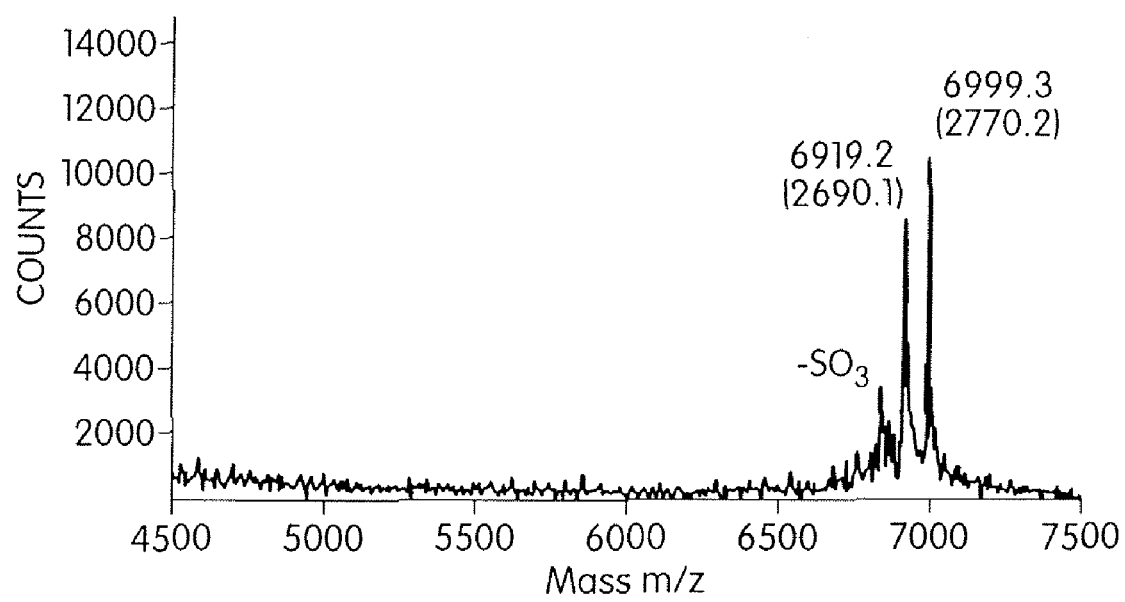
FIG. 1 is a MALDI mass spectrum of the protonated complex of AT-10 with $(RG)_{19}R$.

The invention involves several discoveries that have led to new advances in the field of polysaccharide biology. One of the major problems in characterizing polysaccharides results from their structural diversity. This structural diversity is one of the factors that has made it difficult to study sequence-function relationships for polysaccharides. Chemical synthesis of defined oligosaccharides has been used in studying the relative contribution to biological activities, such as the high affinity AT-III binding of specific modifications in the pentasaccharide sequence of heparin (Desai, U. R., Petitou, M., Bjork, I. & Olson, S. T. (1998) *J Biol Chem* 273, 7478-87). However, such synthetic methods are complex and have not been widely applied to the study of other biological sequences. An alternative approach involving affinity fractionation of polysaccharide with proteins of interest and subsequent characterisation has provided some overall information regarding sulfation patterns of polysaccharides that determine affinity (Parthasarathy, N., Gotow, L. F., Bottoms, J. D., Kute, T. E., Wagner, W. D. & Mulloy, B. (1998) *J Biol Chem* 273, 21111-4; Sasaki, T., Larsson, H., Kreuger, J., Salmivirta, M., Claesson-Welsh, L., Lindahl, U., Hohenester, E. & Timpl, R. (1999) *Embo J* 18, 6240-8; and Kreuger, J., Prydz, K., Pettersson, R. F., Lindahl, U. & Salmivirta, M. (1999) *Glycobiology* 9, 723-9).

The invention is based, in one aspect, on a new method for characterising samples of polysaccharides. It has been discovered that polysaccharide sequences can be rapidly and accurately sequenced to identify a signature component of the polysaccharide. The signature component can be used to characterize the polysaccharide sample in ways that were not previously possible. The analysis of pharmaceutical-grade polysaccharides is governed by the United States Pharmacopia (USP) and other national pharmacopia. Generally, the types of analysis required for polysaccharides are functional assays and in some cases very general structural assays. The assays that are currently being used to determine the activity/purity of a commercially available heparin preparation are an in vitro coagulation assay and a test for bacterial endotoxins. The amount of heparin is determined to be that amount that will cause 1 ml of sheep plasma to half-clot when kept for 1 hour at 20° C. compared to a USP reference standard (defined as units/ml) or the Fifth International standard for Unfractionated Heparin (WHO-5) (defined as International Units/ml).

(Linhardt, R. J. & Gunay, N. S. (1999) *Semin Thromb Hemost* 25, 5-16). Compared with the strict regulatory requirements for other (non-polysaccharide) drugs these characterization standards are out of date.

The methods of the invention provide a much more accurate way for characterizing these samples. The methods involve manipulating a polysaccharide containing sample to identify the presence or absence of a signature component. The amount of signature component present in the sample can be determined. The quantity of signature component gives an accurate characterization of the sample.

Thus, in some aspects, the invention is a method of analyzing a sample by applying an experimental constraint to a polysaccharide in a sample, to produce a modified polysaccharide, having a signature component, detecting the presence of the signature component, in the sample as an indication that the polysaccharide is present in the sample, and determining the presence or absence of the signature component to analyze the sample.

A "polysaccharide" is a polymer composed of monosaccharides linked to one another. In many polysaccharides the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide).

The methods for characterizing polysaccharide samples were developed based on experimental analysis of heparin-like glycosaminoglycans (HLGAGs) but the properties taught herein can be extended to other polysaccharides. The methods of the invention will be discussed with respect to HLGAGs as an example, but the methods are not limited to HLGAGs. Thus in one embodiment the polysaccharide sample to be analysed includes HLGAGs or glycosaminoglycans. As used herein the terms "HLGAG" and "glycosaminoglycans" are used interchangeably to refer to a family of molecules having heparin like structures and properties. These molecules include but are not limited to low molecular weight heparin (LMWH), heparin, biotechnologically prepared heparin, chemically modified heparin, synthetic heparin, and heparan sulfate. The term "biotechnological heparin" encompasses heparin that is prepared from natural sources of polysaccharides which have been chemically modified and is described in Razi et al., Bioche. J. 1995 Jul. 15; 309 (Pt 2): 465-72. Chemically modified heparin is described in Yates et al., Carbohydrate Res (1996) Nov. 20; 294:15-27, and is known to those of skill in the art. Synthetic heparin is well known to those of skill in the art and is described in Petitou, M. et al., Bioorg Med Chem Lett. (1999) Apr. 19; 9(8):1161-6.

As shown in the Examples below the sequence of an AT-III fractionated decasaccharide (AT-10), which may be used as a signature component of HLGAGs, has been identified using a property-encoded nomenclature/mass spectrometry scheme (PEN-MALDI), a sequencing methodology described in U.S. patent application Ser. Nos. 09/557,997 and 09/558,137 filed on Apr. 24, 2000, having common inventorship, and Venkataraman, G., Shriver, Z., Raman, R. & Sasisekharan, R. (1999) *Science* 286, 537-42. Integral Glycan Sequencing (IGS) (Turnbull, J. E., Hopwood, J. J. & Gallagher, J. T. (1999) *Proc Natl Acad Sci USA* 96, 2698-703) and proton nuclear magnetic resonance ($^1$H NMR) analysis of the decasaccharide are consistent with the results of PEN-MALDI. The flexibility of this sequencing strategy is also demonstrated by the fact that we can derive sequence information for contaminating oligosaccharides, if present. Sequencing of a chemically complex AT-III fractionated saccharide (including the rare 3-O-sulfation of glucosamine) established a methodology that can be extended to the analysis of other HLGAG oligosaccharides of interest, for example those HLGAGs with growth factor binding properties. A straight-forward sequencing methodology for these types of sequences has enabled structure-function studies of this important class of molecules.

HLGAGs and other polysaccharides all have signature components. A "signature component" is an oligosaccharide which is present in and characteristic of a particular polysaccharide. The properties of the signature selected for may depend on the type of polysaccharide being studied and the type of experimental constraint applied to the polysaccharide. The signature is a reproducible element of a particular polysaccharide being manipulated with a particular experimental constraint. For instance, some signatures of the HLGAGs which have been identified and demonstrated to be useful are $\Delta UH_{NAC,6S}GH_{NS,3S,6S}$, $\Delta UH_{NS,6S}GH_{NS,3S,6S}$; $\Delta UH_{NAC,6S}GH_{NS,3S}$; or $\Delta UH_{NS,6S}GH_{NS,3S}$. When an HLGAG containing sample is subjected to capillary electrophoresis following heparinase treatment this signature will be identified and is capable of being quantitated.

The signature component may be biologically active or inactive. Important information can be derived from the signature component whether it is an active component or an inactive component. A signature which has biological activity is an oligosaccharide that is known to produce a specific biological function. For instance the tetrasaccharides $\Delta UH_{NAC,6S}GH_{NS,3S,6S}$, $\Delta UH_{NS,6S}GH_{NS,3S,6S}$; $\Delta UH_{NAC,6S}GH_{NS,3S}$; or $\Delta UH_{NS,6S}GH_{NS,3S}$ of HLGAGs are known to be part of the sequences possessing anti-coagulant activity resulting in the inhibition of factor Xa. Thus the presence of this component in a sample is directly indicative of the anti-coagulant activity of the HLGAG.

Signatures that have biological activity can be used for a variety of purposes. For instance, these types of signatures are useful for monitoring batch-to-batch variability of a polysaccharide preparation. The purity of each batch may be determined by determining the amount of active signature component in the batch. These signatures are also useful for monitoring the presence of active components in the sample, when the presence of the signature component in the sample is indicative of an active component in the sample. For instance, the signature component may be used to follow the active component through a processing procedure. Using this method one can test the products after each separation step to determine which fraction contains the biologically active component. The amount of active components in the sample can also be quantified by determining the amount of signature component in the sample.

The methods may also be performed on at least two samples to determine which sample has the most activity or to otherwise compare the purity of the samples. In this case the relative amounts of signature component in each of the at least two samples is determined. The highest relative level of signature component is indicative of the most active sample.

Additionally, the active signature can be used to identify biologically active molecules by screening compounds or libraries of compounds. Libraries include, for instance, phage display libraries, combinatorial libraries, libraries of peptoids and non-peptide synthetic moieties. Phage display can be particularly effective in identifying peptides which interact with the signature components, including human antibodies. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the signature component. This process can be repeated through several cycles of reselection of phage that bind to the signature component. Repeated rounds lead to enrichment of phage bearing particular sequences. DNA sequence analysis can be conducted to identify the sequences of the expressed polypeptides. The minimal linear portion of the sequence that binds to the signature component can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the signature component. Peptide and non-peptide libraries which are based on a known signature component can easily be generated by those of skill in the art. Commercial entities such as ArQule (Woburn, Mass.) prepare custom libraries for the generation of mimetic compounds.

Examples of biologically active portions of a polysaccharide include but are not limited to a tetrasaccharide of the AT-III biding domain of heparin, a tetrasaccharide of the FGF biding domain of heparin, $\Delta UH_{NAC,6S}GH_{NS,3S,6S}$, $\Delta UH_{NS,6S}GH_{NS,3S,6S}$, $\Delta UH_{NAC,6S}GH_{NS,3S}$, or $\Delta UH_{NS,6S}GH_{NS,3S}$.

Signatures that are biologically inactive are oligosaccharides that are not associated with a specific known biological function. These oligosaccharides may have some biological function but not the specific function being analyzed. For instance, the oligosaccharide may actually cause an inhibition of tumor cell growth, but not have any effect on the coagulation cascade. If the polysaccharide sample is being evaluated for the purpose of identifying the presence or amount of polysaccharides which are useful for anti-coagulation purposes, the oligosaccharide being detected is considered to be a biologically inactive signature. If, on the other hand, the polysaccharide sample is being evaluated for the purpose of identifying the presence or amount of polysaccharides which are useful for preventing tumor cell proliferation, the oligosaccharide being detected is considered to be a biologically active signature.

Signatures that are biologically inactive can be used for some of the same purposes as biologically active signatures, as well as other purposes. Biologically inactive signatures can also be used to monitor batch to batch variability of a polysaccharide preparation. Since two batches are being compared to one another, both inactive and active signatures can be used. Inactive signature components can also be used for monitoring the presence of active components in the sample when the presence of the signature component in the sample is indicative of a sample lacking a specific activity or having lower levels of this activity. Thus, if the presence of an inactive signature component is inversely proportional to the presence of an active component, then the presence of the inactive component can provide important information about the activity of the sample. For instance if the inactive signature component is a degradation product of an active component of a polysaccharide, then the presence of the inactive component indicates that some of the active component has been broken down and thus the sample is less active than it would be if the inactive component were not present.

An "experimental constraint" as used herein is a biochemical process performed on a polysaccharide sample which results in a modification of the sample to allow the signature to be detected. Experimental constraints include but are not limited to separation methods, e.g., mass spectrometry, capillary electrophoresis, high pressure liquid chromatography (HPLC), gel permeation chromatography, nuclear magnetic resonance; enzymatic digestion, e.g., with an exoenzyme, an endoenzyme; chemical digestion; chemical modification; chemical peeling (i.e., removal of a monosaccharide unit); and enzymatic modification, for instance sulfation at a particular position with a heparan sulfate sulfotransferases.

The signature can be identified by any means which is consistent with the experimental constraint used. Molecular weight of a signature component, for instance, may be determined by several methods including mass spectrometry. The use of mass spectrometry for determining the molecular weight of polysaccharides is well known in the art. Mass Spectrometry has been used as a powerful tool to characterize polysaccharides because of its accuracy (±1 Dalton) in reporting the masses of fragments generated (e.g., by enzymatic cleavage), and also because only pM sample concentrations are required. For example, matrix-assisted laser desorption ionization mass spectrometry (MALDI-MS) has been described for identifying the molecular weight of polysaccharide fragments in publications such as Rhomberg, A. J. et al, *PNAS, USA*, v. 95, p. 4176-4181 (1998); Rhomberg, A. J. et al, *PNAS, USA*, v. 95, p. 12232-12237 (1998); and Ernst, S. et. al., *PNAS, USA*, v. 95, p. 4182-4187 (1998), each of which is hereby incorporated by reference. Other types of mass spectrometry known in the art, such as, electron spray-MS, fast atom bombardment mass spectrometry (FAB-MS) and collision-activated dissociation mass spectrometry (CAD) can also be used to identify the molecular weight of the polysaccharide fragments.

The mass spectrometry data may be a valuable tool to ascertain information about the polysaccharide signature component alone or after the polysaccharide has undergone degradation with enzymes or chemicals. After a molecular weight of a polysaccharide is identified, it may be compared to molecular weights of other known polysaccharides (e.g., using the methods of U.S. patent application Ser. Nos. 09/557,997 and 09/558,137 filed on Apr. 24, 2000). As shown in these patent applications, one technique for comparing molecular weights is to generate a mass line and compare the molecular weight of the unknown polysaccharide to the mass line to determine a subpopulation of polysaccharides which have the same molecular weight. A "mass line" is an information database, preferably in the form of a graph or chart which stores information for each possible type of polysaccharide having a unique sequence based on the molecular weight of the polysaccharide. Because mass spectrometry data indicates the mass of a fragment to 1 Da accuracy, a length may be assigned uniquely to a fragment by looking up a mass on the mass line. Further, it may be determined from the mass line that, within a fragment of a particular length higher than a disaccharide, there is a minimum of 4.02 Da different in masses indicating that two acetate groups (84.08 Da) replaced a sulfate group (80.06 Da). Therefore, a number of sulfates and acetates of a polysaccharide fragment may be determined from the mass from the mass spectrometry data and, such number may be assigned to the polysaccharide fragment.

In addition to molecular weight, other properties of a signature component may be determined. The compositional ratios of substituents or chemical units (quantity and type of total substituents or chemical units) may be determined using methodology known in the art, such as capillary electrophoresis. A polysaccharide may be subjected to a first experimental constraint such as enzymatic or chemical degradation to separate the polysaccharide into smaller fragments. These fragments then may be subjected to a second experimental constraint, that is, they may be separated using capillary electrophoresis to determine the quantity and type of substituents or chemical units present in the polysaccharide. Alternatively the polysaccharide may be subjected to a single experimental constraint such as capillary electrophoreses, without prior enzymatic degradation.

In the method of capillary gel-electrophoresis, reaction samples may be analyzed by small-diameter, gel-filled capillaries. The small diameter of the capillaries (50 μm) allows for efficient dissipation of heat generated during electrophoresis. Thus, high field strengths can be used without excessive Joule heating (400 V/m), lowering the separation time to about 20 minutes per reaction run, therefor increasing resolution over conventional gel electrophoresis. Additionally, many capillaries may be analyzed in parallel, allowing amplification of generated polysaccharide information.

Other methods for assessing the signature component may also be utilized. For instance, other methods include methods which rely on parameters such as viscosity (Jandik, K. A., Gu, K. and Linhardt, R. J., (1994), *Glycobiology,* 4:284-296) or total UV absorbance (Ernst, S. et al., (1996), *Biochem. J.,* 315:589-597).

HLGAG fragments may be degraded using enzymes such as heparin lyase enzymes (heparinases) or nitrous acid and they may also be modified using different enzymes that transfer sulfate groups to the positions mentioned earlier or remove the sulfate groups from those positions. The modifying enzymes are exolytic and non-processive which means that they just act once on the non reducing end and will let go of the heparin chain without sequentially modifying the rest of the chain. For each of the modifiable positions in the disaccharide unit there exits a modifying enzyme. An enzyme that adds a sulfate group is called a sulfotransferase and an enzyme that removes a sulfate group is called a sulfatase. The modifying enzymes include 2-O sulfatase/sulfotransferase, 3-O sulfatase/sulfotransferase, 6-O sulfatase/sulfotransferase and N-deacetylase-N-sulfotransferase. The function of these enzymes is evident from their names, for example a 2-O sulfotransferase transfers a sulfate group to the 2-O position of an iduronic acid (2-O sulfated glucuronic acid is a rare occurrence in the HLGAG chains) and a 2-O sulfatase removes the sulfate group from the 2-O position of an iduronic acid.

HLGAG degrading enzymes include but are not limited to heparinase-I, heparinase-II, heparinase-III, D-glucuronidase and L-iduronidase, modified version so f heparinases, variants and functionally active fragments thereof. The three heparinases from *Flavobacterium heparinum* are enzymatic tools that have been used for the generation of LMWH (5,000-8,000 Da) and ultra-low molecular weight heparin (~3,000 Da). Heparinase I cleaves highly sulfated regions of HLGAGs at 2-O sulfated uronic acids, whereas heparinase II has a broader substrate specificity and cleaves glycosidic linkages containing both 2-O sulfated and nonsulfated uronic acids (Ernst, S., Langer, R., Cooney, C. L. & Sasisekharan, R. (1995) *Crit Rev Biochem Mol Biol* 30, 387-444). Heparinase III, as opposed to heparinase I, cleaves primarily undersulfated regions of HLGAGs, viz., glycosidic linkages containing a nonsulfated uronic acid (Ernst, S., Langer, R., Cooney, C. L. & Sasisekharan, R. (1995) *Crit Rev Biochem Mol Biol* 30, 387-444). Multiple investigations into the substrate specificity of the heparinases has increased their usefulness as tools to develop structure-function relationships for HLGAGs. Several patents and patent applications describe useful modifications and variants and fragments of heparinase, including U.S. Pat. No. 6,217,863 B1 and pending application Ser. Nos. 09/384,959 and 09/802,285. Other modifications and variants are also useful. A more detailed understanding is required to maximize their usefulness as generators of pharmacological LMWH. The discoveries of the invention provide some more of this detail (as described below).

Glucuronidase and iduronidase, as their name suggests, cleave at the glycosidic linkage after a glucuronic acid and iduronic acid respectively. Nitrous acid clips randomly at glycosidic linkages after a N-sulfated hexosamine and converts the six membered hexosamine ring to a 5-membered anhydromannitol ring.

The methods for analysing polysaccharides by identifying the presence of a signature component may be used to provide a qualitative assessment of the polysaccharide (e.g., whether the signature component is present or absent) or a quantitative assessment (e.g., the amount of signature component present to indicate sample quality such as activity, purity or simply to compare different samples). The method in some aspects is performed by identifying a component within the polysaccharide sample and determining a quantitative value of the amount of component. In some embodiments the method involves identifying and quantifying at least two components.

The quantitative value may be calculated by any means, such as, by determining the area under the curve (AUC) when the sample is processed by capillary electrophoresis, the response factor (RF), or the percent relative amount of each fraction present in the sample. Methods for making these types of calculations are described below in detail in the Examples section. Briefly, the AUC can be calculated directly from a CE spectrum. The response factor is that amount of signature that gives the same response as a control oligosaccharide. The RF can be calculated, for example, in terms of absorbance and compared with the absorbance of a control sample. The percent relative amount of each fraction present in the sample may be determined according to the following equation:

$$PRA = RF \times AUC_{\% R}$$

wherein
PRA=percent relative amount of each fraction
RF=response factor
$AUC_{\% R}$=percent relative AUC $[(100 \times AUC_C)/AUC_T)]$
$AUC_C$=Area under the curve for one component
$AUC_T$ the sum of the Area under the curve for all components.

The data can be processed individually or by a computer. For instance, a computer-implemented method for generating a data structure, tangibly embodied in a computer-readable medium, representing a quantitative value of a component of a polysaccharide may be performed according to the invention. The quantitative determination is made by performing the above calculation.

A computer system that may implement the above as a computer program typically may include a main unit connected to both an output device which displays information to a user and an input device which receives input from a user. The main unit generally includes a processor connected to a memory system via an interconnection mechanism. The input device and output device also may be connected to the processor and memory system via the interconnection mechanism.

One or more output devices may be connected to the computer system. Example output devices include a cathode ray tube (CRT) display, liquid crystal displays (LCD), printers, communication devices such as a modem, and audio output. One or more input devices also may be connected to the computer system. Example input devices include a keyboard, keypad, track ball, mouse, pen and tablet, communication device, and data input devices such as sensors. The subject matter disclosed herein is not limited to the particular input or output devices used in combination with the computer system or to those described herein.

The computer system may be a general purpose computer system which is programmable using a computer programming language, such as C++, Java, or other language, such as a scripting language or assembly language. The computer system also may include specially-programmed, special purpose hardware such as, for example, an Application-Specific Integrated Circuit (ASIC). In a general purpose computer system, the processor typically is a commercially-available processor, of which the series x86, Celeron, and Pentium processors, available from Intel, and similar devices from AMD and Cyrix, the 680X0 series microprocessors available from Motorola, the PowerPC microprocessor from IBM and the Alpha-series processors from Digital Equipment Corporation, are examples. Many other processors are available. Such a microprocessor executes a program called an operating system, of which Windows NT, Linux, UNIX, DOS, VMS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages may be written.

A memory system typically includes a computer readable and writeable nonvolatile recording medium, of which a magnetic disk, a flash memory and tape are examples. The disk may be removable, such as a "floppy disk," or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element typically allows for faster access to the information by the processor than does the disk. The processor generally manipulates the data within the integrated circuit memory and then copies the data to the disk after processing is completed. A variety of mechanisms are known for managing data movement between the disk and the integrated circuit memory element, and the subject matter disclosed herein is not limited to such mechanisms. Further, the subject matter disclosed herein is not limited to a particular memory system.

The subject matter disclosed herein is not limited to a particular computer platform, particular processor, or particular high-level programming language. Additionally, the computer system may be a multiprocessor computer system or may include multiple computers connected over a computer network. It should be understood that each module (e.g. 110, 120) in FIG. 1 may be separate modules of a computer program, or may be separate computer programs. Such modules may be operable on separate computers. Data (e.g., 104, 106, 110, 114 and 116) may be stored in a memory system or transmitted between computer systems. The subject matter disclosed herein is not limited to any particular implementation using software or hardware or firmware, or any combination thereof. The various elements of the system, either individually or in combination, may be implemented as a computer program product tangibly embodied in a machine-readable storage device for execution by a computer processor. Various steps of the process may be performed by a computer processor executing a program tangibly embodied on a computer-readable medium to perform functions by operating on input and generating output. Computer programming languages suitable for implementing such a system include procedural programming languages, object-oriented programming languages, and combinations of the two.

Improved methods for preparing LMWH compositions were also discovered according to the invention. The current methods of purifying low molecular weight heparin (LMWH) for clinical use include precipitation of a glycosaminoglycan mixture and the recovery of a fraction containing heparin fragments ranging in size from 1 to 14,000 Da. A standard method utilized in the purification of heparin is described in N. Volpi, Biochemica t Biophysica Acta 1290 (1996) 299-307:

. . . slow moving and fast moving components of heparin were purified as their barium salts at different temperatures, as previously reported. Purified bovine intestinal mucosa heparin was dissolved in water, and barium acetate (5%) was added slowly with stirring (the pH of the solution was adjusted to 6.0-7.0). After heating to 50°-70° C., the solution was left at room temperature (20-25° C.) for 24 h. The precipitate obtained was solubilized in water and transformed into its sodium salt on Amberlite IR-120 resin. The crude slow moving heparin species sodium salt was collected by precipitation with 2.0 volumes of acetone and dried. The supernatant was maintained at 5° C. for 24 h and the precipitate was collected by centrifugation at 5° C. The fast moving species barium salt was purified as reported for slow moving species.

The product obtained by this methodology is a heterogeneous mixture of heparin fragments which have presented numerous difficulties when administered to patients due to the heterogeneous nature of the product as well as the lack of ability to quantify the levels of active components in the mixture. In contrast, the novel purification strategy described herein, provides a substantially pure fraction of LMWH that is quantifiable and reproducible, and thus lacks many of the side effects associated with the prior art product. Surprisingly, it was discovered according to the invention that the fraction referred to as the fast moving component (the second fraction) which was discarded in the prior art methods actually has significant amounts of therapeutic activity. Thus, the method of the invention involves a similar type of precipitation reaction but involves isolation and manipulation of the previously discarded material.

In general the method of the invention involves a precipitation of HLGAG sample with a salt of divalent cations and weak anions. In some embodiments, the salt of the divalent cations and weak anions is selected from among the group including; barium, calcium, magnesium, strontium, copper, nickel, cadmium, zinc, mercury beryllium, nickel, palladium, platinum, iron, or tin. In some embodiments the salt of divalent cations and weak anions are acetates of cations of elements of the periodic table having divalent valence. In preferred embodiments the salt of divalent cations and weak anions is barium acetate. In other embodiments the salt of divalent cations and weak anions is calcium acetate or calcium chloride. In some embodiments other methods of acetate precipitation which are known to those of skill in the art may be used.

The precipitation may be performed in the temperature range from 0° C. to 70° C. The temperature for the precipitation may be 0° C., 2° C., 5° C., 10° C., 15° C., 20° C., 30° C., 40° C., 50° C., 60° C., or 70° C. or may be any temperature within this range. In a preferred embodiment the temperature of the precipitation is 4° C. In other embodiments, the temperature of the precipitation will be room temperature, which includes temperatures in the range of 18° C. to 22° C.

The solvent used in the precipitation is a polar solvent. In some embodiments, the polar solvent is $H_2O$, ethanol, acetone, $H_2O$ mixed with ethanol, $H_2O$ mixed with acetone, acetone. In some embodiments the polar solvent has a volume to volume H2O:ethanol ratio in the range of: 99:1, 95:5, 90:10, 85:15, 80:20, 75:25, 65:35, 55:45, 50:50, 45:55, 35:65, 25:75, 20:80, 15:85, 10:90, 5:95, or 1:99. In other embodiments the polar solvent has a volume to volume $H_2O$:acetone ratio in the range of 99:1, 95:5, 90:10, 85:15, 80:20, 75:25, 65:35, 55:45, 50:50, 45:55, 35:65, 25:75, 20:80, 15:85, 10:90, 5:95, or 1:99. In still other embodiments the polar solvent is a mixture of $H_2O$, ethanol, and acetone.

Following the precipitation step the sample (second fraction) may optionally be subjected to an ion-exchange process prior to being further processed. In some instances, the sample is passed through an ion-exchange column, such as an amberlite IR-120 column. Use of this type of column is useful for removing the salt used in the precipitation step and replacing it with another such as sodium.

The glycosaminoglycan-containing sample is a sample at least a fraction of which is composed of glycosaminoglycans or HLGAGs. As discussed above the term glycosaminoglycan or HLGAG include but are not limited to heparin, heparin analogs, LMWH, biotechnological heparin, chemically modified heparin, or synthetic heparin.

The glycosaminoglycan can be fractionated into heparin of a specific size by varying the conditions described herein for temperature, solvent, and enzyme. Examples of results of temperature variations, though not intending to be limiting, illustrate the variation in the content of precipitation fractions based on temperature. The use of 5% w/v barium acetate at 4° C. results in a second fraction that is comprised of LMWH as defined by the FDA. This fraction has high activity for anticoagulation, and low amount of sulfation (<70%). The fraction left in the supernatant at 4° C. can be categorized as the ultra low molecular weight heparin. In contrast to the 4° C. precipitation, room temperature precipitation results in fraction one that contains higher MW heparin (MW: 10,000-14,000), higher amount of sulfation (>85%), and lower activity for anticoagulation than does the precipitation performed at 4° C.

Another nonlimiting example is the use of 5% calcium acetate or magnesium acetate instead of 5% barium acetate. At 4° C. this change will result in precipitating fraction one (high molecular weight heparin) while leaving fraction two (low molecular weight heparin) in the supernatant. Fraction two can then be precipitated from the supernatant by adding a polar solvent such as ethanol or acetone.

In general, the higher molecular weight and/or higher charge fraction will precipitate at higher temperature, with a lower amount of polar solvent such as ethanol or acetone. Decreasing the temperature, and/or increasing the amount of polar solvent may result in the precipitation of the fraction with lower molecular weight, lower charge, and higher anticoagulation activity. The precipitation parameters may be altered without undue experimentation by one of ordinary skill in the art.

Following the precipitation, the second fraction, the LMWH fraction, is processed to produce a concentrated LMWH preparation. The term "concentrated LMWH preparation" refers to a preparation which has been altered in one way or another from the second isolated fraction. The processing step may involve a separation step or a purification step such as a precipitation. The processing of the LMWH preparation may further be accomplished by enzymatic or chemical digestion to yield the concentrated LMWH preparation. In one embodiment the fraction is digested and the enzyme used in the digestion is Heparinase III or a functionally active variant or fragment thereof. The term heparinase is used generically to encompass functionally active variants and fragments thereof in addition to the native heparinases. Several patents and patent applications describe useful modifications and variants and fragments of heparinase, including U.S. Pat. No. 6,217,863 B1 and pending application Ser. Nos. 09/384,959 and 09/802,285. Heparinase III causes depolymerization of heparin. Depending upon the concentration of heparinase III used, and the period for which it is used (partial vs exhaustive digestion), heparin of specific molecular weight, and/or charge is obtained. For example, although not intended to be limiting, is that a partial digestion of heparin with 1 molar equivalent of heparinase III would result in a fraction of higher molecular weight, and/or higher charge than would a reaction with a longer digestion time. Also, increasing the molar equivalence of heparinase III will result in a fraction with lower molecular weight and/or lower charge than if a lower molar equivalence of heparinase is used. In some embodiments, Heparinase III concentrations and length of digestions can be used in combination with salt, temperature, and solvent composition, as described herein, to obtain heparin of specific molecular weight, charge and/or biological activity.

Alternatively, the second fraction may be chemically degraded to yield the concentrated LMWH preparation. In one embodiment the fraction is chemical degraded using a method selected from the group including but not limited to: oxidative depolymerization with $H_2O_2$ or $CU^+$ and $H_2O_2$, deaminative cleavage with isoamyl nitrite, or nitrous acid, β-eliminative cleavage with benzyl ester of heparin by alkaline treatment or by heparinase.

The second fraction of the precipitation, which is referred to as fast moving heparin in the Volpi reference, differs from the first fraction, which is referred to by Volpi reference as the slow moving heparin. The average molecular weight of the second fraction is 8,000 Dalton and the average molecular weight of the first fraction is 14,000 Dalton. In addition, the second fraction is comprised of 100% LMWH with LMWH defined as a heparin sub-species of average molecular weight of less than 8,000 Da, and in which at least 60% of the molecules have a molecular weight less than 8,000 Da. Using this definition, the first fraction is 0% LMWH.

The invention also includes compositions of LMWH preparations. The composition of LMWH is a mixture of various molecular weight molecules. As described above, the homogenous mixture contains fragments that can range in molecular weight but have an average molecular weight of less than 8,000 D. A composition of LMWH of compounds having a molecular weight range from 4,000-6,000 Daltons, for instance, is a mixture of various LMWH in which the average size ranges from 4,000 to 6,000 Da. In some embodiments, the percentage of LMWH that is from 4,000 to 6,000 Da in the sample is 20%, 30%, 40%, 50%, 60%, 70%, 80%, 90%, or 100% of the components in the sample.

In some aspects the composition is a LMWH preparation having an anti-Xa activity of at least 150 IU/mg. In some embodiments the LMWH preparation has an anti-factor Xa:anti-factor IIa activity ratio of greater than 1, 2, 3, 4, or 5.

In other aspects the composition is a LMWH preparation having an anti-factor Xa:anti-factor IIa activity ratio of greater than 5. In yet other aspects the composition is LMWH preparation having at least 3.5% $\Delta UH_{NAC,6S}GH_{NS,3S,6S}$, $\Delta UH_{NS,6S}GH_{NS,3S,6S}$; $\Delta UH_{NAC,6S}GH_{NS,3S}$; or $\Delta UH_{NS,6S}GH_{NS,3S}$. In some embodiments the LMWH preparation has at least 4.0, 4.5, 5.0, 5.5, 6.0, 6.5, 7.0, 8.0, 9.0, 10.0, 15.0, or 20.0% $\Delta UH_{NAC,6S}GH_{NS,3S,6S}$, $\Delta UH_{NS,6S}GH_{NS,3S,6S}$; $\Delta UH_{NAC,6S}GH_{NS,3S}$; or $\Delta UH_{NS,6S}GH_{NS,3S}$.

The LMWH compositions of the invention may optionally be formulated in a pharmaceutically acceptable carrier. The compositions may further be formulated into specific delivery devices. Thus in some embodiments of the invention the compositions are specifically formulated for intravenous, subcutaneous, oral, aerosol, or other mucosal form of delivery. In some embodiments the compositions are formulated in sustained release devices as described below.

One of ordinary skill in the art, in light of the present disclosure, is enabled to produce substantially pure preparations of LMWH compositions. The LMWH preparations are prepared from HLGAG sources. A "HLGAG source" as used herein refers to heparin like glycosaminoglycan composition which can be manipulated to produce LMWH using standard technology, including enzymatic degradation etc. As described above, HLGAGs include but are not limited to isolated heparin, chemically modified heparin, biotechnology prepared heparin, synthetic heparin, heparan sulfate, and LMWH. Thus HLGAGs can be isolated from natural sources, prepared by direct synthesis, mutagenesis, etc. The HLGAGs may in some embodiments be substantially pure. As used herein, the term "substantially pure" means that the polysaccharides are essentially free of other substances to an extent practical and appropriate for their intended use. In particular, the polysaccharides are sufficiently pure and are sufficiently free from other biological constituents of their hosts environments so as to be useful in, for example, producing pharmaceutical preparations.

LMWH preparations as used herein are salts of sulfated GAGs having an average molecular weight (MW) of less than 8000 Da and for which at least 60% of all molecules have a MW less than 8000 Da. By definition LMWH preparations are produced from an HLGAG sample. The term LMWH does not encompass polysaccharides which are synthesized directly as LMWHs, such as SR90107A. SR90107A is a synthetic polysaccharide having a molecular weight of approximately 1500 Da. These types of compounds, which are prepared directly as low molecular weight compounds rather than being prepared from a source of HLGAGs are not considered to fall within the class of LMWH. The term LMWH does include, however, synthetic HLGAGs which are processed to produce LMWHs.

Several different methods have been used for the commercial preparation of LMWHs. Direct size fractionation has been used to prepare LMWH (Fraxiparin) on an experimental scale but its poor yield has generally negated its use on an industrial scale. For industrial production purposes, a number of chemical or enzymatic processes have been utilized. Chemical processes take advantage of a wide range of reactions such as partial nitrous acid depolymerization (Fragmin), oxidative cleavage with $H_2O_2$ (Normiflo and Fluxum), oxidative cleavage with $Cu^{++}$ and $H_2O_2$, or by benzylation followed by β-elimination and alkaline hydrolysis (Enoxaparin). Enzymatic methods to generate LMWH using partial β-eliminative depolymerization by heparinase I (Logiparin) have also been described.

The LMWHs produced according to the invention have improved functional properties over prior art LMWH preparations. One advantage of the compositions of the invention is that the amount of anti-coagulant activity can be altered for therapeutic purposes. Depending on the subject being treated and/or the condition of the subject it may be desirable to increase or decrease the anti-coagulant activity of the compounds. For instance, if a subject is undergoing an acute clotting event, it is often desirable to administer to the subject a LMWH preparation having high anti-coagulant activity, such as one of the compositions having an activity of at least 150 IU/mg. Other subjects may only be at risk of developing a thrombotic disorder. It is generally desirable to administer to these subjects a LMWH preparation having a lower anti-coagulant activity. The ability to identify the percentage of uncleaved AT-binding region, such as the decasaccharide having structure $\Delta U_{2S}H_{NS,6S}I_{2S}H_{NS,6S}I_{2S}H_{NS,6S}IH_{NAc,6S}GH_{NS,3S,6S}$, or one of the tetrasaccharides $\Delta UH_{NAC,6S}GH_{NS,3S,6S}$, $\Delta UH_{NS,6S}GH_{NS,3S,6S}$; $\Delta UH_{NAC,6S}GH_{NS,3S}$; or $\Delta UH_{NS,6S}GH_{NS,3S}$ (or related compounds) in a sample allows compositions to be formulated with specific amounts of uncleaved, intact AT-binding region This ability to prepare LMWH with known percentages of intact AT-binding region provides a method to quantitate the activity of therapeutic compositions of LMWH. Thus, the methods of the invention enable one of skill in the art to prepare or identify an appropriate composition of LMWH, depending on the subject and the disorder being treated.

As used herein, the word "intact" means uncleaved and complete. The term "AT-binding regions" refers to a region of HLGAG that specifically interacts with AT-III. The AT-binding region, includes the decasaccharide compound with the structure: $\Delta U_{2S}H_{NS,6S}I_{2S}H_{NS,6S}I_{2S}H_{NS,6S}IH_{NAc,6S}GH_{NS,3S,6S}$ and the tetrasaccharides $\Delta UH_{NAC,6S}GH_{NS,3S,6S}$, $\Delta UH_{NS,6S}GH_{NS,3S,6S}$; $\Delta UH_{NAC,6S}GH_{NS,3S}$; and $\Delta UH_{NS,6S}GH_{NS,3S}$. In some embodiments, the LMWH preparation is a composition wherein at least 20% of the polysaccharide sequence in the composition is intact AT-binding region. In other embodiments at least 25%, 30%, 35%; 40%; 45%, 50%, or 55% of the polysaccharide sequence in the composition is intact AT-binding region. As discussed above, the optimal percentage of intact AT-10 in a composition for treatment will vary depending on the medical condition under treatment. A higher level of activity may be desirable for patients in danger of blood-clot formation than in patients under treatment for cancer, in which anticoagulant activity is not desirable.

In other aspects the composition is a LMWH preparation having >15% disulfated disaccharides, < than 75% trisulfated disaccharides, 3-5% monosulfated disaccharides, > than 2% 4-7 tetrasaccharide. The LMWH preparation has an average MW<8,000 of which at least 60% of the chains have a MW<8,000. LMWH preparations having these properties have an anti-XA activity of >150 IU/mg and an antiXa/IIA value of > than 1.5. Compositions having these properties can be prepared by the above described methods. The material referred to as the fraction 2 LMWH preparation is a composition having these properties. The composition of fraction 1 is a Heparin material having <15% disulfated disaccharides, > than 75% trisulfated disaccharides, 0-3% monosulfated disaccharides, 0-2% 4-7 tetrasaccharide, and having an average MW of 8000-14000. Fraction 1 material has an anti-XA activity of <150 IU/mg and an antiXa/IIA value of <2.

The amount of AT-binding region in the LMWH preparations can be manipulated by a variety of experimental parameters. The methods of the invention make it possible to control the amounts of AT-binding region in a LMWH preparation by enabling the quality control of LMWH preparations using the signature component, by providing an improved isolation procedure which results in the isolation of a LMWH-rich preparation, and by providing new rules for the cleavage specificities of heparinases. The first two of these properties are discussed in detail above.

The role of heparinases in preparing LMWHs with intact AT-binding regions has been described in the prior art. Specifically a published sequence that contained an intact AT-III binding site, was described as being $\Delta U_{2S}H_{NS,6S}IH_{NAc,6S}GH_{NS,3S,6S}I_{2S}H_{NS,6S}I_{2S}H_{NS,6S}$ (Toida, T., Hileman, R. E., Smith, A. E., Vlahova, P. I. & Linhardt, R. J. (1996) *J Biol Chem* 271, 32040-7). Furthermore, tetrasaccharides containing 3-O sulfate have been shown in the prior art to be uncleavable by any of the heparinases (Yamada, S., Yoshida, K., Sugiura, M, Sugahara, K., Khoo, K. H., Morris, H. R. & Dell, A. (1993) *J Biol Chem* 268, 4780-7), suggesting that linkages with a 3-O sulfated glucosamine are resistant to cleavage. Surprisingly, it was discovered that these prior art teachings were incorrect. In the Examples, we conclusively showed through a variety of physical chemical techniques that the actual structure of AT-10 is $\Delta U_{2S}H_{NS,6S}I_{2S}H_{NS,6S}I_{2S}H_{NS,6S}IH_{NAc,6S}GH_{NS,3S,6S}$ and therefore does not contain an intact AT-III binding site. In light of the reinterpretation of the AT-10 structure, we sought to reexamine the action of heparinases I-III towards AT binding, 3-O sulfate containing oligosaccharides. Given that AT-10 (ultra-LMWH, MW=2769.3 Da) is derived from controlled heparinase I cleavage of heparin, we also sought to examine the functional consequences of an oligosaccharide, using established bio-analytical techniques. Such an understanding of both heparinase action and functional consequences is required for the efficient, optimal generation of LMWH for clinical use.

Thus, as shown in the Examples, it has been discovered that heparinase I and II actually cleave the AT-binding region of HLGAGs resulting in the loss of intact AT-binding region, whereas heparinase III does not. Furthermore, it has been discovered that glucosamine 3-0 sulfation at the reducing end of a glycosidic linkage imparts resistance to heparinase I, II and III cleavage. Examination of the biological and pharmacological consequences of a heparin oligosaccharide that contains only a partial AT-III binding site shows that such an oligosaccharide has significant anti-Xa activity but lacks some of the functional attributes of heparin-like glycosaminoglycan containing an intact AT-III site. Thus if a preparation of HLGAGs is produced, such as, for example, by the precipitation method described above, the preparation can be further modified such that it has a higher or lower anti-coagulant activity by enzymatically cleaving with heparinases. If the preparation is subjected to enzymatic cleavage by heparinase I and/or II the anti-coagulant activity will be reduced. If the preparation is treated with heparinase III the anti-coagulant activity will be enhanced.

These methods are also true for a broader class of compounds. The teachings of the invention can be used to develop specialized polysaccharide therapeutics from a wide variety of polysaccharide starting materials. Once an active component is identified in a polysaccharide, that active component can be used as a signature for the quality control of the sample, and can be used to generate and identify therapeutic compositions which are enhanced for a particular therapeutic activity, and which have had the regions which are responsible for side effects removed.

The compositions may be administered therapeutically to a subject. As used herein, a subject is a human, non-human primate, cow, horse, pig sheep, goat dog, cat, or rodent.

HLGAGs and LMWHs in particular have many therapeutic utilities. The LMWH compositions of the invention can be used for the treatment of any type of condition in which LMWH therapy has been identified as a useful therapy. Thus, the invention is useful in a variety of in vitro, in vivo and ex vivo methods in which LMWH therapies are useful. For instance, it is known that LMWH compositions are useful for preventing coagulation, inhibiting cancer cell growth and metastasis, preventing angiogenesis, preventing neovascularization, preventing psoriasis. The LMWH compositions may also be used in in vivo assays, such as a quality control sample.

Each of these disorders is well-known in the art and is described, for instance, in *Harrison's Principles of Internal Medicine* (McGraw Hill, Inc., New York), which is incorporated by reference.

Thus, the LMWH preparations, are useful for treating or preventing disorders associated with coagulation. A "disease associated with coagulation" as used herein refers to a condition characterized by local inflammation resulting from an interruption in the blood supply to a tissue due to a blockage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The methods of the invention are useful also for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption in blood flow to the brain resulting from either a thromboembolism. A stroke causes a loss of neurons typically resulting in a neurologic deficit that may improve but that does not entirely resolve. Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms.

The methods of the invention in some embodiments are directed to the treatment of acute thromboembolic stroke using LMWHs. An acute stroke is a medical syndrome involving neurological injury resulting from an ischemic event, which is an interruption in the blood supply to the brain.

An effective amount of a LMWH preparation alone or in combination with another therapeutic for the treatment of stroke is that amount sufficient to reduce in vivo brain injury resulting from the stroke. A reduction of brain injury is any prevention of injury to the brain which otherwise would have occurred in a subject experiencing a thromboembolic stroke absent the treatment of the invention. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

The pharmaceutical LMWH preparation may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S-22S (1995); Holmes, et al, *J Am Coll Cardiol*; v. 25 (7 supply, p. 10S-17S (1995)). Thrombolytic agents include, but are not limited to, plasminogen, $a_2$-antiplasmin, streptokinase, antistreplase, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et. al., *Anal. Biochem.* 168, 428-435 (1988) and its modified form described by Bennett, W. F. Et al., 1991, Supra, the entire contents of which are hereby incorporated by reference.

In one embodiment the LMWH preparations are used for inhibiting angiogenesis. An effective amount for inhibiting angiogenesis of the LMWH preparation is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. An effective amount for inhibiting angiogenesis is an amount of LMWH preparation which is sufficient to diminish the number of blood vessels growing into a tumor. This amount can be assessed in an animal model of tumors and angiogenesis, many of which are known in the art.

The LMWH preparations are also useful for inhibiting neovascularization associated with eye disease. In another embodiment, the LMWH preparation is administered to treat psoriasis. Psoriasis is a common dermatologic disease causes by chronic inflammation.

LMWH containing compositions, may also inhibit cancer cell growth and metastasis. Thus the methods of the invention are useful for treating and/or preventing tumor cell proliferation or metastasis in a subject. The terms "prevent" and "preventing" as used herein refer to inhibiting completely or partially the biological effect, e.g., angiogenesis or proliferation or metastasis of a cancer or tumor cell, as well as inhibiting any increase in the biological effect, e.g., angiogenesis or proliferation or metastasis of a cancer or tumor cell.

The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

A subject in need of treatment may be a subject who has a high probability of developing cancer. These subjects include, for instance, subjects having a genetic abnormality, the presence of which has been demonstrated to have a correlative relation to a higher likelihood of developing a cancer and subjects exposed to cancer-causing agents such as tobacco, asbestos, or other chemical toxins, or a subject who has previously been treated for cancer and is in apparent remission.

Effective amounts of the composition containing LMWH of the invention are administered to subjects in need of such treatment. Effective amounts are those amounts which will result in a desired reduction in cellular proliferation or metastasis or prevent coagulation without causing other medically unacceptable side effects. Such amounts can be determined with no more than routine experimentation. It is believed that doses ranging from 1 nanogram/kilogram to 100 milligrams/kilogram, depending upon the mode of administration, will be effective. The effective percentage of intact LMWH may be determined with no more than routine experimentation. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including inhalation, oral, subcutaneous, intravenous, etc.

In some aspects of the invention the effective amount of a composition containing LMWH is that amount effective to prevent invasion of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327-336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus the LMWH compositions can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378-383. Matrigel is a reconstituted basement membrane containing type IV collagen, laminin, heparan sulfate proteoglycans such as perlecan, which bind to and localize bFGF, vitronectin as well as transforming growth factor (TGF), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

According to another aspect of the invention, there is provided methods for treating subjects in need of depletion of circulating heparin. Effective amounts of combinations of heparinases I, II, and III (or modified forms thereof are utilized) in this aspect. For example, subjects undergoing open heart surgery or hemodialysis often are in need of depletion of medically undesirable amounts of heparin in blood as a result of the surgery or hemodialysis. By using a combination of heparinase I or II and heparinase III the appropriate amount of therapeutically active (anti-coagulant function) can be administered to a subject to obtain an appropriate balance of the coagulation cascade. Effective amounts of the combination of heparinases are those amounts which will result in a desired reduction in circulating heparin levels without complete depletion and without causing any other medically unacceptable side effects.

In general the therapeutically useful amounts of the combination of heparinases can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The present invention provides pharmaceutical compositions, for medical use, which comprise LMWH preparations together with one or more pharmaceutically acceptable carriers and optionally other therapeutic ingredients. The term "pharmaceutically-acceptable carrier" as used herein, and described more fully below, means one or more compatible solid or liquid filler, dilutants or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with the LMWH of the present invention, and with each other, in a manner such that there is no interaction which would substantially impair the desired pharmaceutical efficiency.

Compositions suitable for parenteral administration conveniently comprise a sterile aqueous preparation of the polysaccharide, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

A variety of administration routes are available. The particular mode selected will depend, of course, upon the particular percentage of LMWH selected, the particular condition being treated, and the dosage required for therapeutic efficacy. The methods of this invention, generally speaking, may be practiced using any mode of administration that is medically acceptable, meaning any mode that produces effective levels of an biological effect without causing clinically unacceptable adverse effects.

For use in therapy, an effective amount of the LMWH preparation can be administered to a subject by any mode that delivers the LMWH to the desired surface, e.g., mucosal, systemic. "Administering" the pharmaceutical composition of the present invention may be accomplished by any means known to the skilled artisan. Preferred routes of administration include, but are not limited to, oral, parenteral, intramuscular, intranasal, intratracheal, inhalation, ocular, vaginal and rectal.

For oral administration, the compounds (i.e., LMWH preparations) can be formulated readily by combining the active compound(s) with pharmaceutically acceptable carriers well-known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally, the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long-acting formulations may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro) capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, (1990), which is incorporated herein by reference.

The compositions may conveniently be presented in unit dosage form and may be prepared by any of the methods well known in the art of pharmacy. All methods include the step of bringing the active LMWH into association with a carrier which constitutes one or more accessory ingredients. In general, the compositions are prepared by uniformly and intimately bringing the polysaccharide into association with a liquid carrier, a finely divided solid carrier, or both, and then, if necessary, shaping the product. The polysaccharide may be stored lyophilized.

Other delivery systems can include time-release, delayed release or sustained release delivery systems. Such systems can avoid repeated administrations of the LMWH of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S.

Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

When administered to a patient undergoing cancer treatment, the LMWH compositions may be administered in cocktails containing other anti-cancer agents. The compositions may also be administered in cocktails containing agents that treat the side-effects of radiation therapy, such as anti-emetics, radiation protectants, etc.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The LMWH compositions may also be linked to a targeting molecule. A targeting molecule is any molecule or compound which is specific for a particular cell or tissue and which can be used to direct the LMWH to the cell or tissue. Preferably the targeting molecule is a molecule which specifically interacts with a cancer cell or a tumor. For instance, the targeting molecule may be a protein or other type of molecule that recognizes and specifically interacts with a tumor antigen.

Tumor-antigens include Melan-A/M A R T-1, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21 ras, RCAS1, fetoprotein, E-cadherin, catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

Examples of tumor antigens which bind to either or both MHC class I and MHC class II molecules, see the following references: Coulie, *Stem Cells* 13:393-403, 1995; Traversari et al., *J. Exp. Med.* 176:1453-1457, 1992; Chaux et al., *J. Immunol.* 163:2928-2936, 1999; Fujie et al., *Int. J. Cancer* 80:169-172, 1999; Tanzarella et al., *Cancer Res.* 59:2668-2674, 1999; van der Bruggen et al., *Eur. J. Immunol.* 24:2134-2140, 1994; Chaux et al., *J. Exp. Med.* 189:767-778, 1999; Kawashima et al, *Hum. Immunol.* 59:1-14, 1998; Tahara et al., *Clin. Cancer Res.* 5:2236-2241, 1999; Gaugler et al., *J. Exp. Med* 179:921-930, 1994; van der Bruggen et al., *Eur. J. Immunol.* 24:3038-3043, 1994; Tanaka et al., *Cancer Res.* 57:4465-4468, 1997; Oiso et al., *Int. J. Cancer* 81:387-394, 1999; Herman et al., *Immunogenetics* 43:377-383, 1996; Manici et al., *J. Exp. Med.* 189:871-876, 1999; Duffour et al., *Eur. J. Immunol.* 29:3329-3337, 1999; Zorn et al., *Eur. J. Immunol.* 29:602-607, 1999; Huang et al., *J. Immunol* 162:6849-6854, 1999; Boël et al., *Immunity* 2:167-175, 1995; Van den Eynde et al., *J. Exp. Med.* 182:689-698, 1995; De Backer et al., *Cancer Res.* 59:3157-3165, 1999; Jäger et al., *J. Exp. Med.* 187:265-270, 1998; Wang et al., *J. Immunol.* 161:3596-3606, 1998; Aarnoudse et al., *Int. J. Cancer* 82:442-448, 1999; Guilloux et al., *J. Exp. Med* 183:1173-1183, 1996; Lupetti et al., *J. Exp. Med.* 188:1005-1016, 1998; Wölfel et al., *Eur. J. Immunol.* 24:759-764, 1994; Skipper et al., *J. Exp. Med.* 183:527-534; 1996; Kang et al., *J. Immunol.* 155:1343-1348, 1995; Morel et al., *Int. J. Cancer* 83:755-759, 1999; Brichard et al., *Eur. J. Immunol.* 26:224-230, 1996; Kittlesen et al., *J. Immunol.* 160:2099-2106, 1998; Kawakami et al., *J. Immunol.* 161:6985-6992, 1998; Topalian et al., *J. Exp. Med* 183:1965-1971, 1996; Kobayashi et al., *Cancer Research* 58:296-301, 1998; Kawakami et al., *J. Immunol.* 154:3961-3968, 1995; Tsai et al., *J. Immunol.* 158:1796-1802, 1997; Cox et al., *Science* 264:716-719, 1994; Kawakami et al., *Proc. Natl. Acad. Sci. USA* 91:6458-6462, 1994; Skipper et al., *J. Immunol.* 157:5027-5033, 1996; Robbins et al., *J. Immunol.* 159:303-308, 1997; Castelli et al, *J. Immunol.* 162:1739-1748, 1999; Kawakami et al., *J. Exp. Med.* 180:347-352, 1994; Castelli et al., *J. Exp. Med* 181:363-368, 1995; Schneider et al., *Int. J. Cancer* 75:451-458, 1998; Wang et al., *J. Exp. Med.* 183:1131-1140, 1996; Wang et al., *J. Exp. Med* 184:2207-2216, 1996; Parkhurst et al., *Cancer Research* 58:4895-4901, 1998; Tsang et al. *J. Natl Cancer Inst* 87:982-990, 1995; Correale et al., *J Natl Cancer Inst* 89:293-300, 1997; Coulie et al., *Proc. Natl. Acad. Sci. USA* 92:7976-7980, 1995; Wölfel et al., *Science* 269:1281-1284, 1995; Robbins et al., *J. Exp. Med.* 183:1185-1192, 1996; Brändle et al., *J. Exp. Med.* 183:2501-2508, 1996; ten Bosch et al., *Blood* 88:3522-3527, 1996; Mandruzzato et al., *J. Exp. Med.* 186:785-793, 1997; Guéguen et al., *J. Immunol.* 160:6188-6194, 1998; Gjertsen et al., *Int. J. Cancer* 72:784-790, 1997; Gaudin et al., *J. Immunol.* 162:1730-1738, 1999; Chiari et al., *Cancer Res.* 59:5785-5792, 1999; Hogan et al., *Cancer Res.* 58:5144-5150, 1998; Pieper et al., *J. Exp. Med.* 189:757-765, 1999; Wang et al., *Science* 284:1351-1354, 1999; Fisk et al., *J. Exp. Med* 181:2109-2117, 1995; Brossart et al., *Cancer Res.* 58:732-736, 1998; Röpke et al., *Proc. Natl. Acad. Sci. USA* 93:14704-14707, 1996; Ikeda et al., *Immunity* 6:199-208, 1997; Ronsin et al., *J. Immunol.* 163:483-490, 1999; Vonderheide et al., *Immunity* 10:673-679, 1999. These antigens as well as others are disclosed in PCT Application PCT/US98/18601.

The following description of experiments performed is exemplary and non-limiting to the scope of the claimed invention.

EXAMPLES

Example 1

Sequencing of 3-O Sulfate Containing Decasaccharides with a Partial Antithrombin III Binding Site Introduction:

Heparin and heparan sulfate glycosaminoglycans represent an important class of molecules that interact with and modulate the activity of growth factors, enzymes, and morphogens. Of the many biological functions for this class of molecules, one of its most important functions is its interaction with antithrombin III (AT-III). AT-III binding to a specific heparin pentasaccharide sequence, containing an unusual 3-O sulfate on a N-sulfated, 6-O sulfated glucosamine, increases 1000-fold ability to inhibit specific proteases in the coagulation cascade. In this manner, heparin-like glycosaminoglycans (HLGAGs) play an important biological and pharmacological role in the modulation of blood clotting. Recently, a sequencing methodology was developed (U.S. patent application Ser. Nos. 09/557,997 and 09/558,137 filed on Apr. 24, 2000, having common inventorship, which are incorporated by reference and Venkataraman, G., Shriver, Z., Raman, R. & Sasisekharan, R. (1999) *Science* 286, 537-42) to further structure-function relationships of this important class of molecules. This methodology combines a property-encoded nomenclature scheme (PEN), to handle the large information content (properties) of HLGAGs, with matrix-assisted laser desorption ionization mass spectrometry (MALDI-MS) and enzymatic and chemical degradation as experimental constraints to rapidly sequence picomole quantities of HLGAG oligosaccharides. Using the above PEN-MALDI approach, we found that the sequence of the decasaccharide used in this study is $\Delta U_{2S}H_{NS,6S}I_{2S}H_{NS,6S}I_{2S}H_{NS,6S}IH_{NAc,6S}GH_{NS,3S,6S}$ (±DDD4-7). We confirmed our results: using Integral Glycan Sequencing and one dimensional proton nuclear magnetic resonance. Furthermore, we showed that this approach is flexible and is able to derive sequence information from an oligosaccharide mixture. Thus, this methodology makes possible both the analysis of other unusual sequences in polysaccharides such as heparin/heparan sulfate with important biological activities as well as provides the basis for the structural analysis of these pharmacologically important group of heparin/heparan sulfates.

Methods

Abbreviations: HLGAG, heparin-like glycosaminoglycans; AT-III, antithrombin III; AT-10, AT-III fractionated decasaccharide isolated from partial digestion of heparin; IGS, Integral Glycan Sequencing; PEN, property encoded nomenclature; MALDI-MS, matrix assisted laser desorption ionization mass spectrometry; CE, capillary electrophoresis; HLGAG sequence abbreviations as follows, I, α-L-iduronic acid; G, β-D-glucuronic acid; ΔU, a $\Delta^{4,5}$ uronic acid; 2S, 3S, and 6S, 2-O, 3-O, or 6-O sulfation respectively; NS and NAc, N-sulfation and N-acetylation of the glucosamine.

Materials. The decasaccharide AT-10 is the same saccharide used in previous studies (Rhomberg, A. J., Shriver, Z., Biemann, K. & Sasisekharan, R. (1998) *Proc Natl Acad Sci USA* 95, 12232-7 and Ernst, S., Rhomberg, A. J., Biemann, K. & Sasisekharan, R. (1998) *Proc Natl Acad Sci USA* 95, 4182-7). Oligosaccharides were dissolved in deionized water at concentrations of 10-35 μM. Heparinase I-III from *Flavobacterium heparinum* were purified as described previously. The exoenzymes α-L-iduronate 2-O sulfatase, α-L-iduronidase, β-D-glucuronidase and N-acetylglucosamine-6-sulfatase were purchased from Oxford Glycosciences. A 40% aqueous solution of sodium nitrite was purchased from Aldrich Chemical. Disaccharide standards for compositional analysis were purchased from Sigma-Aldrich (St. Louis, Mo.).

Compositional Analysis. Compositional analysis of oligosaccharides was completed by exhaustive digest of a 30 μM sample of AT-10 followed by capillary electrophoresis (CE) as described previously (Rhomberg, A. J., Ernst, S., Sasisekharan, R. & Biemann, K. (1998) *Proc Natl Acad Sci USA* 95, 4176-81). Briefly, to 1 nmol of oligosaccharide was added 200 nM of heparinases I, II, and III in 25 mM sodium acetate, 100 mM NaCl, 5 mM calcium acetate buffer pH 7.0. The reaction was allowed to proceed at 30° C. overnight and then analyzed by CE in reverse polarity with a running buffer of 50 mM tris/phosphate 10 μM dextran sulfate pH 2.5.

Digests. Heparinase I digestions were designated either short or exhaustive. For short digestion, 50 nM heparinase I was incubated with the substrate for 10 minutes prior to analysis. Exhaustive digestions were completed with 200 nM enzyme overnight. Enzyme reactions were performed by adding 1 μl of enzyme solution in a buffer containing 10 μM ovalbumin, 1 μM dextran sulfate, 5 mM calcium acetate and 10 mM ethylenediamine buffer at pH 7.0 to 4 μL of aqueous substrate solution; digestion was allowed to proceed at room temperature as described previously (Venkataraman, G., Shriver, Z., Raman, R. & Sasisekharan, R. (1999) *Science* 286, 537-42 and Rhomberg, A. J., Ernst, S., Sasisekharan, R. & Biemann, K. (1998) *Proc Natl Acad Sci USA* 95, 4176-81).

Partial nitrous acid cleavage was completed using a modification of published procedures (Turnbull, J. E., Hopwood, J. J. & Gallagher, J. T. (1999) *Proc Natl Acad Sci USA* 96, 2698-703). Exoenzyme digests were completed either simultaneously or sequentially. Final enzyme concentrations were in the range of 20-40 milliunits/mL and digestion was carried out at 37° C.

Mass Spectrometry. Mass spectral analyses were carried out on a PerSeptive Biosystems Voyager Elite reflectron time-of-flight instrument in the linear mode with delayed extraction. Samples from digests were prepared by removing 0.5 µl of the reaction mixture and adding it to 4.5 µl of matrix solution (12 mg/mL caffeic acid in 30% acetonitrile) that contained a 2-fold molar excess of the basic peptide $(RG)_{19}R$ (calculated mass of the $(M+H)^+$ ion=4226.8). Addition of the basic peptide to specifically chelate HLGAG oligosaccharides and mass spectral collection parameters allow for direct sample analysis without need for sample repurification (Rhomberg, A. J., Ernst, S., Sasisekharan, R. & Biemann, K. (1998) *Proc Natl Acad Sci USA* 95, 4176-81). Samples were spotted on the target and mass spectra were collected using parameters outlined previously (Rhomberg, A. J., Ernst, S., Sasisekharan, R. & Biemann, K. (1998) *Proc Natl Acad Sci USA* 95, 4176-81). Observed in each mass spectrum are the $(M+H)^+$ ions of the basic peptide and the $(M+H)^+$ ion of a 1:1 peptide:saccharide complex, and the mass of the saccharide is determined by subtracting the measured m/z value of the $(M+H)^+$ ion of the peptide from that of the 1:1 complex (Juhasz, P. & Biemann, K. (1995) *Carbohydr Res* 270, 131-47). All spectra on a plate were calibrated externally using a standard of $(RG)_{19}R$ and its complex with a nitrous acid-derived hexasaccharide of the sequence $I_{2S}H_{NS,6S}I_{2S}H_{NS,6S}I_{2S}Man_{6S}$ (calculated mass of 1655.4) under identical instrumental parameters. This methodology requires sufficient sulfation of the saccharide to ensure efficient complexation. As such, small, undersulfated saccharides (i.e., mono- and disaccharides) are not observed with this methodology (Juhasz, P. & Biemann, K. (1995) *Carbohydr Res* 270, 131-47).

Integral Glycan Sequencing. Integral glycan sequencing (IGS) using electrophoretic separation was carried out as described (Turnbull, J. E., Hopwood, J. J. & Gallagher, J. T. (1999) *Proc Natl Acad Sci USA* 96, 2698-703). Partial nitrous acid cleavage conditions were modified by using 25 mM HCl and 2.5 mM sodium nitrite and stop time points of 5, 10, 20, 30, 120, and 240 minutes.

$^1$H NMR Spectroscopy. $^1$H NMR spectroscopy was performed using the conditions described previously (Nadkarni, V. D., Toida, T., Van Gorp, C. L., Schubert, R. L., Weiler, J. M., Hansen, K. P., Caldwell, E. E. & Linhardt, R. J. (1996) *Carbohydr Res* 290, 87-96). AT-10 was subjected to ion-exchange chromatography to remove paramagnetic impurities. A column (1 cm×10 cm) of AG 50W-X8 (Bio-Rad Japan, Tokyo) was converted into sodium form by treatment with 5 mL of 0.1 M NaOH and washed with water for 12 hr before use. The sample for NMR experiments was applied to the column, eluted with 20 mL of water and freeze-dried. The sample (~1 mg) was then freeze-dried three times from 99.8% $D_2O$ (Merck, Germany) and dissolved in 0.5 mL of 100% $D_2O$ (Aldrich Japan, Tokyo) for NMR spectroscopy in a 5 mm tube. 1D $^1$H NMR spectroscopy of AT-10 was performed on a JEOL GSX 500A spectrometer equipped with a 5-mm field gradient tunable probe at 298K.

Results

Introduction to Sequencing Methodology

Recently a matrix-assisted laser desorption ionization mass spectrometry (MALDI-MS) technique enabling the determination of the mass of HLGAG complex oligosaccharides (from di to decasaccharides) to an accuracy of better than ±1 Da was developed (Juhasz, P. & Biemann, K. (1995) *Carbohydr Res* 270, 131-47 and Juhasz, P. & Biemann, K. (1994) *Proc Natl Acad Sci USA* 91, 4333-7). Because of the accuracy of the resulting molecular mass measurement of the individual HLGAGs, a unique assignment of both the length of a fragment and the number and kind of substituents is possible, especially if the oligosaccharide is a tetradecasaccharide or smaller (Venkataraman, G., Shriver, Z., Raman, R. & Sasisekharan, R. (1999) *Science* 286, 537-42). In addition, MALDI-MS can detect oligosaccharide fragments generated upon enzymatic or chemical degradation of an oligosaccharide (Rhomberg, A. J., Shriver, Z., Biemann, K. & Sasisekharan, R. (1998) *Proc Natl Acad Sci USA* 95, 12232-7; Ernst, S., Rhomberg, A. J., Biemann, K. & Sasisekharan, R. (1998) *Proc Natl Acad Sci USA* 95, 4182-7; and Rhomberg, A. J., Ernst, S., Sasisekharan, R. & Biemann, K. (1998) *Proc Natl Acad Sci USA* 95, 4176-81). Finally, the sensitivity of MALDI-MS is such that as little as 100 femtomoles of material can be readily detected.

In addition to the MALDI-MS experimental technique, a property-encoded nomenclature (PEN) for representing the 32 disaccharide units using a hexadecimal coding system was developed (Venkataraman, G., Shriver, Z., Raman, R. & Sasisekharan, R. (1999) *Science* 286, 537-42). The development of PEN is necessary to handle the large information content (properties) of HLGAGs. Each of the hexadecimal numbers is derived based on an internal logic that manifests itself in terms of the distribution of sulfates on a particular building block unit and is not randomly assigned simply to identify each disaccharide unit. This system is critical for HLGAGs in that it enables the rapid manipulation of sequences using simple mathematical or binary operations, hence providing a handle on the large information content of complex polysaccharides. In addition, the inherent structural diversity in HLGAGs necessarily arises from the property differences (location of charged sulfate and acetate groups) thereby making PEN a natural assignment scheme for HLGAGs. This is in direct contrast to the alphabetic codes used to represent the nucleotides of DNA and amino acids or proteins that serve as mere identifiers and do not code for any information (properties) and do not capture the chemical heterogeneity of these biopolymers.

The hexadecimal coding system comprises the alphanumerals 0-9 and A-F. Since the disaccharide unit has 4 positions viz. 2-O, N-, 3-O and 6-O that can be modified, it is straightforward to assign each of the four binary digit positions of the hexadecimal code to one of these chemical positions. In addition, since there are only two modifications possible at each position, (2-O, 3-O and 6-O can either be sulfated or free, and the N-position can be sulfated or acetylated *), the use of a binary system captures these modifications as simple on or off states. For example, if, within a given disaccharide unit, the 2-O position is sulfated, then it is assigned the binary value of 1. Conversely, if the 2-O position on a given disaccharide is unsulfated, then it is assigned the binary value of 0.

There are some rare HLGAG sequences with unsubstituted N-position, which can be accounted for in the PEN system by adding extra bits. However, in our studies, initial experiments including compositional analysis (see below) did not show the presence of free amine containing disaccharides.

To identify a disaccharide with an alphanumeric character, the 4 binary positions have been assigned in the following manner: the 2-O position was assigned the leftmost binary position, followed by the 6-O, 3-O and N-position in that order. In each case, as outlined above, the binary code 1 was used to represent sulfated positions and 0 was used to represent unsulfated positions in the case of 2-O, 6-O and 3-O, and acetylation in the case of N position.

To code for the isomeric state of the uronic acid (i.e., iduronic vs. glucuronic acid), we designated disaccharide units as +/−. In this way, it is possible to assign the positive hexadecimal codes to iduronic acid containing units and the negative hexadecimal codes to glucuronic acid containing units. Thus, disaccharide units with the same hexidecimal code but opposite signs possess the same sulfation pattern, differing only in the isomeric state of the uronic acid. Table 1 outlines the use of PEN for the disaccharide units present in this study.

TABLE 1

Derivation of PEN for Disaccharide Units Used in this Study

| I/G | 2X | 6X | 3X | NX | HEX | DISACC | MASS |
|---|---|---|---|---|---|---|---|
| 0 | 0 | 1 | 0 | 0 | 4 | I-$H_{NAc,6S}$ | 459.4 |
| 0 | 0 | 1 | 0 | 1 | 5 | I-$H_{NS,6S}$ | 497.4 |
| 0 | 1 | 1 | 0 | 1 | D | $I_{2S}$-$H_{NS,6S}$ | 577.5 |
| 1 | 0 | 1 | 0 | 1 | −5 | G-$H_{NS,6S}$ | 497.4 |
| 1 | 0 | 1 | 1 | 1 | −7 | G-$H_{NS,3S,6S}$ | 577.4 |

The hexadecimal code derived for the disaccharide units occurring in AT-10 are shown in Table 1. Column 1 is the binary position that codes for the isomeric state of the uronic acid. Columns 2 through 5 code for the modifications at the 2-O, 6-O, 3-O and N-positions of the disaccharide unit. Column 6 shows the hexadecimal codes represented by the binary digits in columns 2 through 5. Column 7 shows the disaccharide unit represented by the code in column 6. Column 8 shows the calculated theoretical masses of the disaccharide unit present internally in a sequence. For chemical or enzymatic modifications to these disaccharides, the following nomenclature is used: uronic acid with a $\Delta^{4-5}$ unsaturated linkage ($\Delta U$)=±; reducing end disaccharide unit with a mass tag=$^r$; disaccharide unit with a five-membered anhydromannose ring=$^t$.

sitional analysis is then used to determine the number and type of disaccharide building blocks. With this information, a master list is constructed of all possible sequences that contain those disaccharide units. In this manner, no sequences are excluded from the analysis, no matter how unusual a given sequence may be. The mass of oligosaccharide fragments generated from enzymatic digestion or chemical degradation are applied as experimental constraints and sequences that do not satisfy these constraints are eliminated. In an iterative manner, moving from experimental constraints to the ever-decreasing master list of possible sequences, one can rapidly arrive at a unique sequence solution using a minimum of material. Importantly, multiple pathways, using separate experimental constraints, can be used to converge on a sequence, ensuring assignment accuracy.

Analysis of AT-10

AT-10 and all oligosaccharides derived from it either upon enzymatic or chemical treatment are detected with MALDI-MS as non-covalent complexes with the basic peptide $(RG)_{19}R$ (Rhomberg, A. J., Ernst, S., Sasisekharan, R. & Biemann, K. (1998) *Proc Natl Acad Sci USA* 95, 4176-81 and Juhasz, P. & Biemann, K. (1995) *Carbohydr Res* 270, 131-47). Using this methodology, two species are observed, a $(M+H)^+$ ion of $(RG)_{19}R$ and a $(M+14)^+$ ion for the peptide: saccharide complex. The molecular mass of an oligosaccharide is obtained by subtracting the $(M+H)^+$ value of the peptide from the $(M+H)^+$ value of the 1:1 saccharide:peptide complex. Table 2 lists all fragments observed in this study, their calculated and experimentally derived mass values, and the deduced structure of the fragments after sequence assignment of AT-10. FIG. 1 shows that the major component of AT-10 has a m/z value of 6999.3. When the m/z value of the protonated peptide is subtracted, the experimental value for the mass of this oligosaccharide is found to be 2770.2 which can uniquely be assigned to a decasaccharide with 13 sulfates and 1 acetate group. The mass spectrum of AT-10 indicates the presence of another species (hereafter referred to as the contaminant) of mass 2690.1 (after subtraction of the peptide contribution), corresponding to an oligosaccharide with 12 sulfates and 1 acetate group.

TABLE 2 m/z values for the peaks in the mass spectra and their deduced structures

| Complex $(M + H)^+$ | Saccharide (Observed) | Deduced Structure | Mass (Calculated) |
|---|---|---|---|
| 6999.3 | 2770.2 | $\Delta U_{2S}H_{NS}[RS1]_{+6S}I_{2S}H_{NS,6S}I_{2S}H_{NS,6S}IH_{NAc,6S}GH_{NS,3S,6S}$ (FIG. 1) | 2769.3 |
| 6919.2 | 2690.1 | $\Delta U_{2S}H_{NS}[RS2]_{+6S}I/GH_{NS,6S}I_{2S}H_{NS,6S}IH_{NAc,6S}GH_{NS,3S,6S}$ (FIG. 1) | 2689.2 |
| 6899.6 | 2673.0 | $\Delta U_{2S}H_{NS}[RS3]_{+6S}I_{2S}H_{NS,6S}I_{2S}H_{NS,6S}IH_{NAc,6S}GMan_{3S,6S}$ (FIG. 4) | 2672.2 |
| 6435.8 | 2209.2 | $I_{2S}H_{NS}[RS4]_{+6S}I_{2S}H_{NS,6S}IH_{NAc,6S}GH_{NS,3S,6S}$ (FIG. 4) | 2209.8 |
| 6419.7 | 2192.2 | $\Delta U_{2S}H_{NS}[RS5]_{+6S}I_{2S}H_{NS,6S}IH_{NAc,6S}GH_{NS,3S,6S}$ (FIG. 2a) | 2191.8 |
| 6339.8 | 2113.2 | $I_{2S}H_{NS}[RS6]_{+6S}I_{2S}H_{NS,6S}IH_{NAc,6S}GMan_{3S,6S}$ (FIG. 4) | 2112.7 |
| 5899.9 | 1671.4 | $\Delta U_{2S}H_{NS}[RS7]_{+6S}IH_{NAc,6S}GH_{NS,3S,6S}d^*$ (mass tagged, FIG. 2c) | 1670.4 |
| 5859.8 | 1633.2 | $I_{2S}H_{NS}[RS8]_{+6S}IH_{NAc,6S}GH_{NS,3S,6S}$ (FIG. 4) | 1632.3 |
| 5842.1, 5842.2, 5843.6 | 1614.6, 1614.4, 1615.1 | $\Delta U_{2S}H_{NS}[RS9]_{+6S}IH_{NAc,6S}GH_{NS,3S,6S}$ (FIG. 2a, b, c) | 1614.3 |
| 5383.1, 5382.5 | 1155.6, 1154.0 | $\Delta U_{2S}H_{NS}[RS10]_{+6S}I_{2S}H_{NS,6S}$ (FIG. 2a, c) | 1154.9 |
| 5301.7 | 1073.9 | $\Delta U_{2S}H_{NS}[RS11]_{+6S}I/GH_{NS,6S}$ (FIG. 2b) | 1074.9 |
| 5284.5 | 1057.9 | $\Delta U_{2S}H_{NS}[RS12]_{+6S}I_{2S}Man_{6S}$ (FIG. 4) | 1057.8 |
| 5241.5 | 1013.8 | $IH_{NAc,6S}GMan_{3S,6S}d$ (mass tagged, FIG. 3) | 1013.9 |
| 5186.5 | 958.8 | $IH_{NAc,6S}GMan_{3S,6S}$ (FIG. 3) | 957.8 |
| 5007.8 | 780.8 | $H_{NAc,6S}GMan_{3S,6S}$ (FIG. 3) | 780.7 |
| 4805.2, 4805.3, 4805.2 | 577.7, 577.5 576.7 | $\Delta U_{2S}H_{NS}[RS13]_{+6S}$ (FIG. 2a, b, c) | 577.5 |

*d represents the semicarbazide mass tag ($\Delta$ = 56.1 daltons)

Thus, the strategy for the sequence assignment of HLGAG oligosaccharides by PEN-MALDI essentially involves the following steps. First, MALDI-MS of the intact oligosaccharide is used to assign the length as well as the total number of sulfates and acetates present in the oligosaccharide. Compo- Shown in column 1 is the m/z value of the protonated 1:1 complex of the saccharide and the basic peptide $(RG)_{19}R$. Column 2 shows the observed mass of the saccharide obtained by subtracting the value of the protonated peptide observed in the spectrum from the protonated 1:1 complex.

The deduced chemical structures of the saccharides for the corresponding peaks in the mass spectra are shown in column 3. Shown in column 4 are the theoretical masses calculated for the deduced structures. Note that the observed mass (col. 2) is always within ±1 dalton of the calculated mass (col. 4).

Compositional analysis using CE indicates the presence of four disaccharide building blocks, corresponding to $\Delta U_{2S}$-$H_{NS,6S}$ (±D). $\Delta U$-$H_{NAc,6S}$ (±4), $\Delta U$-$H_{NS,6S}$ (±5), and $\Delta U$-$H_{NS,3S,6S}$ (±7), in the relative ratio of 2.90:1.00:1.05:0.15 respectively. Thus, compositional analysis of this sample confirmed that there are two species, one major (~85%) and one minor (~15%). AT-10 must be a decasaccharide made of the building blocks $\Delta U_{2S}$-$H_{NS,6S}$ (±D), $\Delta U$-$H_{NAc,6S}$ (±4), and $\Delta U$-$H_{NS,3S,6S}$ (±7) in a ratio of 3:1:1. Together, the CE and MALDI-MS data was used to construct a master list of possible sequences for AT-10. We find that 320 sequences can account for both the CE and MS data (Table 2). These 320 sequences constitute the master list from which sequences were eliminated based on experimental constraints until convergence at a single solution.

In addition, the compositional analysis confirmed that there is a contaminant present that was structurally similar to AT-10, except for the presence of $\Delta U$-$H_{NS,6S}$ (±5). From the CE data, the composition of the contaminant was determined to be $\Delta U_{2S}$-$H_{NS,6S}$ (±D), $\Delta U$-$H_{NAc,6S}$ (±4), $\Delta U$-$H_{NS,3S,6S}$ (±7), and $\Delta U$-$H_{NS,6S}$ (±5) in the relative ratio of 2:1:1:1 from successive subtraction.

Having constructed the master list of sequence possibilities, a combination of PEN-MALDI, IGS (Turnbull, J. E., Hopwood, J. J. & Gallagher, J. T. (1999) *Proc Natl Acad Sci USA* 96, 2698-703), and NMR analysis was used to sequence AT-10 and then to analyze the sequence of the contaminant.

MALDI-MS Sequencing of AT-10

From the list of 320 possible sequences generated from the composition data, we have used a series of experimental constraints, including the use of heparinase I and nitrous acid, respectively, to assign the sequence of AT-10.

Figure 2A:
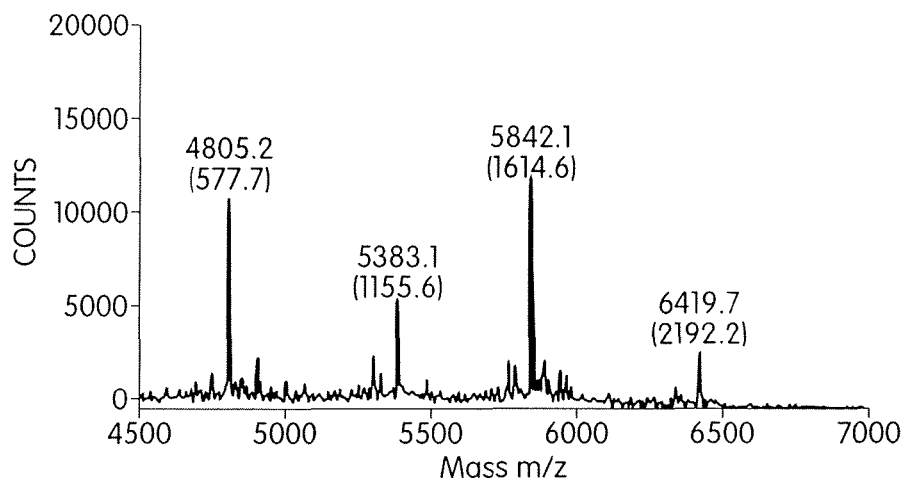
FIG. 2 depicts Heparinase treatment of AT-10. (A) Incomplete heparinase I treatment of AT-10. Under the conditions used in this study, heparinase I cleaves a glycosidic linkage containing an $I_{2S}$. (B) MALDI mass spectrum of AT-10 fragments from exhaustive digestion with heparinase I. (C) MALDI mass spectrum of tagged AT-10 treated with heparinase I shows five fragments: one with molecular mass of 576.7 Da (assignable to ±D), two tetrasaccharides with molecular mass of 1037.9 (*) and 1154.0 Da, and a mass tagged hexasaccharide with a molecular mass of 1671.4 (mass of 1615.3 plus the mass tag of 56.1). Since the coupling efficiency was ~90%, also seen is unlabeled hexasaccharide (mass of 1615.1).

Short (incomplete) digestion of AT-10 with heparinase I results in five fragments of molecular mass 577.7, 1073.9, 1155.6, 1614.6 and 2192.2 (FIG. 2a). The fragment with mass 577.7 corresponds to ±D. The 1155.6 fragment corresponds to a hexasulfated tetrasaccharide which has to have one of the following structures: ±DD, ±D-D, ±D7, ±D-7, ±7D, or ±7-D. The fragment with 1614.6 corresponds to a heptasulfated monoacetylated hexasaccharide and the fragment with 2192.2 corresponds to a decasulfated monoacetylated octasaccharide. The last peak, at 1073.9 was assigned unambiguously to the contaminant (see below for analysis). When the list of 320 sequences were searched for these fragments formed by simulated heparinase I digestion, it reduced the list to 52 sequences (Table 2).

Figure 2B:
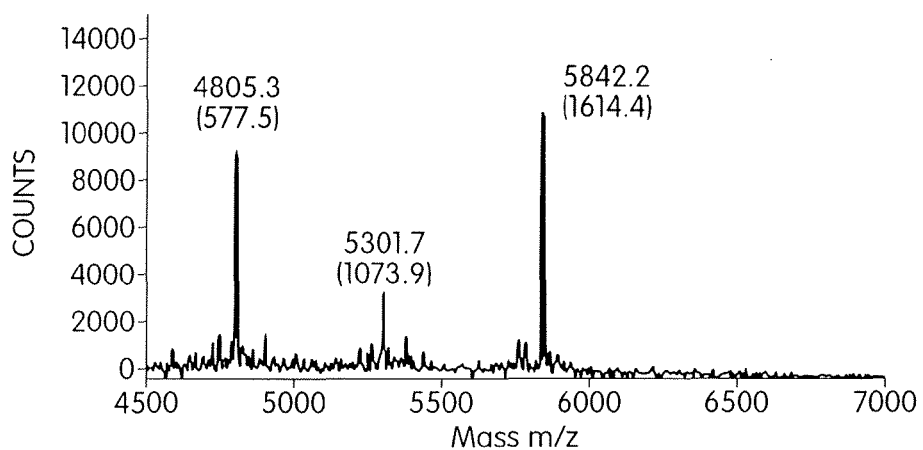

The rate of substrate cleavage by heparinase I is size dependent (Linhardt, R. J., Turnbull, J. E., Wang, H. M., Loganathan, D. & Gallagher, J. T. (1990) *Biochemistry* 29, 2611-7). To identify all 2-O sulfated iduronate-containing linkages in AT-10, it was treated with heparinase I under conditions that resulted in complete cleavage of all susceptible linkages. Under these conditions, the hexasaccharide and tetrasaccharide, from the contaminant, remained intact (FIG. 2b). However, the hexasulfated tetrasaccharide (mass of 1155.6 from FIG. 2a) was cleaved. Thus, this saccharide has the sequence ±DD. Of the 52 possible sequence assignments for AT-10, only 28 can satisfy the heparinase I exhaustive digest data.

Figure 2C:
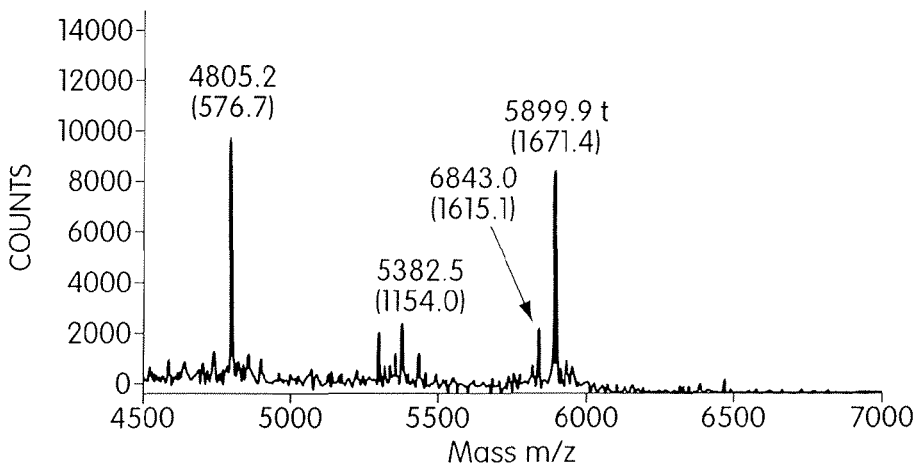

Next, AT-10 was treated with semicarbazide to yield a semicarbazone at the anomeric position. In this fashion a mass tag ($\Delta$=56.1) was introduced to differentiate fragments derived from the reducing end as opposed to the non-reducing end. Treatment of tagged AT-10 with heparinase I yielded five fragments (FIG. 2c). From a comparison of heparinase I-treated underivatized AT-10 (FIG. 2a), the heptasulfated monoacetylated hexasccharide appears tagged and thus must be derived from the reducing end of AT-10. Application of this constraint to the 28 remaining sequences eliminates all but 12 of them (Table 3)

TABLE 3

Convergence of the AT-10 sequence

| | Fragments observed with their masses | | |
|---|---|---|---|
| Sequences | (577) | (1154) | (1671) |
| ±DDD47' | ±D | ±DD | ±D47' |
| ±DDD-47' | ±D | ±DD | ±D-47' |
| ±DDD4-7' | +D | ±DD | ±D4-7' |
| ±DDD-4-7' | ±D | ±DD | ±D-4-7' |
| ±DDD74' | ±D | ±DD | ±D74' |
| ±DDD7-4' | ±D | ±DD | ±D7-4' |
| ±DDD-74' | ±D | ±DD | ±D-74' |
| ±DDD-7-4' | ±D | ±DD | ±D-7-4' |
| ±7DD4-D' | ±7 | ±7D | ±D4-D' |
| ±7DD-4-D' | ±7 | ±7D | ±D-4-D' |
| ±7DD-D4' | ±7 | ±7D | ±D-D4' |
| ±7DD-D-4' | ±7 | ±7D | ±D-D-4' |

320 → Hep-I (short) → 52 → Hep-I (long) → 28 → Hep-I (tagged long)

Exhaustive Nitrous Acid

| Sequences observed | Fragments with their masses (996) |
|---|---|
| ±DDD47' | +47" |
| ±DDD-47' | -47" |
| ±DDD4-7' | +4-7" |
| ±DDD-4-7' | -4-7" |
| ±7DD4-D' | +4-D' |
| ±7DD-4-D' | -4-D' |

The stepwise strategy used to sequence the decasaccharide sample is shown in Table 3. Application of experimental constraints to eliminate the sequences from the master list of 320 * sequences was used to converge to the final sequence. Shown in the boxes on the left is the number of sequences that satisfied the experimental constraints. The boxes on the right show the sequences that satisfy the experimental constraints along with the possible fragments formed for the masses shown in parenthesis on the top of the table.

* To obtain all the possible decasaccharides with the composition of 3±Ds, a ±4 and a ±7 we need to arrange the above disaccharide units in all the possible ways, to form a decasaccharide. Also each disaccharide unit can be a + or a − corresponding to iduronate or glucuronate. The number of possible sequences=$^5C_3$ (arrange 3Ds in 5 positions)*$^2C_1$ (arrange the 4 in the two remaining positions)*$2^4$ (to account for the + or − at all the positions except the non-reducing end, since the saccharide is heparinase derived)=10*2*16=320.

Figure 3:
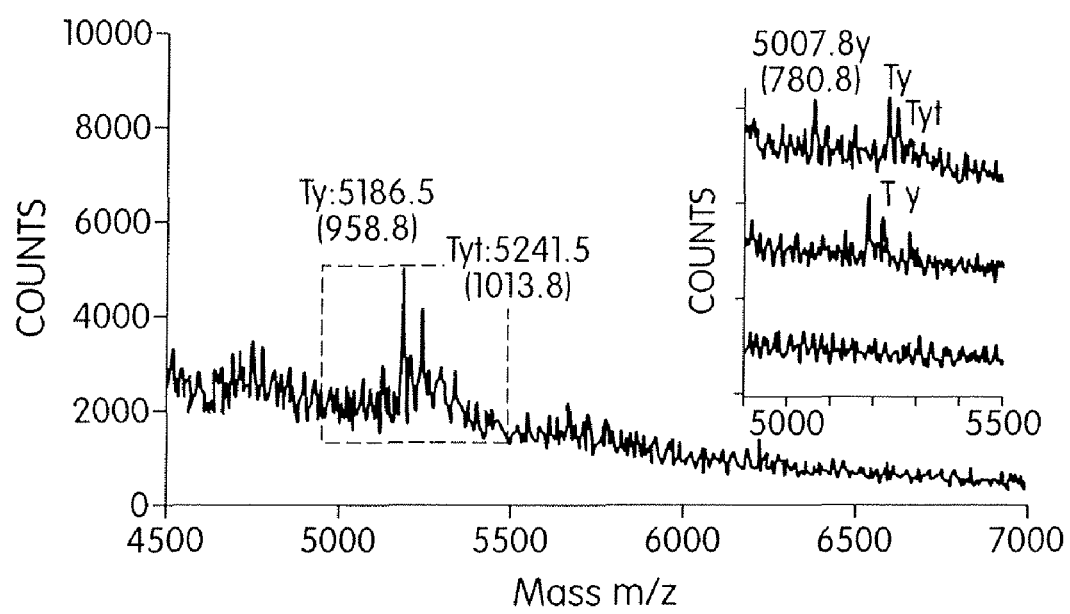
FIG. 3 depicts exhaustive degradation of AT-10 with nitrous acid. Nitrous acid cleaves at $H_{NS}$ residues, leaving behind an anhydromannose (Δ=97.1 Da). Shown in the inset is the mass spectrum of the degradation profile when the sample was treated with iduronidase (top), glucosamine 6-O sulfatase (middle) and glucuronidase (bottom) in that order.

Inspection of the 12 remaining sequences in Table 3 indicates that the primary difference is in the identity of the reducing-end hexasaccharide. Therefore, through nitrous acid degradation of AT-10 and judicious use of exoenzymes, the sequence of the reducing end tetrasaccharide was determined. First, tagged AT-10 was exhaustively treated with nitrous acid and two species were readily detectable (FIG. 3). The first, with a mass of 1013.8, corresponds to a tagged anhydromannose tetrasaccharide with four sulfates and one acetate. The other with a mass of 958.8 corresponds to the same tetrasaccharide that is untagged. Both could be assigned to one of the following sequences: ±47, ±4-7, ±4-D. Thus, based on this information, half of the possible sequences could be eliminated, leaving only 6 possible sequence solutions for AT-10 (Table 3).

To assign uniquely the isomeric state of the two disaccharide units at the reducing end of AT-10, the following experimental constrains were used: the exhaustive nitrous acid digest was incubated with the exolytic enzyme α-iduronidase that specifically clips the iduronic acid at the non-reducing end. A shift in the spectrum by 178.0 confirmed the uronic acid as 4 and its isomeric state as +, i.e., $IH_{NAc,6S}$ or +4. Only 3 sequences could give the observed fragments, viz., ±7DD4-D, ±DDD4-7, ±DDD47.

To distinguish among these last three alternatives and to identify the reducing end disaccharide, the iduronidase-treated product was first treated with 6-O sulfatase and N-deacetylase to remove the hexosamine, leaving only the reducing end disaccharide. Treatment of this sample with β-glucuronidase resulted in degradation to monosaccharides. This identified the reducing end disaccharide as −7 (G-$H_{NS,3S,6S}$). Thus the deduced sequence of the AT-III fractionated decasaccharide is ±DDD4-7 ($\Delta U_{2S}H_{NS,6S}I_{2S}H_{NS,6S}I_{2S}H_{NS,6S}IH_{NAc,6S}GH_{NS,3S,6S}$). Of note is the fact that this sequence does not agree with the sequence assignment for a decasaccharide produced in an identical manner (Toida, T., Hileman, R. E., Smith, A. E., Vlahova, P. I. & Linhardt, R. J. (1996) *J Biol Chem* 271, 32040-7). Therefore, we sought to confirm our sequencing assignment using other analytical methodologies.

IGS Sequencing of AT-10.

AT-10 was also sequenced using the recently established technique Integral Glycan Sequencing (IGS), which employs an electrophoretic separation of saccharides tagged at the reducing end with a fluorophore. Partial nitrous acid cleavage and exoenzyme digestion of the saccharide produces a ladder from which the sequence can be determined. In accord with the PEN-MALDI data, electrophoretic analysis of the fluorophore-tagged sample produced a single major decasaccharide, but in addition, the smaller contaminant was also evident. The products of partial nitrous acid cleavage were deca-, octa-, hexa-, and tetrasaccharides, with no disaccharide products observed. This result defines the positions of all of the NS and NAc moieties, with just one N-acetylated disaccharide in the position proximate to the reducing end. Gel shifts due to treatment of these products with different combinations of exoenzymes demonstrated iduronate residues in 3 positions, 2 of which were 2-O-sulfated, and the presence in three positions of 6-O-sulfated glucosamine residues. The non-reducing end was clearly 2-O-sulfated but confirmation of the presence a 6-O-sulfate on the non-reducing end glucosamine residue, and details of the sulfation pattern on the reducing end monosaccharide were not obtained in this analysis. This data defines the structure of the AT-10 as $\Delta U_{2S}H_{NS,\pm 6S}I_{2S}H_{NS,6S}I_{2S}H_{NS,6S}IH_{NAc,6S}GH_{NAc/NS,\pm 3S,\pm 6S}$ This data, derived from an independent sequencing approach, is entirely consistent with the PEN-MALDI analysis.

Sequence Analysis of AT-10 Contaminan

The mass spectral data can also be used in conjunction with the CE compositional analysis to arrive at a proposed sequence for the 12 sulfated, 1 acetylated contaminant of AT-10. As stated above, heparinase I digest (FIG. 2a) yielded a peak at m/z of 1073.9 that corresponds to a pentasulfated tetrasaccharide (±D±5, ±7±5, or ±5±7), that is assignable only to the contaminant. This tetrasaccharide fragment was not derived from the reducing end of the contaminant since under no conditions was a labeled saccharide containing ±5 found. In addition, a heparinase I digest of tagged decasaccharide places 4-7 at the reducing end for both the contaminant as well as for AT-10. To place the position of the D5 or D-5 tetrasaccharide observed in the heparinase I digest the decasaccharide was treated with iduronate 2-O prior to heparinase I treatment. Under these conditions, the pentasulfated tetrasaccharide reduced in mass by 80 Da (from mass of 1073.9 to 993.9, resulting from the loss of sulfate). Therefore, this tetrasaccharide must be derived from the non-reducing end of the contaminant. Together, this information suggests that the sequence of the contaminant is ±D5D4-7 or ±D-5D4-7.

Figure 4:
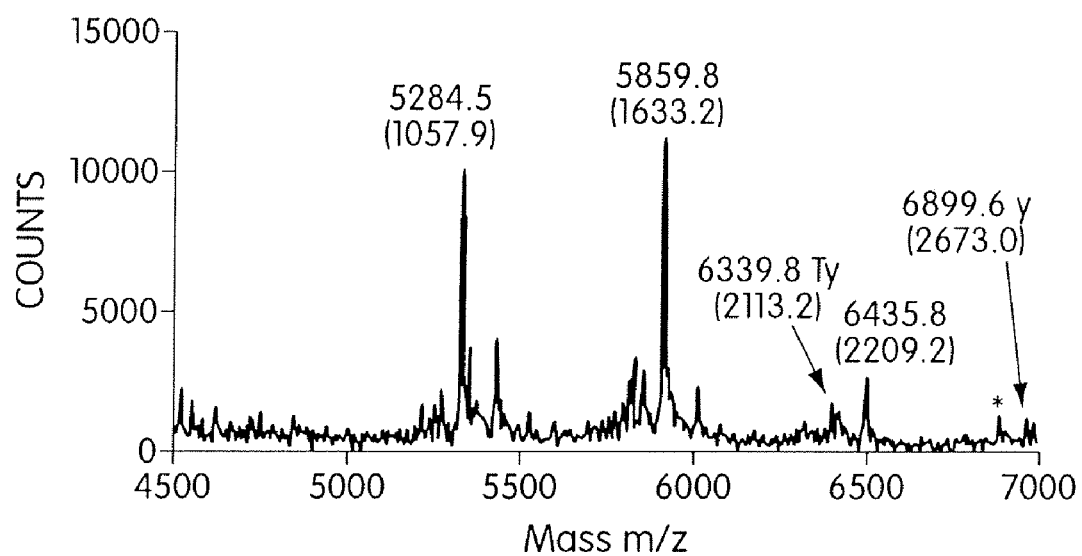
FIG. 4 is a MALDI mass spectrum showing partial nitrous acid degradation of AT-10.

The assignment for AT-10 and the contaminant was confirmed when the decasaccharide was incompletely degraded with nitrous acid (FIG. 4). AT-10 with an anhydromannose at the reducing end (mass of 2673.0) is clearly observed as are fragments resulting from nitrous acid scission (masses of 2209.2, 2113.2 and 1633.2) of AT-10. In addition, a species with mass 1057.9 can only be obtained from $\Delta U_{2S}H_{NS,6S}I_{2S}Man_{6S}$, providing a unique mass signature of the non-reducing end of AT-10. Importantly, all of the species could be assigned to either AT-10 or the contaminant.

Interpretation of NMR Spectrum of AT-10

Figure 6A:
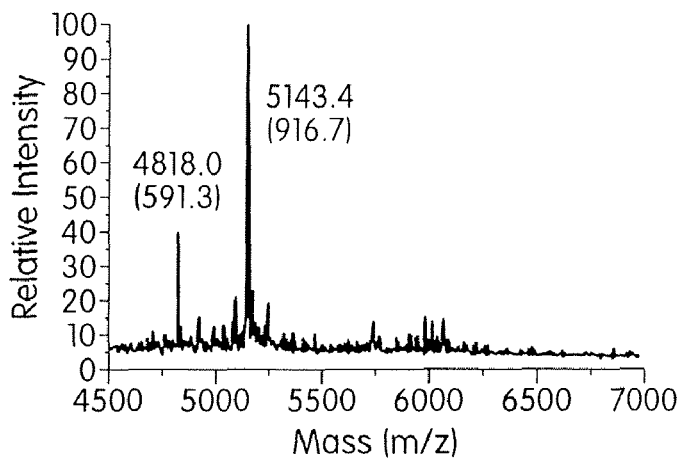
FIG. 6 is a MALDI mass spectra of (A) heparinase I, (B) heparinase II, and (C) heparinase III digestion products of Penta 1. Both heparinase I and II clip Penta 1 at the $G_{NS,3S,6S}\!\!\downarrow\!\!I_{2S}H_{NS,6S}$ linkage (site A.2) to yield a pentasulfated trisaccharide and a trisulfated disaccharide product. Penta 1 is not cleavable by heparinase III.
Figure 6B:
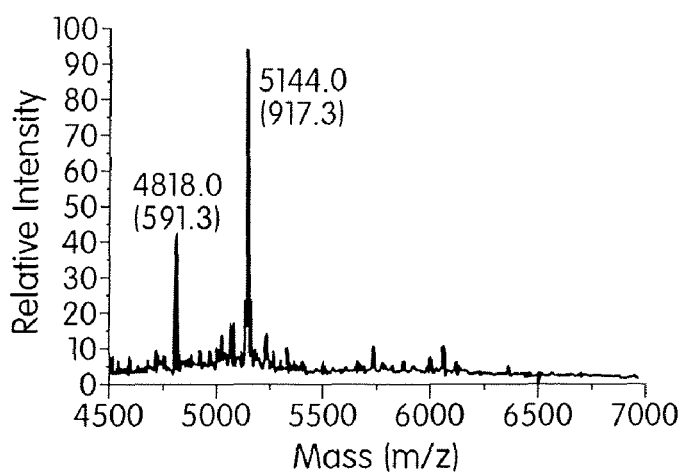
Figure 6C:
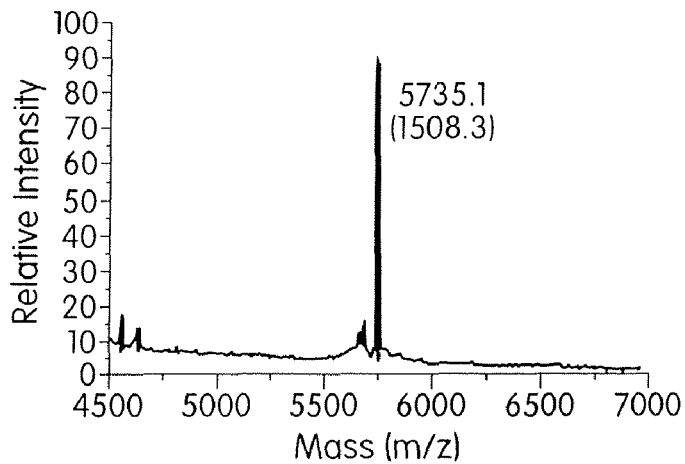

The NMR spectrum of AT-10 is shown in FIG. 6. Consistent with our analysis, the small signals of αH-1, αH-2 and αH-3 of $H_{NS,3S,6S}$ (at 5.45, 3.45 and 4.50 ppm, respectively) allow us to assign the reducing end monosaccharide unit as $H_{NS,3S,6S}$. In this case, the anomeric proton of the reducing end $H_{NS3S6S}$ residue must be split into α and β-configurations. The α-configuration of the anomeric proton of the $H_{NS}$ residue is dominant (~95%) in protic solvents, such as deuterium oxide, based on the anomeric effect. Furthermore, the presence of two $I_{2S}$ moieties could be detected. Interestingly, the anomeric signals of the two $I_{2S}$, which usually resonate around 5.20 ppm, were shifted. This most probably results from a change in the conformation of the internal $I_{2S}$ moiety from $^1C_4$ to $^2S_0$. Also, it could be confirmed that the oligosaccharide contains three $H_{NS,6S}$ and one unsulfated G residue based on the integration values of H-2 protons of $H_{NS,6S}$ and G residues observed at 3.28 and 3.38 ppm, respectively. The presence of one N-acetyl methyl signal of $H_{NAc,6S}$ residue at 2.1 ppm clearly demonstrates that the oligosaccharide contains one $H_{NAc,6S}$ residue. The presence of signals corresponding to the H-6 protons of 6-O-sulfated $H_{NY}$ residues (Y=Ac or S) at around 4.3 and 3.9 ppm, confirms that all $H_{NY}$ residues of the oligosaccharide are O-sulfated at C-6. Together, this data allows the sequence assignment of the major species in the AT-10 sample as $\Delta U_{2S}H_{NS,6S}I_{2S}H_{NS,6S}I_{2S}H_{NS,6S}IH_{NAc,6S}GH_{NS,3S,6S}$.

SUMMARY

It has been shown in this Example that several rigorous analytical techniques can be used to converge on the structure of a complex HLGAG oligosaccharide. Furthermore, it was demonstrated that the sequence assignment using the two sequencing procedures, viz., IGS and PEN-MALDI is the same. This is most apparent in the partial and exhaustive nitrous acid treatment of the decasaccharide (FIG. 3). Importantly, from our analysis it now becomes possible to assign the following sequences to the deca, octa, hexa, and tetrasaccharides observed upon gel electrophoresis and MALDI-MS, viz. DDD4-7, DD4-7, D4-7, and a nitrous acid resistant tetrasaccharide 4-7. In the next Example, the functional consequences of a partially intact AT-III binding site was explored and the enzymatic action of the heparinases towards the AT-III binding site (Shriver, Z., Sundaram, M., Venkataraman, G., Fareed, J., Linhardt, R. J., Biemann, K., & Ram Sasisekharan (2000)) was defined.

In addition, it was demonstrated that the PEN-MALDI approach is sufficiently sensitive and discriminating to allow us to determine sequence information for a oligosaccharide mixture. It is essential to point out the fact that convergence to a single solution for AT-10 using PEN-MALDI is possible using multiple orthogonal experimental constraints (Venkataraman, G., Shriver, Z., Raman, R. & Sasisekharan, R. (1999) Science 286, 537-42), thus minimizing reliance on a single experimental constraint, e.g., nitrous acid cleavage. Finally, the example shown illustrates the value of PEN-MALDI for obtaining definitive sequence information for biologically and pharmacologically relevant oligosaccharides.

Example 2

Cleavage of the Antithrombin III Binding Site in Heparin by Heparinases and its Implication in the Generation of Low Molecular Weight Heparin Introduction:

Heparin has been used as a clinical anticoagulant for over 50 years, making it one of the most effective pharmacological agents known. Much of heparin's activity can be traced to its ability to bind antithrombin III (AT-III). Low molecular weight heparin (LMWH), derived from heparin by its controlled breakdown, maintains much of the antithrombotic activity of heparin without many of the serious side effects. The clinical significance of LMWH has highlighted the need to understand and develop chemical or enzymatic means to generate it. The primary enzymatic tools used for the production of low molecular weight heparin are the heparinases from *Flavobacterium heparinum*, specifically heparinases I and II. Using pentasaccharide and hexasaccharide model compounds, we show that heparinase I and II, but not heparinase III, cleave the AT-III binding site. Furthermore, we show herein that glucosamine 3-O sulfation at the reducing end of a glycosidic linkage imparts resistance to heparinase I, II and III cleavage. Finally, we examine the biological and pharmacological consequences of a heparin oligosaccharide. We show that such an oligosaccharide lacks some of the functional attributes of HLGAG containing an intact AT-III site.

Methods:

Materials. Penta 1 and 2 was a generous gift of Dr. Robert Rosenberg, Department of Biology, MIT. Hexa 1 was generated using heparinase I digestion of heparin (Ernst, S., Langer, R., Cooney, C. L. & Sasisekharan, R. (1995) *Crit Rev Biochem Mol Biol* 30, 387-444). Heparin was purchased from Celsus Laboratories (Cincinnati, Ohio) and molar concentrations of stocks were calculated based on an average molecular weight of 13,000 Da. Enoxaparin was purchased from Avantis Pharmaceuticals, (Chicago, Ill.).

Digests. Heparinase I digests were completed as described (Venkataraman, G., Shriver, Z., Raman, R. & Sasisekharan, R. (1999) *Science* 286, 537-42 and Rhomberg, A. J., Ernst, S., Sasisekharan, R. & Biemann, K. (1998) *Proc Natl Acad Sci USA* 95, 4176-81). Heparinase II or III reactions were completed in essentially the same way at room temperature in 10 µM ovalbumin, 1 µM dextran sulfate, and 10 mM ethylenediamine, pH 7.0. Short digestions were completed with 50 nM enzyme for 10 minutes while exhaustive digests were completed with 200 nM enzyme overnight. Mass spectra were collected using parameters as outlined above (see also Shriver, Z., Raman, R., Venkataraman, G., Drummond, K., Turnbull, J., Toida, T., Linhardt, R., Biemann, K. & Sasisekharan, R. (2000) *Proc Natl Acad Sci USA*, 2000 Sep. 12; 97(19):10359-64) and calibrated externally by using signals for protonated $(RG)_{19}R$ and its complex with a nitrous acid-derived hexasaccharide of the sequence $I_{2S}H_{NS,6S}$ $I_{2S}H_{NS,6S}$ $I_{2S}Man_{6S}$ Equilibrium Fluorescence Titration Experiments. Titrations of human AT-III with either AT-10 decasaccharide or heparin were completed at 25° C. using a Fluorolog 2 machine (Spex Instruments) (Meagher, J. L., Beechem, J. M., Olson, S. T. & Gettins, P. G. (1998) *J Biol Chem* 273, 23283-9 and Desai, U. R., Petitou, M., Bjork, I. & Olson, S. T. (1998) *J Biol Chem* 273, 7478-87). Measurements were completed in 20 mM sodium phosphate, containing 0.1 mM EDTA and 0.1% PEG 8000, adjusted to either pH 7.4 or 6.0. With the pH 7.4 buffer, sodium chloride was added to a final concentration of 100 mM.

Fluorescence emission spectra were collected from 300-400 nm with a 280 nm excitation wavelength and a 5 s integration time. Briefly, the titration experiments were conducted as follows—aliquots of either decasaccharide or heparin was added to a 1 µm solution of AT-III, the solution was allowed to come to equilibrium for one minute, and an emission spectrum collected. Addition of sequential saccharide aliquots and fluorescence signal was adjusted to account for protein dilution.

Biological Measurements of Decasaccharide Activity. In vitro anticoagulant activity was determined as described previously (Hoppensteadt, D. A., Jeske, W. P., Walenga, J. M., Fu, K., Yang, L. H., Ing, T. S., Herbert, J. M. & Fareed, J. (1999) *Thromb Res* 96, 115-24 and Dietrich, C. P., Paiva, J. F., Castro, R. A., Chavante, S. F., Jeske, W., Fareed, J., Gorin, P. A., Mendes, A. & Nader, H. B. (1999) *Biochim Biophys Acta* 1428, 273-83), according to the United States Pharmacopoeia. Thrombin (FIIa) and factor Xa (FXa) generation inhibition assays were completed essentially as described. Briefly, either AT-10 decasaccharide, Enoxaparin LMWH or the synthetic AT-III binding pentasaccharide (Penta 1) used in this study was dissolved in sterile saline at the designated concentrations. To this sample was added an equal volume of fibrinogen deficient plasma diluted 1:8 in 100 mM Tris-HCl (pH 8.5). In a separate sample, the same concentration of heparin oligosaccharide and actin was added in a 1:1 ratio to either Spectrozyme TH or FXa. In this manner, the intrinsic IIa and Xa generation was measured. In addition, to account for inhibition of thrombin and extrinsic generation of FXa, thromboplastin C was diluted 1:6 with either Spectrozyme TH or FXa. For all samples, the optical density was measured at 405 nm and results are expressed as a % inhibition compared to a unsupplemented saline control. For these assays, thrombin reagent (Fibrindex) was obtained from Ortho Diagnostic Systems, Inc. (Raritan, N.J.), and factor Xa was obtained from Enzyme Research (South Bend, Ind.). Spectrozyme TH and FXa were obtained from American Diagnostica (Greenwich, Conn.).

Whole blood data were also used to determine the anticoagulant activity of AT-10. The assays, activated partial thromboplastin time (APTT) and prothrombin time (PT) was conducted in a manner similar to what has been previously reported (Dietrich, C. P., Paiva, J. F., Castro, R. A., Chavante, S. F., Jeske, W., Fareed, J., Gorin, P. A., Mendes, A. & Nader, H. B. (1999) *Biochim Biophys Acta* 1428, 273-83). APTT reagent was obtained from Organon Teknika (Durham, N.C.) and HepTest Reagent was obtained from Haemachem (St. Louis, Mo.).

Figure 5:
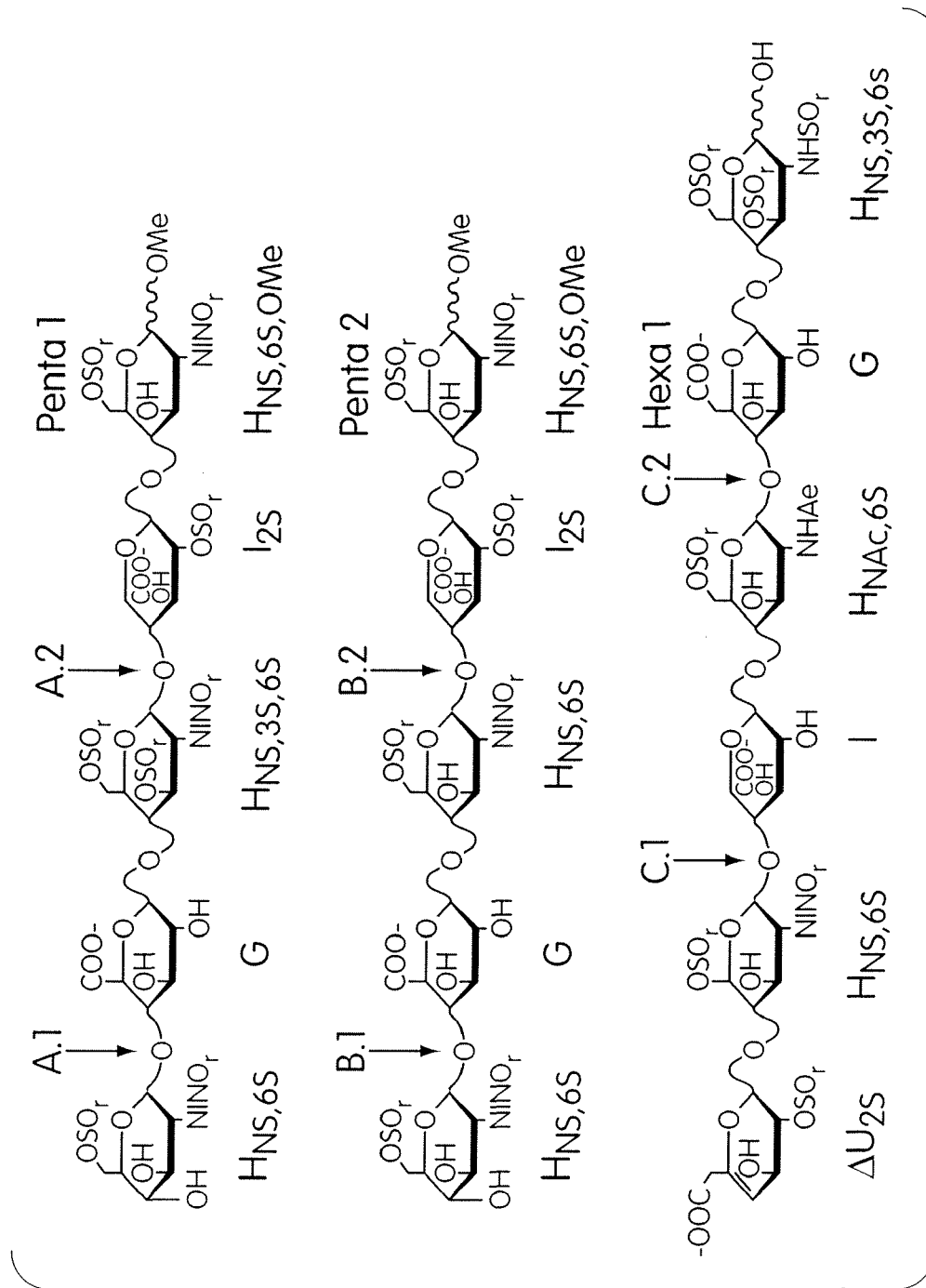
FIG. 5 shows the structures of the three oligosaccharide model compounds used in this study. (A) Pentasaccharide 1 (Penta 1) has the sequence $H_{NS,6S}GH_{NS,3S,6S}I_{2S}H_{NS,6S,OMe}$, contains a fully intact AT-III binding site and has a calculated molecular mass of 1508.2. The two glycosidic linkages potentially susceptible to heparinase I, II, or III cleavage are labeled A.1 and A.2. (B) Pentasaccharide 2 (Penta 2), with the sequence $H_{NS,6S}GH_{NS,6S}I_{2S}H_{NS,6S,OMe}$ and a calculated molecular mass of 1428.1, is structurally identical to Penta 1, less a 3-O sulfate on the internal glucosamine, thus it does not contain a full AT-III site. As with Penta 1 the bonds potentially susceptible to heparinase cleavage are marked B.1 and B.2. (C) A heparinase-derived hexasaccharide (Hexa 1), with the sequence $\Delta U_{2S}H_{NS,6S}IH_{NAc,6S}, GH_{NS,3S,6S}$, was also used in this study. Hexa 1 (calculated molecular mass 1614.3) contains only a partially intact AT-III binding site; similar to AT-10 it is missing the reducing end $I_{2S}H_{NS,6S}$ disaccharide unit. As with Penta 1 and Penta 2, sites of potential cleavage are marked C.1, C.2.
Figure 7A:
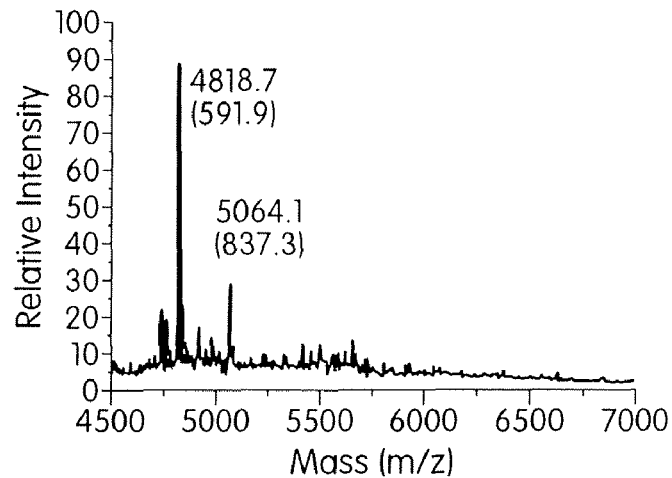
FIG. 7 is a MALDI mass spectra of (A) heparinase I, (B) heparinase II, and (C) heparinase III digestion products of Penta 2 complexed with $(RG)_{19}R$.
Figure 7B:
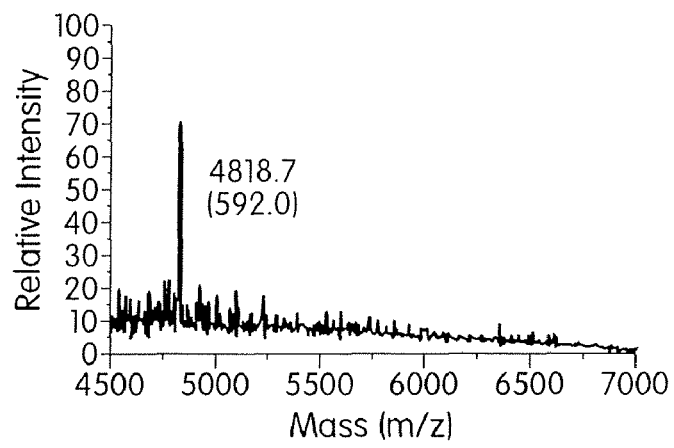
Figure 7C:
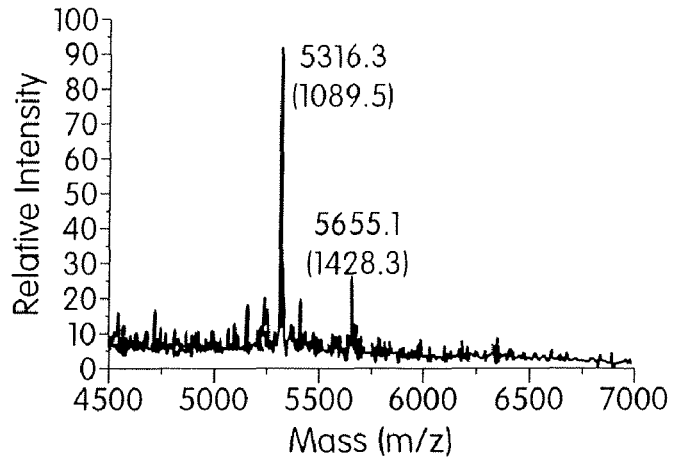

Results:

Enzymatic Action of the Heparinases Towards the AT-III Binding Site: Previously, we investigated the substrate specificity of heparinases I and II towards AT-10 (Rhomberg, A. J., Shriver, Z., Biemann, K. & Sasisekharan, R. (1998) Proc Natl Acad Sci USA 95, 12232-7 and Ernst, S., Rhomberg, A. J., Biemann, K. & Sasisekharan, R. (1998) *Proc Natl Acad Sci USA* 95, 4182-7). These studies, however, were carried out assuming a published structure (Toida, T., Hileman, R. E., Smith, A. E., Vlahova, P. I. & Linhardt, R. J. (1996) *J Biol Chem* 271, 32040-7). In light of the newly determined structure of AT-10 described herein (see also Shriver, Z., Raman, R., Venkataraman, G., Drummond, K., Turnbull, J., Toida, T., Linhardt, R., Biemann, K. & Sasisekharan, R. (2000) *Proc Natl Acad Sci USA*, 2000 Sep. 12; 97(19):10359-64), we reexamined the enzymatic action of heparinases I, II, and III towards oligosaccharides containing a 3-O sulfate that is critical for high affinity AT-III binding. For these studies, we used three oligosaccharides, two pentasaccharides (Penta 1 and Penta 2, FIG. 5) and a hexasaccharide (Hexa 1, FIG. 5). Of note is the fact that the pentasaccharides are synthetically derived whereas Hexa 1 is derived from treatment of heparin by heparinase I. As a result, unlike Penta 1 or Penta 2, Hexa 1 contains a $\Delta^{4,5}$ uronic acid at the non-reducing end. Furthermore, Penta 1 and Penta 2 differ from one another only by the presence (Penta 1) or absence (Penta 2) of a 3-O sulfate on the internal glucosamine residue (FIG. 5). The strategy employed herein essentially involves treatment of each of the saccharides with heparinase I, II, or III, respectively, under exhaustive digestion conditions, followed by the identification of the resulting products by mass spectrometry. The calculated mass of the saccharide substrates and products, their identity, and the observed mass is listed in Table 4.

trisaccharide of mass 916.7 and a trisulfated disaccharide of mass 591.3 (FIG. 6), indicative of cleavage at the $I_{2S}$-containing glycosidic linkage (linkage A.2 in FIG. 5). The data presented in FIG. 6 show that 3-O containing linkages are resistant to heparinase I, II or III cleavage. This resistance appears to be length independent. Based-on the previous understanding of the structure of AT-10 (Toida, T., Hileman, R. E., Smith, A. E., Vlahova, P. I. & Linhardt, R. J. (1996) *J Biol Chem* 271, 32040-7), it was reported that heparinase II could cleave a 3-O sulfate containing saccharide provided that it was of sufficient length (Rhomberg, A. J., Shriver, Z., Biemann, K. & Sasisekharan, R. (1998) *Proc Natl Acad Sci USA* 95, 12232-7). In light of the newly determined structure for the AT-10 decasaccharide (See also Shriver, Z., Raman, R., Venkataraman, G., Drummond, K., Turnbull, J., Toida, T., Linhardt, R., Biemann, K. & Sasisekharan, R. (2000) *Proc Natl Acad Sci USA*, 2000 Sep. 12; 97(19):10359-64), as well as the data presented in FIG. 6, the previous findings must be reinterpreted and it is concluded herein that heparinase II does not cleave linkages with a reducing-end proximate 3-O sulfated glucosamine. In addition, resistance of this linkage to heparinase I, II and III action is entirely due to the presence of a 3-O sulfate as shown by heparinase I, II, and III treatment of Penta 2 (FIG. 7). In this case, all of the heparinases efficiently cleave the substrate. As with Penta 1, heparinase I cleaves at the $I_{2S}$-containing linkage yielding a trisaccharide of mass 837.3 and a disaccharide of mass 591.9 (cleavage at linkage B.2 in FIG. 5). Conversely, both heparinase II and III cleave at the now scissile unsulfated G-containing linkage (linkage B.1 in FIG. 5). Heparinase III cleaves only this linkage giving a tetrasaccharide of mass 1428.3 and a monosaccharide (not observed). Heparinase II cleaves at linkage B.2 as well as B.1, reducing Penta 2 to a monosaccharide and two disaccharides, one of which his observed and has a mass of 592.0 (FIG. 7).

Figure 8A:
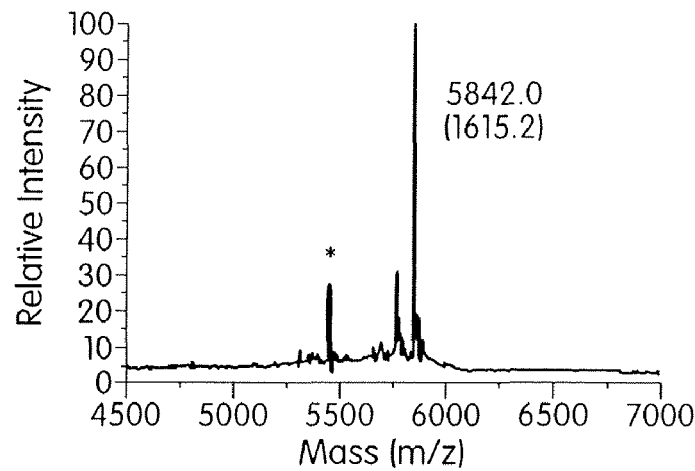
FIG. 8 is a MALDI mass spectra of (A) heparinase I, (B) heparinase II, and (C) heparinase III digestion products of Hexa 1 complexed with $(RG)_{19}R$.
Figure 8B:
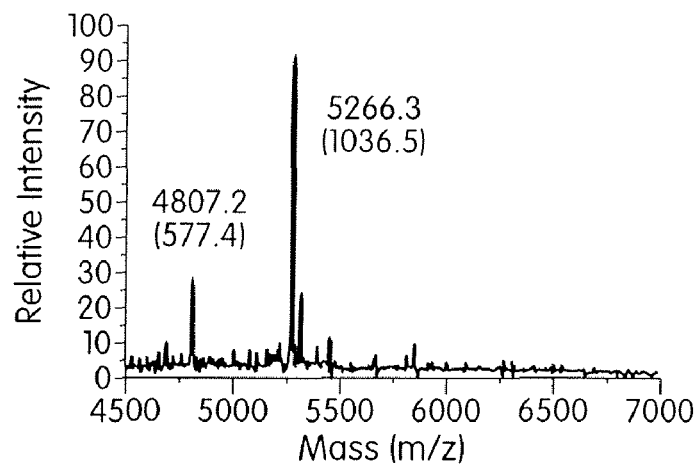
Figure 8C:
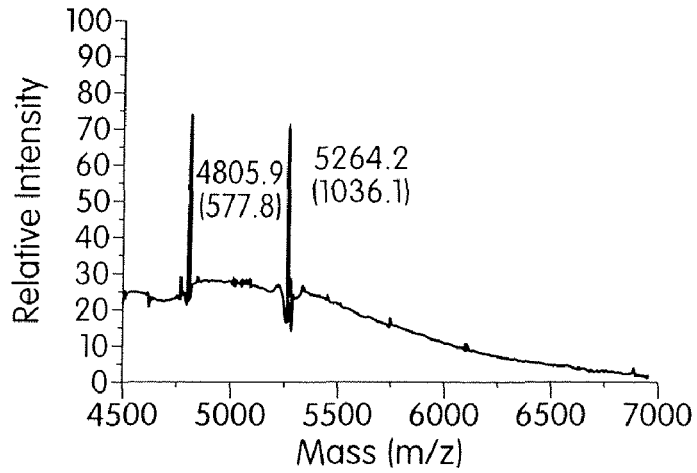

To explore further the substrate specificity of the heparinases towards the 3-O sulfated saccharides, we used Hexa 1, a 3-O sulfate-containing, heparinase I-derived hexasaccharide (FIG. 8). Hexa 1 was also chosen as a substrate for this study because it represents a non-reducing end truncation of

TABLE 4

Chemical structures and m/z values of the HLGAG oligosaccharides

| Complex (M + H)⁺ | Saccharide (mass) | Chemical Structure | Mass (Calculated) |
|---|---|---|---|
| 5842.0 | 1615.2 | $\Delta U_{2S}H_{NS[RS14],6S}IH_{NAc,6S}GH_{NS,3S,6S}$ | 1614.3 |
| 5735.1 | 1508.3 | $H_{NS[RS15],6S}GH_{NS,3S,6S}I_{2S}H_{NS,6S,OMe}$ | 1508.2 |
| 5655.1 | 1428.3 | $H_{NS[RS16],6S}GH_{NS,6S}I_{2S}H_{NS,6S,OMe}$ | 1428.1 |
| 5316.3 | 1089.5 | $\Delta UH_{NS}[RS17],_{6S}I_{2S}H_{NS,6S,OMe}$ | 1088.9 |
| 5266.3, 5264.2 | 1036.5, 1036.1 | $\Delta UH_{Nac}[RS18],_{6S}GH_{NS,3S,6S}$ | 1036.9 |
| 5064.1 | 837.3 | $H_{NS,6S}GH_{NS,6S}$ | 836.7 |
| 5143.4, 5144.0 | 916.7, 917.3 | $H_{NS,6S}GH_{NS,3S,6S}$ | 916.8 |
| 4818.0, 4818.0, 4818.7, 4818.7 | 591.3, 591.3, 591.9, 592.0 | $\Delta U_{2S}H_{NS[RS19],6S,OMe}$ | 591.5 |
| 4807.2, 4805.9 | 577.4, 577.8 | $\Delta U_{2S}H_{NS}[RS20],_{6S}$ | 577.5 |

Shown in column 1 of Table 4 is the m/z value of the protonated 1:1 complex of the saccharide and the basic peptide $(RG)_{19}R$. Column 2 shows the observed mass of the saccharide obtained by subtracting the mass of protonated basic peptide from the protonated 1:1 complex. The chemical structures of the saccharides for the corresponding peaks in the mass spectra are shown in column 3. Column 4 shows the theoretical masses calculated for the chemical structures. Note that the observed mass is within ±1 Da of the calculated mass.

In the case of Penta 1, only heparinase I and II, but not heparinase III, cleave the oligosaccharide into a pentasulfated AT-10 and contains the same $GH_{NS,3S,6S}$ moiety at the reducing end. We find that hexa 1 is susceptible to heparinase II and III cleavage but not heparinase I scission. Of note is the fact that cleavage of Hexa 1 by either heparinase II or III does not occur at the G-containing linkage but rather at the I-containing linkage (cleavage at C.1 but not C.2 in FIG. 5). In the case of heparinase II cleavage, the products are a tetrasaccharide of mass 1036.5 and a disaccharide of mass 577.4. For heparinase III cleavage, the same products are observed, viz.; a tetrasaccharide of mass 1036.1 and a disaccharide of mass 577.8. These results confirm our assessment that linkages with a reducing end proximate 3-O sulfate are protected from heparinase action, including heparinase II. With both heparinase II and III treatment of Hexa 1, a heparinase-resistant tetrasaccharide, with the sequence $\Delta UH_{NAc,6S}GH_{NS,3S,6S}$ is formed. That this tetrasaccharide is resistant to further heparinase cleavage is consistent with previous observations (Yamada, S., Yoshida, K., Sugiura, M., Sugahara, K., Khoo, K. H., Morris, H. R. & Dell, A. (1993) *J Biol Chem* 268, 4780-7). Also consistent with the known substrate specificity of heparinase I, Hexa 1, which contains no $I_{2S}$ linkages, is not cleaved by this enzyme.

In light of these studies, it is now apparent that heparinases I and II can cleave the AT-III site at the $H_{NS,3S,6S}{\downarrow}I_{2S}H_{NS,6S}$ linkage, where the scissile linkage is designated with an arrow (A.2 of Penta 1 and B.2 of Penta 2, FIG. 5). Furthermore, with the newly assigned structure for AT-10, we find that linkages with a 3-O sulfate on the reducing end glucosamine, viz., $H_{NS,6S}{\downarrow}GH_{NS,3S,6S}$ are not cleavable by either heparinase II or III (A.1 of Penta 1 and B.1 of Penta 2, FIG. 5). In addition, we find that this inhibition is entirely due to the unusual 3-O sulfate modification. Finally, taken together with our previous studies of the enzymatic action of heparinase I, the AT-10 structure reinforces the fact that heparinase I acts in an exolytic, processive manner on heparin/heparan oligosaccharides (Ernst, S., Rhomberg, A. J., Biemann, K. & Sasisekharan, R. (1998) *Proc. Natl Acad Sci USA* 95, 4182-7).

Figure 9:
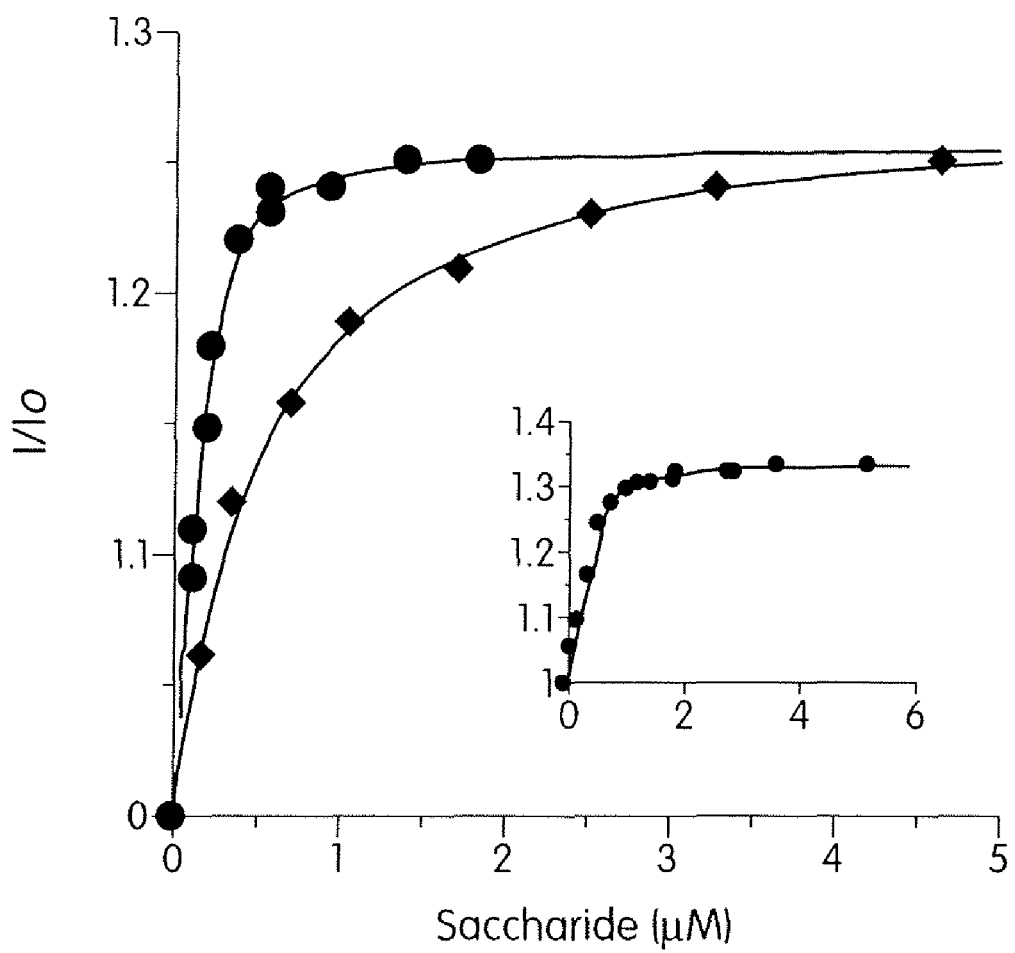
FIG. 9 shows fluorescence titration of AT-III with either full length heparin (●) or AT-10 (♦) at pH 6.0 I=0.025. Data is plotted as the ratio of AT-III fluorescence upon the introduction of saccharide to the initial AT-III fluorescence ($I/I_o$) vs. concentration of added saccharide. The data was fitted by nonlinear regression and the $K_D$ determined. For heparin the measured $K_D$ value was 10 nM, whereas for AT-10 this value was 800 nM. The inset shows the binding of heparin to AT-III at pH 7.4 I=0.15. The measured $K_D$ of 36 nM agrees favorably with other determinations of the affinity of heparin for AT-III.

AT-III Binding to the AT-10 Decasaccharide: Our sequence analysis of AT-10 reported herein and in Shriver, Z., Raman, R., Venkataraman, G., Drummond, K., Turnbull, J., Toida, T., Linhardt, R., Biemann, K. & Sasisekharan, R. (2000) *Proc Natl Acad Sci USA,* 2000 Sep. 12; 97(19):10359-64 revealed that this decasaccharide does not contain an intact AT-III binding pentasaccharide sequence but rather contains only the non reducing end trisaccharide unit. We sought to extend this sequence assignment and provide a functional context to this result by measuring the AT-III binding affinity of AT-10. At pH 7.4, I=0.15, AT-10 has very little affinity for AT-III (FIG. 9). Conversely, under the same conditions, porcine intestinal mucosa heparin bound AT-III with an apparent $K_D$ of 36 nM. To measure accurately an affinity of AT-10 for AT-III, the titration was completed instead at pH 6.2, conditions that are known to promote AT-III binding to saccharides. Under these conditions, AT-10 bound AT-III with an apparent $K_D$ of 0.8 μM while the $K_D$ for full-length heparin decreased to 10 nM. The measured $K_D$ for AT-10 is comparable with similar saccharides with a truncated reducing end, with measured $K_D$ values of 0.3-2 μM (Desai, U. R., Petitou, M., Bjork, I. & Olson, S. T. (1998) *J Biol Chem* 273, 7478-87). Thus, the results of the titration experiments are consistent with AT-10 containing a partially intact AT-III pentasaccharide binding sequence (Desai, U. R., Petitou, M., Bjork, I. & Olson, S. T. (1998) *J Biol Chem* 273, 7478-87). The three saccharide units at the non-reducing end of the pentasaccharide sequence, viz., $H_{NAc,6S}GH_{NS,3S,6S}$, are primarily responsible for binding of the native state of AT-III, while the reducing end disaccharide unit, $I_{2S}H_{NS,6S}$, which is missing in AT-10, is important for binding the active, conformationally-altered AT III. The measured $K_D$ for AT-10 (0.8 μM at pH 6.0, I=0.05) is ~100 times higher than that of full-length heparin, confirming that AT-10 does not contain an intact AT-III pentasaccharide sequence. The decrease in AT-III affinity observed for AT-10 cannot be due simply to a size issue since, in previous studies, the pentasaccharide alone has been shown to have an affinity similar to that of full length heparin (Desai, U. R., Petitou, M., Bjork, I. & Olson, S. T. (1998) *J Biol Chem* 273, 7478-87). Having measured the binding interaction between AT-III and the decasaccharide, we next sought to define the functional consequences of a HLGAG oligosaccharide that contains only a partial AT-III binding site.

Figure 10A:
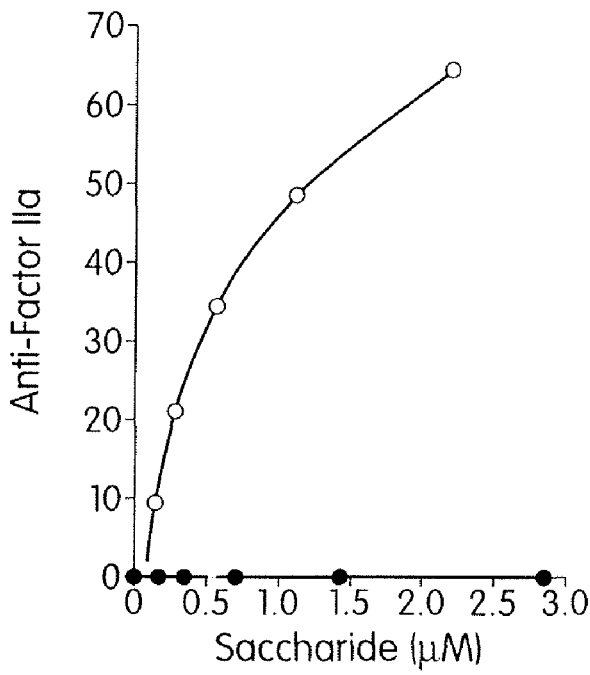
FIG. 10 shows Functional analysis of the AT-10 decasaccharide and comparison to the AT-III binding pentasaccharide. The in vitro anticoagulant activity of the AT-10 decasaccharide (▲) was compared to both the synthetic pentasaccharide (□) or enoxaparin (▨), a low molecular weight heparin generated through chemical cleavage of heparin. The activities of the three compounds was assessed by measuring either (A) anti-IIa activity, (B) anti-Xa activity, (C) anti-Xa activity using purified factor Xa or (D) via HepTest. Also the activated partial thromboplastin time (APTT) and the prothrombin time (PT) was measured wherein none of the compounds displayed significant activity, consistent with their high ratio of anti-Xa:anti-IIa activity.
Figure 10B:
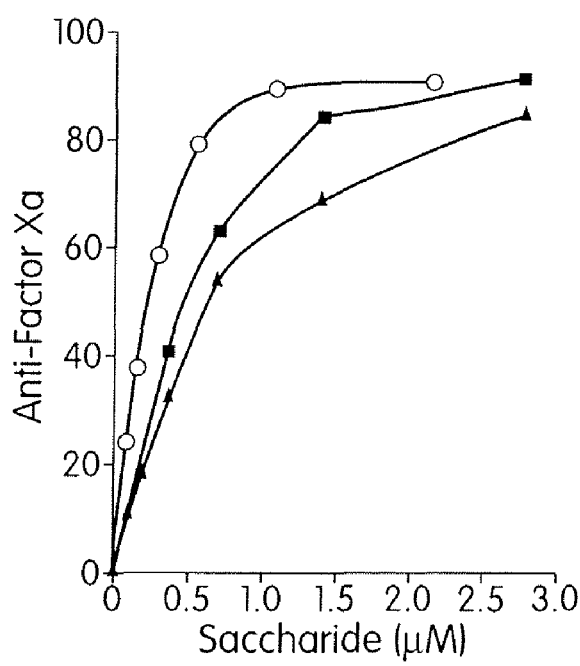

Biological Activity of AT-10: As might be expected for a oligosaccharide that does not contain an intact AT-III site, the biological activity of AT-10 is less than that of either enoxaparin (used here as an example of a LMWH) or the pentasaccharide, Penta 1 (FIG. 10). Consistent with the known mechanism of heparin-mediated inhibition of thrombin activity by AT-III, neither the decasaccharide nor the pentasaccharide have significant anti-IIa activity (FIG. 10a). In the case of the pentasaccharide this lack of activity is entirely due to its size being insufficient to act as a template for the formation of a AT-III/IIa complex. For the decasaccharide, this size constraint is also a probable explanation (since rigorous biochemical studies have implicated oligosaccharides with at least 18 monosaccharide units being important for efficient complex formation) (Petitou, M., Herault; J. P., Bernat, A., Driguez, P. A., Duchaussoy, P., Lormeau, J. C. & Herbert, J. M. (1999) *Nature* 398, 417-22), though the lack of an intact AT-III site may also contribute to its reduced anti-IIa activity.

Figure 10C:
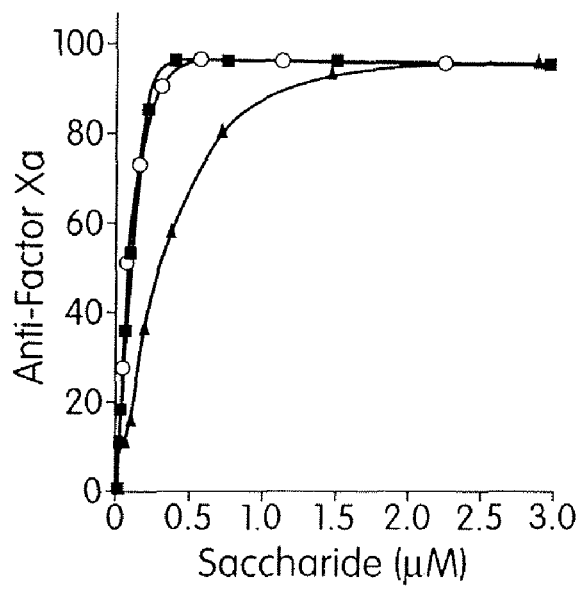
Figure 10D:
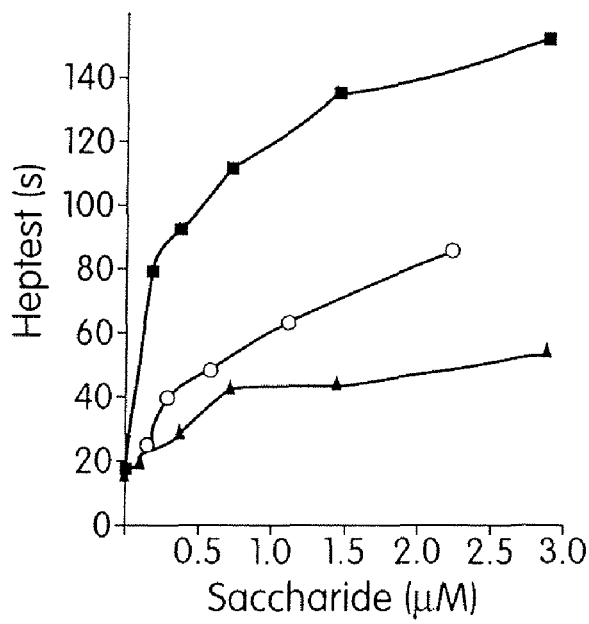

These results are confirmed and extended by examining the anti-Xa activity of the three using factor Xa from serum (FIG. 10b) or purified factor Xa (FIG. 10c). As has been shown previously, inhibition of Factor Xa by AT-III requires binding of the pentasaccharide motif only concomitant with a conformational change in AT-III. In the anti-Xa assay, both enoxaparin and the pentasaccharide have markedly higher activity than the decasaccharide. The $IC_{50}$ values of enoxaparin and the synthetic pentasaccharide are 66 nM and 39 nM, respectively, while that of AT-10 is ten-fold higher at 280 nM. These values are consistent with the lower affinity for AT-III of AT-10 as compared to heparin which was determined in the AT-III fluorescence titration experiments (FIG. 9). That the decasaccharide possesses anti-Xa activity is not surprising since the non-reducing trisaccharide unit (present in the decasaccharide) is primarily responsible for initial binding of heparin to AT-III. The reducing end disaccharide unit, viz., $I_{2S}H_{NS,6S}$ (missing in AT-10) is expected to bind to conformationally altered antithrombin III, stabilizing it. The HepTest measurements (FIG. 10d) yield similar results, viz., enoxaparin and the pentasaccharide have significantly higher activity than the AT-10 decasaccharide. Taken together, the anti-IIa and anti-Xa activities of the decasaccharide as compared to the pentasaccharide and enoxaparin agree well with the AT-III titration experiments as well as the known pharmacology of heparin's mechanism of inhibition of the coagulation cascade.

In summary, it is shown in this example that heparinases I and II cleave the AT-III binding site leaving behind the trisaccharide unit at the reducing end of the oligosaccharide. We also demonstrate that heparinase III does not cleave the AT-III site because of the presence of a 3-O sulfate on the internal glucosamine residue. Thus, to use heparinases I or II for the generation of LMWHs requires extreme caution to ensure retailing intact antithrombin III sites in LMWH fragments. In fact, the results demonstrated herein show that heparinases I or II may be ideal agents for the neutralization of pharmacological doses of heparin.

Example 3

Development of a Compositional Analysis Method and Structural Characterization of Heparins Introduction To purify UFH and identify its components, UGH was exhaustively digested and analyzed using capillary electrophoresis and MALDI mass spectrometry. Capillary electrophoresis (CE) is a very sensitive method with high resolving power for the disaccharide compositional analysis of heparins. A compositional analysis method (CAM) using CE for quantifying the disaccharide building blocks of UFH and LMWH was developed. This method uses less than a microgram of heparin, is time efficient (each CE run is 25 minutes long), is concentration independent, and is highly reproducible. One advantage of this method is its effectiveness as a quality control process that may help minimize batch-to-batch variation in the composition of different LMWH Thus, CE in combination with offline MALDI mass spectrometry has been used to identify a unique tetrasaccharide in the exhaustive digest of UFH, and LMWH. This tetrasaccharide, which forms a part of the AT III binding pentasaccharide domain of glycosaminoglycans, is resistant to further degradation with Heparinase I, II, or III. It is shown below that the utilization of this unique tetrasaccharide in the direct measurement of heparin's anti factor Xa mediated anticoagulant activity.

Methods

Chemicals and Materials: UFH was purchased from Celsus Laboratories (Cincinnati, Ohio) and molar concentrations of stocks were calculated based on an average molecular weight of 13,000 Da. Disaccharide standards were purchased from Sigma-Aldrich (St. Louis, Mo.). Heparinase I, and III are recombinant heparinases. Heparinase II is from *Flavobacterium heparinum* purified as described previously. (Shriver et al. Journal of Biological Chemistry 1998, 273, 22904-22912.)

Compositional Analysis: UFH was subjected to exhaustive depolymerization with an enzyme cocktail made up of Heparinase I, Heparinase II, and Heparinase III. 911 $\mu$l of 10 $\mu$g/$\mu$l concentration of UFH in $H_2O$ was digested with 1 $\mu$l of Enzyme cocktail consisting of 100 nM each of heparinase I, II, and III in 25 mM sodium acetate, 100 mM sodium chloride, 5 mM calcium acetate buffer, pH 7.0 for 12 h at 37° C. The CE sample was prepared by diluting 1 $\mu$l of the digest with 9 $\mu$l of $H_2O$. The samples were analyzed by CE in reverse polarity with a running buffer of 50 mM tris/phosphate, 10 $\mu$M dextran sulfate, pH 2.5. 57 mL of each sample was injected into the CE and run times were 25 minutes. Each sample was digested in duplicate and the experiment was repeated twice for each sample, resulting in four readings per sample. All of the 8 resulting peaks were collected, and the purity of the collected samples was checked by re-injecting into CE, and their mass was measured by offline MALDI Mass Spectrometry. The identity of peaks 1-7 was further confirmed by matching their migration time with that of standard, commercially available disaccharides. For example, the CE spectrum of peak 1 was collected from the CE analysis of total enzyme digest of UFH and a MALDI mass spectrum of peak 1 was generated. Mass spectra were collected using parameters as outlined previously and calibrated externally by using signals for protonated $(RG)_{19}R$ and its complex with a nitrous acid-derived hexasaccharide of the sequence $I_{2S}H_{NS,6S}I_{2S}H_{NS,6S}I_{2S}Man_{6S}$.

Results

Figure 11A:
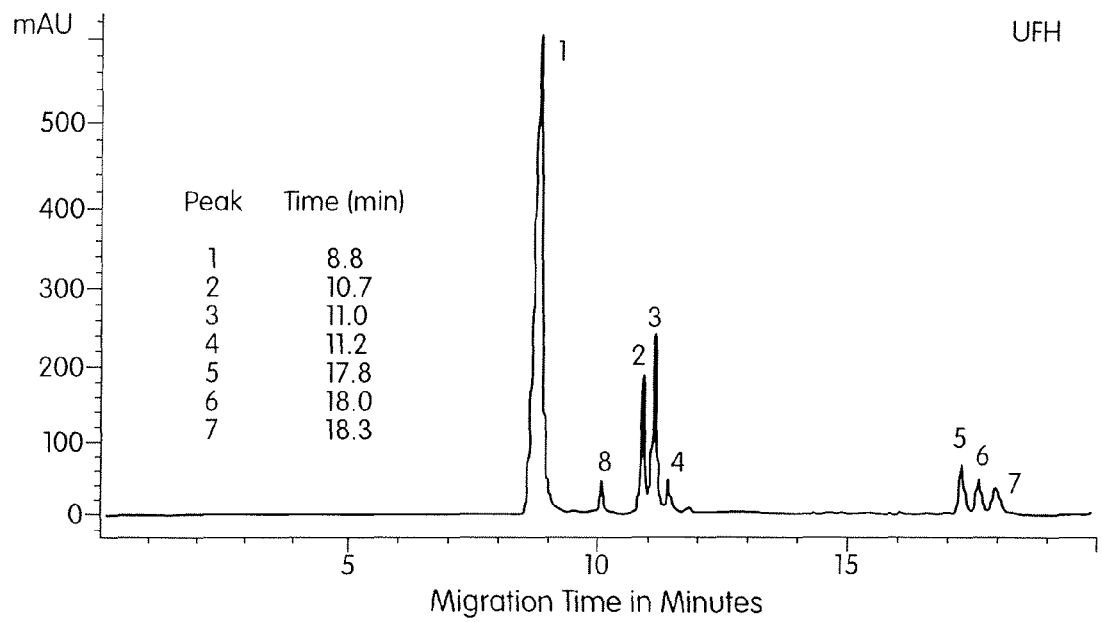
FIGS. 11A and 11B show graphs of compositional analysis of UFH derived from porcine intestinal mucosa. UFH was digested with Heparinase I, II, and III and subjected to Capillary Electrophoresis (CE). Peak 1 (FIG. 9A) was thus confirmed as the trisulfated disaccharide $\Delta U_{2S}H_{NS,6S}$. Peaks 2, 3, and 4 are disulfated disaccharides, and 5, 6, and 7 are monosulfated disaccharides. Peak 8 is the tetrasaccharide $\Delta UH_{NAC,6S}GH_{NS,3S,6S}$. In addition to these, there is a small amount of unsulfated disaccharides migrating much slower than the sulfated saccharides, as shown in FIG. 9B.

As seen in FIG. 11A, eight peaks are seen in the CE spectrum. Each of the peaks labeled 1 through 8 has identical migration time in different samples. Following the collection of each peak and the purity check of each sample by re-injecting into CE, their mass was measured by offline MALDI Mass Spectrometry. Peak 1 has the same mass as the trisulfated heparin disaccharide $\Delta U_{2S},H_{NS,6S}$. The commercial $\Delta U_{2S},H_{NS,6S}$ from Sigma has the same migration time as peak 1 under identical CE conditions. This identifies peak 1 as $\Delta U_{2S},H_{NS,6S}$. In a similar manner, the identities of the seven peaks from 2-7 in the compositional analysis digest of UFH were established. The results are shown in FIGS. 3A and 3B-6A and 6B. The identity of each peak was further confirmed by matching their migration time with that of standard, commercially available disaccharides. Peaks 2, 3, and 4 are disulfated disaccharides, and 5, 6, and 7 are monosulfated disaccharides.

A trace of the CE and MALDI mass spectrum of peak 2 was generated. This peak has the same mass as $\Delta U_{2S},H_{NS}$. Also the commercial $\Delta U_{2S},H_{NS}$ from sigma has the same migration time as peak 2 under identical CE conditions. This confirms that peak 2 is $\Delta U_{2S},H_{NS}$.

A trace of the CE and MALDI mass spectrum of peak 3 was generated. It has the same mass as $\Delta U,H_{NS,6S}$. Also the commercial $\Delta U,H_{NS,6S}$ from sigma has the same migration time as peak 3 under identical CE conditions. This confirms that peak 3 is $\Delta U,H_{NS,6S}$.

A trace of the CE of peak 5 was generated. It has the same mass as $\Delta U,H_{NS}$. Also the commercial $\Delta U,H_{NS}$ from sigma has the same migration time as peak 5 under identical CE conditions. This confirms that peak 5 is $\Delta U,H_{NS}$.

A trace of the CE of peak 6 was generated. It has the same mass as $\Delta U_{2S},H_{NAc}$. Also the commercial $\Delta U_{2S},H_{NAc}$ from sigma has the same migration time as peak 6 under identical CE conditions. This confirms that peak 6 is $\Delta U_{2S},H_{NAc}$.

A trace of the CE of peak 7 was generated. It has the same mass as $\Delta U,H_{NAC,6S}$. Also the commercial $\Delta U,H_{NAC,6S}$ from sigma has the same migration time as peak 7 under identical CE conditions. This confirms that peak 7 is $\Delta U,H_{NAC,6S}$.

In addition to the seven disaccharides, a tetrasaccharide (peak 8) in the exhaustive digest of heparin with heparinase I, II, and III was also identified. This tetrasaccharide was isolated, and its mass was determined by MALDI Mass spectrometry. It had the same migration time in the CE as the tetrasaccharide $\Delta UH_{NAC,6S}GH_{NS,3S,6S}$ that was part of the decasaccharide $\Delta U_{2S}H_{NS,6S}I_{2S}H_{NS,6S}I_{2S}H_{NS,6S}IH_{NAC,6S}GH_{NS,3S,6S}$ whose structure was previously determined. This lead to the confirmation of peak 8 as the tetrasaccharide $\Delta UH_{NAC,6S}GH_{NS,3S,6S}$. This peak is resistant to further degradation with heparinases I, II, or III.

Figure 11B:
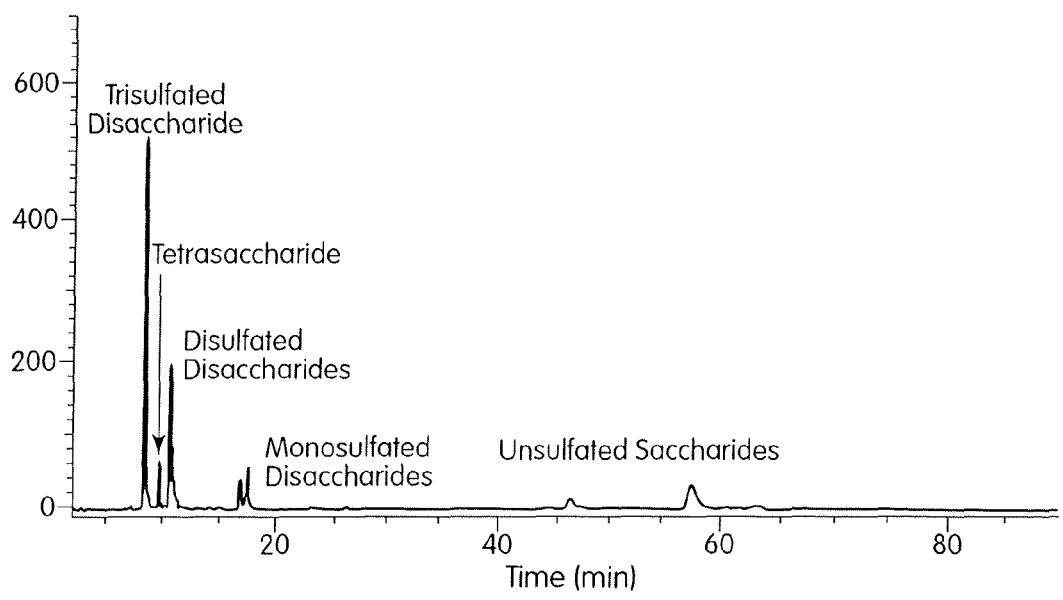

In addition to peaks 1-8, there was a small amount of unsulfated disaccharides migrating much slower than the sulfated saccharides, as shown in FIG. 11B. The unsulfated disaccharides are estimated to constitute <2% of UFH as shown in table 5 (below).

Figure 12:
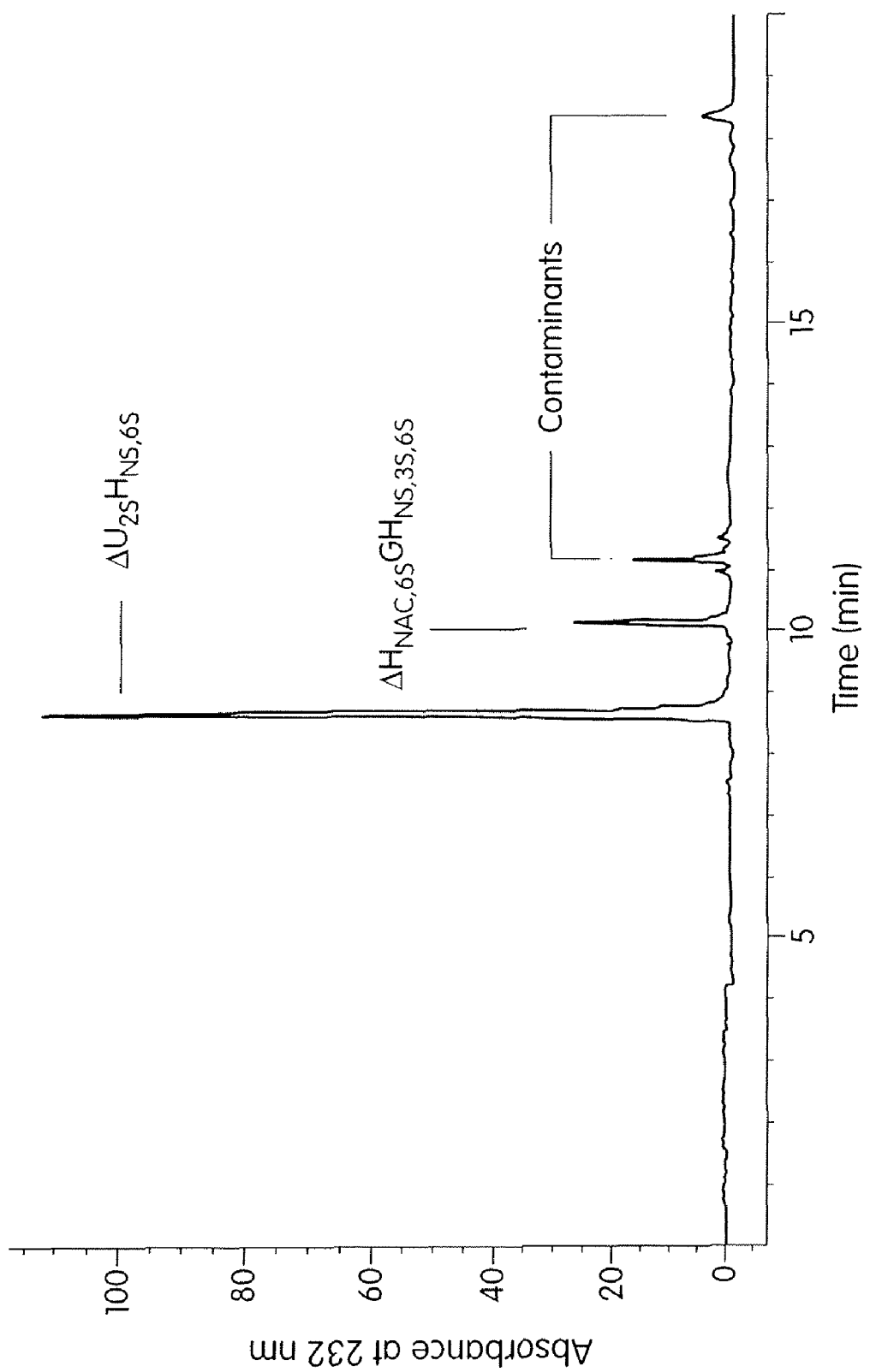
FIG. 12 shows the CE trace of the exhaustive digest of AT-10 pentasaccharide $\Delta U_{2S}H_{NS,6S}$ $\Delta U_{2S}H_{NS,6S}\Delta U_{2S}$ $H_{NS,6S}IH_{NAC,6S}GH_{NS,3S,6S}$. The tetrasaccharide of peak 8 in the exhaustive digest of heparin has the same mass, and migration time as $\Delta UH_{NAC,6S}GH_{NS,3S,6S}$.

FIG. 12 shows the CE trace of the exhaustive digest of AT-10 pentasaccharide $\Delta U_{2S}H_{NS,6S} \Delta U_{2S}H_{NS,6S} \Delta U_{2S}H_{NS,6S} IH_{NAC,6S} GH_{NS,3S,6S}$. Tetrasaccharide 8 in the exhaustive digest of heparin has the same mass, and migration time as $\Delta UH_{NAC,6S}GH_{NS,3S,6S}$. This confirms peak 8 as $\Delta UH_{NAC,6S}GH_{NS,3S,6S}$.

Example 4

UV Response of Disaccharides 1-7

Introduction

The UV response factor (RF) of each of the disaccharides (1-7) was determined to further identify the components of the disaccharides from the exhaustive digest. The RF for a disaccharide is defined as the amount of that disaccharide in ng that gives the same response as one ng of $\Delta U_{2S},H_{NS,6S}$.

Methods

Determining the Response Factor: RF for the different disaccharides was calculated by measuring the UV response of 57 ng of each disaccharides and normalizing it with that of $\Delta U_{2S}, H_{NS,6S}$ as shown in table 5.

Results

Each of the seven disaccharides (1-7) has a different extent of $A_{232}$ UV response. There was an insufficient quantity of tetrasaccharide 8 ($\Delta UH_{NAC,6S}GH_{NS,3S,6S}$) to allow measurement of the $A_{232}$ UV absorbance for this tetrasaccharide. Tetrasaccharides are expected to have lower $A_{232}$ UV absorbance than disaccharides and hence $\Delta UH_{NAC,6S}GH_{NS,3S,6S}$ has been assumed to have the same response as the least responsive of the disaccharides, viz, 1 ($\Delta U_{2S}, H_{NS,6S}$).

TABLE 5

| Compound | Response for 57 ng of disaccharides | Response Factor (RF) |
| --- | --- | --- |
| 1 ($\Delta U_{2S}, H_{NS,6S}$) | 10421.1 | 1 |
| 2 ($\Delta U_{2S}, H_{NS}$) | 13551.45 | 0.769 |
| 3 ($\Delta UH_{NS,6S}$) | 14595.3 | 0.714 |
| 4 ($\Delta U_{2S}, H_{NAC,6S}$) | 13551.45 | 0.769 |
| 5 ($\Delta U, H_{NS}$) | 23956.35 | 0.435 |
| 6 ($\Delta U_{2S}, H_{NAC}$) | 32363.55 | 0.322 |
| 7 ($\Delta U, H_{NAC,6S}$) | 22903.35 | 0.455 |
| 8 ($\Delta UH_{NAC,6S}GH_{NS,3S,6S}$) | 10421.1 (assumption) | 1 |

In Table 5 the response factor (RF) for peaks 1-8 was calculated. The second column gives the UV absorbance at 232 nM for 57 mL injection of 1 ng/nL concentration, i.e., 57 ng of the commercial standard disaccharides (1-7). We could not measure the absorbance the UV absorbance at 232 nM for known concentration of 8 for lack of sample availability in sufficient quantity. 8 is assumed to have the same response as that of the least responsive of the 7 disaccharides, viz, 1. The third column gives the RF for each of the seven peaks, the RF for a disaccharide being defined as the fraction of a ng of it that gives the same response as a ng of 1 ($\Delta U_{2S}, H_{NS,6S}$).

Example 5

Determination of Unsulfated Saccharides in Heparin

Introduction

Although heparin has been classified as a sulfated glycosaminoglycan, it contains a minor amount of unsulfated saccharides. Procedures were undertaken to determine the amount of unsulfated saccharides in heparin. Following this determination, the RF calculated for peaks 1-8 can be used to estimate the weight % of the sulfated building blocks of heparin from the AUC measured by CE.

Methods

A known weight of heparin subjected to exhaustive digestion with the enzyme cocktail was injected into the CE. The area under the curve (AUC) measured for peaks 1-8 in FIG. 11 is converted into the weight of sulfated saccharides using the response for known amounts of peaks 1-8. The difference between the total amount of heparin saccharides injected into the CE, and the total amount of sulfated disaccharides and tetrasaccharide, gives the amount of unsulfated saccharides in the complete digestion of UFH. Multiplying the % relative AUC with the RF gives the corrected relative concentration or the % relative AUC of peaks 1-8 in terms of $\Delta U_{2S}, H_{NS,6S}$.

Results

Table 6 shows the estimation of the unsulfated saccharides in heparin. As shown in table 6, unsulfated saccharides were determined to constitute less than 2% of heparin. The unsulfated saccharides are not taken into account in constructing the compositional analysis table of heparin as explained below. Column 1 of table 7 gives the AUC measured for peaks 1-8. Column 2 gives the % relative AUC. Multiplying the % relative AUC with the RF gives the corrected relative concentration or the % relative AUC of peaks 1-8 in terms of $\Delta U_{2S}, H_{NS,6S}$. These are then normalized to get the weight % of disaccharide peaks 1-7 and tetrasaccharide peak 8. As demonstrated here, construction of this compositional analysis table is independent of the concentration or the weight of the heparin digest analyzed by the CE.

TABLE 6

| Compound | AUC | Response Per 57 ng sample | Amount of saccharide in ng |
| --- | --- | --- | --- |
| 1 ($\Delta U_{2S}, H_{NS,6S}$) | 7294.5 | 10421.1 | 39.9 |
| 2 ($\Delta U_{2S}, H_{NS}$) | 1040.8 | 13551.45 | 4.4 |
| 3 ($\Delta UH_{NS,6S}$) | 1437.9 | 14595.3 | 5.3 |
| 4 ($\Delta U_{2S}, H_{NAC,6S}$) | 379.3 | 13551.45 | 1.6 |
| 5 ($\Delta U, H_{NS}$) | 685.1 | 23956.35 | 1.7 |
| 6 ($\Delta U_{2S}, H_{NAC}$) | 502.9 | 32363.55 | 0.9 |
| 7 ($\Delta U, H_{NAC,6S}$) | 482.3 | 22903.35 | 1.1 |
| 8 ($\Delta UH_{NAC,6S}GH_{NS,3S,6S}$) | 184.7 | 10421.1 (assumption) | 1 |
| Total amount of the sulphated saccharides from 1-8 | | | 55.9 |
| Amount of unsulfated saccharides | | | 57-55.9 = 1.1 ng (1.9%) |

Table 6 shows an estimation of the amount of unsulfated saccharides in the exhaustive digestion of UFH with heparinases I, II, and III. Peaks 1-7 are shown as known disaccharides as explained in FIGS. 2-6. Peak 8 is tetrasaccharide $\Delta UH_{NAC,6S}GH_{NS,3S,6S}$ which is resistant to further degradation by either heparinases I, II, or III. The second column gives the area under the curve (AUC) measured for each of the peaks for a 57 mL injection of 1 ng/nL concentration of compositional analysis digest of UFH. The third column gives the UV absorbance at 232 nM for 57 mL injection of 1 ng/nL concentration of each of the 7 commercial standard disaccharides (1-7). Column 4 gives the weight of the various sulfated saccharides in ng. The difference between their sum (55.9 ng) and the amount of heparin injected (57×1=57 ng) gives the amount of unsulfated saccharides present in the compositional analysis digest of UFH.

Example 6

Verification of Instrumentation and Completeness of Digestion

Introduction

To verify the instrumental reproducibility and to ascertain if the compositional analysis digest is indeed complete under the enzyme concentrations used, samples of UHF were digested in duplicate and analyzed twice by CD. The results were then compared to determine whether there was variability between runs.

Methods

UFH was digested as described in Example 1A, methods with either 1 µl or 5 µl of enzyme cocktail (EC). Each sample was digested in duplicate, and each digest was analyzed twice by CE.

Results

Comparison of duplicate analysis of the same sample (UFH 1/1 with UFH 1/2, UFH 2/1 with UFH 2/2, and UFH 3/2 with UFH 3/2) shows that there is good instrumental reproducibility. Comparison of either UFH 1/1 or UFH 1/2 with UFH 2/1 or UFH 2/2 shows that there is minimal run-to-run variation. Comparison of UFH digested with 1 µl of EC with UFH digested with 5 µl of EC illustrates that increasing the enzyme quantity does not change the disaccharide profile appreciably. This confirms that exhaustive digestion is reached by using 1 µl of EC as shown in FIG. 11. Compositional analysis of LMWH performed by CE as per the protocol outlined in FIG. 11 and table 7 can be used to rigorously compare different batches of LMWH.

TABLE 7

| Compound | AUC | % Relative AUC | Response Factor (RF) | Corrected relative concentration | Weight % |
|---|---|---|---|---|---|
| 1 ($\Delta U_{2S},H_{NS,6S}$) | 7294.5 | 60.7 | 1 | 60.7 | 70.9 |
| 2 ($\Delta U_{2S},H_{NS}$) | 1040.8 | 8.7 | 0.769 | 6.7 | 7.8 |
| 3 ($\Delta UH_{NS,6S}$) | 1437.9 | 12.0 | 0.714 | 8.6 | 10.0 |
| 4 ($\Delta U_{2S},H_{NAC,6S}$) | 379.3 | 3.2 | 0.769 | 2.5 | 2.9 |
| 5 ($\Delta U,H_{NS}$) | 685.1 | 5.7 | 0.435 | 2.5 | 2.9 |
| 6 ($\Delta U_{2S},H_{NAC}$) | 502.9 | 4.2 | 0.322 | 1.4 | 1.6 |
| 7 ($\Delta U,H_{NAC,6S}$) | 482.3 | 4.0 | 0.455 | 1.8 | 2.1 |
| 8 ($\Delta UH_{NAC,6S}GH_{NS,3S,S}$) | 184.7 | 1.5 | 1 | 1.5 | 1.8 |

Table 7 shows the values for Compositional Analysis for UFH. The area under the curve (AUC) was measured for each peak from the CE spectrum of UFH digested with the enzyme cocktail as shown in FIG. 11. The response factor calculated for each saccharide as shown in table 6 was used to calculate their corrected relative concentration in the enzyme digest. The last column gives the weight percentage of each of the building block of UFH. The unsulfated saccharides, which constitute <2% of UFH, is not taken into consideration in constructing this compositional analysis table. As demonstrated here, construction of this compositional analysis table as shown by this method is independent of the concentration or the weight of the heparin digest analyzed by the CE.

Example 7

Determining the Efficiency of AT-III Mediated Anti-Factor Xa Anticoagulant Action of Heparin: Correlation Between $IH_{NAC,6S}GH_{NS,3S,6S}$ and Anti-Xa Activity Introduction The quantification of $\Delta UH_{NAC,6S}GH_{NS,3S,6S}$ tetrasaccharide by CAM has an additional role in estimating the efficacy of AT-III mediated anti-factor Xa anticoagulant action of heparin. $\Delta UH_{NAC,6S}GH_{NS,3S,6S}$ is a part of the AT-III binding pentasaccharide. Quantification of $\Delta UH_{NAC,6S}GH_{NS,3S,6S}$ is a measure of the determination of the amount of AT-III binding pentasaccharide present in heparin and thus it helps in the direct measurement of anti-factor Xa mediated anticoagulation of heparin that is dependent on the AT-III binding pentasaccharide domain of heparin.

Methods

UFH was size fractionated through P10 size exclusion column. Compositional analysis wag performed on the resulting fractions to estimate their $\Delta UH_{NAC,6S}GH_{NS,3S,6S}$ content. These fractions were also assayed for their anti-factor Xa activity.

Results

A plot of anti-factor Xa activity of different fractions as a function of their $\Delta UH_{NAC,6S}GH_{NS,3S,6S}$ results in a straight line with r=0.91, as shown in FIG. 11. This indicates that the anti factor Xa mediated anticoagulant action of heparins may be directly measured from their $\Delta UH_{NAC,6S}GH_{NS,3S,6S}$ content. The data is also presented in Table 8.

TABLE 8

| Sample | 1 $\Delta U_{2S},H_{NS,6S}$ | 2 $\Delta U_{2S},H_{NS}$ | 3 $\Delta U,H_{NS,6S}$ | 4 $\Delta U_{2S},H_{NAC,6S}$ | 5 $\Delta U,H_{NS}$ | 6 $\Delta U_{2S},H_{NAC}$ | 7 $\Delta UH_{NAC,6S}$ | 8 $\Delta UH_{NAC,6S}GH_{NS,3S,6S}$ |
|---|---|---|---|---|---|---|---|---|
| UFH 1/1 1 µl EC | 70.9 | 7.8 | 10.0 | 2.9 | 2.9 | 1.6 | 2.1 | 1.8 |
| UFH 1/2 1 µl EC | 71.0 | 7.7 | 10.2 | 3.0 | 2.8 | 1.5 | 2.0 | 1.8 |
| UFH 2/1 1 µl EC | 71.5 | 7.5 | 10.1 | 2.9 | 2.7 | 1.5 | 2.1 | 1.7 |
| UFH 2/2 1 µl EC | 71.3 | 7.5 | 10.3 | 2.8 | 2.8 | 1.5 | 2.0 | 1.8 |
| UFH 3/1 5 µl EC | 72.0 | 7.3 | 10.0 | 2.8 | 2.8 | 1.6 | 1.8 | 1.7 |
| UFH 3/2 5 µl EC | 72.2 | 7.5 | 9.9 | 2.7 | 2.7 | 1.6 | 1.7 | 1.7 |

Table 8 shows a Compositional analysis of UFH performed by CE as per the protocol outlined in FIG. 11 and table 7 can be used to rigorously compare different batches of LMWH. UFH was digested with either 1 µl or 5 µl of enzyme cocktail (EC). Each sample was digested in duplicate and each digest was analyzed in duplicate by CE. In all the samples, saccharide peaks 1-8 had the same migration time. Comparison of duplicate analysis of the same sample (UFH 1/1 with UFH 1/2, UFH 2/1 with UFH 2/2, and UFH 3/1 with UFH 3/2) shows that there is good instrumental reproducibility. Comparison of either UFH 1/1 or UFH 1/2 with UFH 2/1 or UFH 2/2 shows that there is minimal run-to-run variation. Comparison of UFH digested with 1 µl of EC with MI digested with 5 µl of EC illustrates that increasing the enzyme quantity does not change the disaccharide profile appreciably showing that exhaustive digestion is reached by using 1 µl of EC as shown in FIG. 11.

Example 8

Generation of LMWH Fractions and Characterization of Biological Activity

Methods:
LMWH fractions MS 57-1 through MS 57-4 and MS 59-1 to MS59-4 were prepared by treating UFH with 200 µg of Heparinase III (as described above) and passing the resulting product through a P10 column.
LMWH fractions MS56-1 through MS56-4 were prepared by treating UFH with 1000 µg of Heparinase III, and passing the resulting product through a P10 column.
LMWH fractions MS60-1 through MS 60-3, and MS55-1 through MS55-4 were generated by treating Fraction 2 with 200 µg of Heparinase III, and passing the resulting product through a P10 column.
LMWH fractions MS 66-1 and MS66-2 were prepared by treating Fraction 2 with 1000 µg of Heparinase III, and passing the resulting product through a P10 column.
Fraction 1 is the high molecular weight heparin that is precipitated upon treating UFH with Barium acetate at room temperature, as described in the Volpi reference described above.

Results:
Table 9 provides the compositional and functional analysis of the LMWH preparations prepared according to the invention and of the control fraction 1. The table lists the MW, in vitro activity, and composition of the various fractions.

MS55-2 showed very similar pharmacokinetics to that of enoxaparin as evident in the comparable absorption and elimination phase as well as $T_{max}$. The bioavailability and Peak concentration were comparable among all three LMWHs tested by Subcutaneous injection. When administered by the IV route, the initial anti-Xa activity is much higher for MS55-2 in comparison with Aredeparin. Again, the bioavailability between the two LMWHs was almost identical. Both ardeparin and MS55-2 exhibited exponential decrease in anti-Xa activity, and thus the elimination follows first-order pharmacokinetics.

Figure 13:
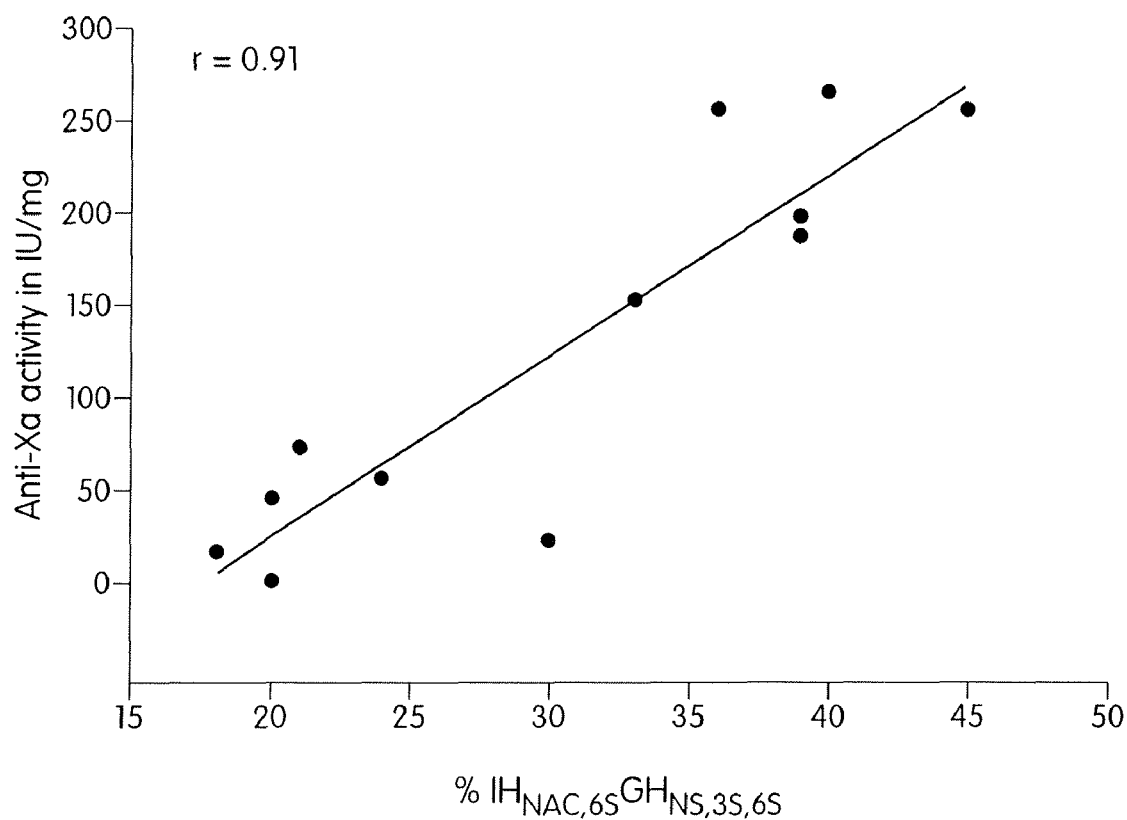
FIG. 13 is a graph of anti-factor Xa activity for different fractions of UFH as a function of their $\Delta UH_{NAC,6S}GH_{NS,3S,6S}$ content. A plot of anti-factor Xa activity as a function of % $\Delta UH_{NAC,6S}GH_{NS,3S,6S}$ gives a straight line with r=0.91.

The anti-Xa activity of MS55-2 was observed to be 205 IU/mg. This is higher than the LMWHs such as Enoxaparin (135 IU/mg), Ardeparin (93 IU/mg) that are currently available in the United States. The results are also shown in FIG. 13.

The foregoing written specification is considered to be sufficient to enable one skilled in the art to practice the invention. The present invention is not to be limited in scope by examples provided, since the examples are intended as a

TABLE 9

Generation of Heparin of selected MW/Charge/Biological Properties

| Method | Sample | Wt. (mg) | Average MW | PD | anti-Xa IU/mg | anti-IIa IU/mg | Xa/IIa | Wt % 1 | Wt % 8 | Wt % 2 | Wt % 3 | Wt % 4 | Wt % 5 | Wt % 6 | Wt % 7 |
|---|---|---|---|---|---|---|---|---|---|---|---|---|---|---|---|
| | Fraction 2 | 300 | <8000 | | 400.0 | 75 | 5.3 | 70.0 | 4.5 | 7.8 | 11.1 | 3.2 | 2.4 | 1.4 | 0 |
| | Fraction 1 | 150 | 8000-14,000 | | 105.6 | 54.5 | 2.0 | 87.2 | 0 | 9.0 | 1.6 | 0.4 | 1.8 | 0 | 0 |
| UFH, | MS57-1 | 130 | 8743 ± 177 | 1.1 | 292.9 | 72.3 | 4.0 | 77.8 | 3.5 | 3.0 | 10.7 | 1.4 | 0.3 | 0.2 | 3.0 |
| 200 µg | MS57-2 | 140 | 6010 ± 138 | 1.1 | 186 | 33.33 | 5.6 | 75.5 | 3.5 | 4.0 | 10.7 | 1.6 | 0.5 | 0.4 | 3.8 |
| HepIII, | MS57-3 | 60 | 3000-5000 | | 70.8 | 0 | | 73.9 | 2.8 | 4.9 | 10.2 | 1.8 | 1.2 | 0.6 | 5.0 |
| P10 | MS57-4 | 10 | <3000 | | 42.6 | 0 | | 73.9 | 1.5 | 4.4 | 10.0 | 1.3 | 2.0 | 0.9 | 0.4 |
| | MS59-1 | 130 | 8800 | | 255 | 29.2 | 8.7 | 73.1 | 4.3 | 5.8 | 11.5 | 2.5 | 0 | 0.5 | 2.4 |
| | MS59-2 | 130 | 6500 | | 255 | 54.5 | 4.7 | 77.8 | 3.8 | 3.2 | 10.3 | 1.3 | 0.4 | 0.3 | 3.4 |
| | MS59-3 | 70 | 3000-5000 | | 54 | 0 | | 75.3 | 2.3 | 4.6 | 10.2 | 1.9 | 0.8 | 0.8 | 3.8 |
| | MS59-4 | 30 | <3000 | | 15 | 0 | | 71.3 | 1.9 | 5.7 | 9.4 | 1.9 | 1.8 | 2.0 | 6.2 |
| UFH, | MS56-1 | 60 | 9204 ± 192 | 1.2 | 261.4 | 50 | 5.2 | 78.8 | 4.7 | 3.3 | 9.3 | 1.7 | 0.2 | 0.3 | 2.2 |
| 1000 µg | MS56-2 | 40 | 6000 ± 146 | 1.2 | 123.8 | 75 | 1.7 | 70.7 | 3.8 | 7.0 | 10.5 | 2.8 | 1.2 | 1.0 | 2.9 |
| HepIII, | MS56-3 | 100 | 3000-5000 | | 126.9 | 36.4 | 3.5 | 76.4 | 3.0 | 4.1 | 11.0 | 1.5 | 0.5 | 0.3 | 3.6 |
| P10 | MS56-4 | 80 | <3000 | 31 | 0 | 78.7 | 0 | 5.0 | 12.0 | 2.1 | 0 | 0 | 0 | | |
| Fraction 2, | MS60-1 | 110 | 7224 ± 139 | 1.2 | 347.4 | 58.33 | 6.0 | 68.8 | 5.0 | 6.0 | 13.1 | 2.8 | 0.4 | 0.5 | 3.0 |
| 200 µg | MS60-2 | 140 | 5736 ± 238 | 1.1 | 353.6 | 75 | 1.5 | 69.9 | 3.8 | 6.2 | 13.0 | 2.1 | 0.8 | 0.7 | 3.8 |
| HepIII, | MS60-3 | 140 | <5000 | | 51 | 0 | | 65.9 | 0 | 5.7 | 12.7 | 2.2 | 3.7 | 1.7 | 8.4 |
| P10 | MS55-1 | 140 | 6505 ± 100 | 1.1 | 335 | 60.0 | 5.6 | 68.6 | 6.5 | 5.5 | 13.9 | 3.3 | 0.3 | 0.3 | 2.1 |
| Fraction 2, | MS55-2 | 130.0 | 5964 ± 87 | 1.1 | 201.2 | 54.6 | 3.7 | 74.4 | 4.9 | 3.7 | 11.3 | 2.6 | 0 | 0 | 3.5 |
| 1000 µg | MS55-3 | 50.0 | 3000-5000 | | 11.6 | 0 | | 76.1 | 2.3 | 4.4 | 9.8 | 1.7 | 0.8 | 0.6 | 4.2 |
| HepIII, | MS55-4 | 30 | <3000 | | 15.6 | 0 | | 73.4 | 0 | 5.0 | 9.8 | 2.0 | 1.8 | 1.0 | 6.5 |
| P10 | MS66-1 | 150 | 6470 ± 142 | 1.2 | 250.1 | 100 | 2.5 | 75.0 | 3.6 | 7.5 | 8.6 | 8.6 | 3.8 | 1.0 | 0.3 |
| | MS66-2 | 150 | 5592 ± 159 | 1.1 | 206.0 | 20.8 | 6.0 | 74.0 | 3.6 | 7.8 | 9.2 | 3.4 | 1.1 | 1.0 | 0.2 |

Fraction 2 is the second fraction of a lower MW that is precipitated upon keeping the Barium acetate treated Heparin at 4C. This is the fraction used according to the methods of the invention.

The subcutaneous and in vivo absorption profiles of MS55-2 were measured. The absorption profile of MS55-2 was compared with that of commercially available LMWH Ardeparin, and Enoxaparin. The anti-Xa activity of the various heparin species were also assayed for their in vitro biological activity.

single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for analyzing a heparin sample, comprising:
   contacting the sample with heparinase I, heparinase II and heparinase III;
   determining an amount of a signature component in the sample, and
   comparing the amount of the signature component in the sample to a reference database for a heparin to analyze an activity of the heparin sample,
   wherein the signature component is selected from the group consisting of: $\Delta UH_{NAc,6S}GH_{NS,3S,6S}$; $\Delta UH_{NS,6S}GH_{NS,3S,6S}$; $\Delta UH_{NAc,6S}GH_{NS,3S}$; $\Delta UH_{NS,6S}GH_{NS,3S}$; $\Delta U_{2S}H_{NS,6S}I_{2S}H_{NS,6S}I_{2S}H_{NS,6S}IH_{NAc,6S}GH_{NS,3S,6S}$; $\Delta U_{2S}H_{NS,6S}IH_{NS,6S}I_{2S}H_{NS,6S}IH_{NAc,6S}GH_{NS,3S,6S}$; $\Delta U_{2S}H_{NS,6S}GH_{NS,6S}I_{2S}H_{NS,6S}IH_{NAc,6S}GH_{NS,3S,6S}$; $\Delta U_{2S}H_{NS,6S}I_{2S}H_{NS,6S}I_{2S}H_{NS,6S}IH_{NAc,6S}GMan_{3S,6S}$; $I_{2S}H_{NS,6S}I_{2S}H_{NS,6S}IH_{NAc,6S}GH_{NS,3S,6S}$; $\Delta U_{2S}H_{NS,6S}I_{2S}H_{NS,6S}IH_{NAc,6S}GH_{NS,3S,6S}$; $I_{2S}H_{NS,6S}I_{2S}H_{NS,6S}IH_{NAc,6S}GMan_{3S,6S}$; $\Delta U_{2S}H_{NS,6S}IH_{NAc,6S}GH_{NS,3S,6S}$; $I_{NS,6S}IH_{NAc,6S}GH_{NS,3S,6S}$; $\Delta U_{2S}H_{NS,6S}I_{2S}H_{NS,6S}$; $\Delta U_{2S}H_{NS,6S},IH_{NS,6S}$; $\Delta U_{2S}H_{NS,6S}GH_{NS,6S}$; $\Delta U_{2S}H_{NS,6S}I_{2S}Man_{6S}$; $IH_{NAc,6S}GMan_{3S,6S}$; $H_{NAc,6S}GMan_{3S,6S}$; $H_{NS,6S}GH_{NS,3S,6S}I_{2S}H_{NS,6S,OMe}$; $H_{NS,6S}GH_{NS,6S}I_{2S}H_{NS,6S,OMe}$; $\Delta UH_{NS,6S}I_{2S}H_{NS,6S,OMe}$; $H_{NS,6S}GH_{NS,6S}$; $H_{NS,6S}GH_{NS,3S,6S}$; $\Delta U_{2S}H_{NS,6S,OMe}$; $\Delta U_{2S}H_{NS,6S}$; $\Delta U_{2S}H_{NS}$; $\Delta UH_{NS,6S}$; $\Delta U_{2S}H_{NAc,6S}$; $\Delta UH_{NS}$; $\Delta U_{2S}H_{NAc}$; $\Delta UH_{NAc,6S}$ and $\Delta UH_{NS,3S,6S}$.

2. The method of claim 1, wherein the sample is contacted with heparinase I, heparinase II heparinase III, a sulfatase and a glucuronidase.

3. The method of claim 2, wherein the sulfatase is a 2-O sulfatase.

4. The method of claim 1, wherein the heparin sample is a pharmaceutical product.

5. The method of claim 1, wherein the heparin sample is a pharmaceutical grade product governed by the USP.

6. The method of claim 1, wherein the heparin sample is a commercial product.

7. The method of claim 1, wherein the heparin sample is a low molecular weight heparin (LMWH) sample.

8. The method of claim 7, wherein the LMWH sample is made by a process comprising eliminative cleavage with benzyl ester of heparin by alkaline treatment.

9. The method of claim 7, wherein the LMWH sample is an enoxaparin sample.

10. The method of claim 7, wherein the LMWH sample is made by a process comprising partial nitrous depolymerization of unfractionated heparin.

11. The method of claim 7, wherein the LMWH sample is a fragmin sample.

12. The method of claim 1, wherein the heparin sample is an unfractionated heparin sample.

13. The method of claim 7, wherein the LMWH sample is made by a process comprising salt precipitation of an unfractionated heparin in a solvent that produces a first high molecular weight fraction and a second fraction of LMWH, wherein the first molecular weight fraction is separated from the second molecular weight fraction, and processing the second fraction with enzymatic digestion to produce a concentrated LMWH preparation.

14. The method of claim 13, wherein said process comprises enzymatic digestion with a heparin degrading enzyme.

15. The method of claim 14, wherein the heparin degrading enzyme is heparinase III.

16. The method of claim 15, wherein the heparinase III is a modified heparinase III comprising the amino acid sequence of the mature peptide of SEQ ID NO:2 wherein at least one histidine residue selected from the group consisting of His 36, His105, His110, His139, His152, His225, His234, His241, His424, His469, and His539 of the heparinase III has been substituted.

17. The method of claim 16, wherein the at least one histidine residue has been substituted with alanine, serine, tyrosine, threonine, or lysine.

18. The method of claim 17, wherein the at least one histidine residue is His225 that has been substituted with alanine.

19. The method of claim 13, wherein the salt precipitation is performed with a salt of divalent cations and weak anions.

20. The method of claim 19, wherein the salt of the divalent cation is selected from the group consisting of barium, calcium, magnesium, strontium, copper, nickel, cadmium, zinc, mercury, beryllium, nickel, palladium, platinum, iron and tin.

21. The method of claim 19, wherein the divalent cation is calcium.

22. The method of claim 13, wherein the salt precipitation is performed with calcium acetate.

23. The method of claim 13, wherein the solvent is selected from $H_2O$, $H_2O$ and ethanol, ethanol, $H_2O$ and acetone, and acetone.

24. The method of claim 23, wherein the solvent is $H_2O$ and ethanol.

25. The method of claim 13, wherein the second fraction of LMWH is contained in the supernatant.

26. The method of claim 13, wherein the process for making the LMWH further comprises precipitation of the second fraction of LMWH with a solvent.

27. The method of claim 26, wherein the solvent is selected from ethanol and the combination of $H_2O$ and ethanol.

28. The method of claim 1, wherein the reference database is embodied in a computer readable medium.

29. The method of claim 1, further comprising: evaluating the quality of the sample based on whether the sample has a signature component in a preselected range.

30. The method of claim 1, wherein the amount of signature component is calculated by the equation:

$$PRA = RF \times AUC_{\% R},$$

wherein
PRA=percent relative amount of a signature component,
RF=response factor,
$AUC_{\% R}$=percent relative AUC,
$AUC_C$=area under the curve for one signature component,
$AUC_T$=sum of area under the curve for all signature components.

* * * * *

UNITED STATES PATENT AND TRADEMARK OFFICE
CERTIFICATE OF CORRECTION

PATENT NO.        : 8,173,384 B2                                         Page 1 of 1
APPLICATION NO.   : 12/509774
DATED             : May 8, 2012
INVENTOR(S)       : Ram Sasisekharan It is certified that error appears in the above-identified patent and that said Letters Patent is hereby corrected as shown below:

Please delete the paragraph titled 'GOVERNMENT SUPPORT' encompassing column 1, lines 20-23:

"The present invention was supported in part by a grant from the United States National Institutes of Health under contract/grant number GM 57073. The U.S. Government may retain certain rights in the invention."

and replace with:

--This invention was made with government support under Grant No. R01 GM57073 awarded by the National Institutes of Health. The government has certain rights in this invention.--

Signed and Sealed this
Thirtieth Day of October, 2012

David J. Kappos
*Director of the United States Patent and Trademark Office*